United States Patent
Chevallier et al.

(10) Patent No.: US 11,859,203 B2
(45) Date of Patent: Jan. 2, 2024

(54) CELL CULTURE METHODS

(71) Applicant: UCB BIOPHARMA SRL, Brussels (BE)

(72) Inventors: Valentine Chevallier, Brussels (BE); Nadine Kochanowski, Brussels (BE); Laetitia Malphettes, Brussels (BE); Vincent Adolphe Carol Cool, Brussels (BE)

(73) Assignee: UCB BIOPHARMA SRL, Brussels (BE)

( * ) Notice: Subject to any disclaimer, the term of this patent is extended or adjusted under 35 U.S.C. 154(b) by 519 days.

(21) Appl. No.: 16/768,091

(22) PCT Filed: Nov. 29, 2018

(86) PCT No.: PCT/EP2018/083010
§ 371 (c)(1),
(2) Date: May 29, 2020

(87) PCT Pub. No.: WO2019/106091
PCT Pub. Date: Jun. 6, 2019

(65) Prior Publication Data
US 2020/0308536 A1 Oct. 1, 2020

(30) Foreign Application Priority Data
Dec. 1, 2017 (EP) .................. 17204978

(51) Int. Cl.
*C12N 5/00* (2006.01)
*C07K 16/46* (2006.01)

(52) U.S. Cl.
CPC .......... *C12N 5/0018* (2013.01); *C07K 16/461* (2013.01); *C07K 2317/14* (2013.01); *C07K 2317/24* (2013.01); *C07K 2317/515* (2013.01); *C12N 2500/32* (2013.01)

(58) Field of Classification Search
None
See application file for complete search history.

(56) References Cited

U.S. PATENT DOCUMENTS

| 8,765,413 B2 | 7/2014 | Joosten et al. |
| 11,555,175 B2 | 1/2023 | Williams et al. |
| 2002/0115723 A1* | 8/2002 | Iwasaki ............... A61K 8/0212 514/616 |
| 2006/0148074 A1 | 7/2006 | Gorfien et al. |
| 2013/0281355 A1 | 10/2013 | Vijayasankaran et al. |

FOREIGN PATENT DOCUMENTS

| WO | WO 98/08934 | 3/1998 |
| WO | WO 2008/033517 | 3/2008 |
| WO | WO 2013/158275 | 10/2013 |
| WO | WO 2017/186654 | 11/2017 |

OTHER PUBLICATIONS

Moreira "A systematic structural comparison of all solved small proteins deposited in PDB. The effect of disulfide bonds in protein fold" CSBJ 19:6255-6262 (Year: 2021).*
Mossuto "Disulfide Bonding in Neurodegenerative Misfolding Diseases" IJCB 2013:1-7 (Year: 2013).*
Kitazawa "Intracellular redox regulation by a cystine derivative suppresses UV-induced NF-UB activation" FEBS 526:106-110 (Year: 2002).*
Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
Banks, D. D. et al. "The Effect of Sucrose Hydrolysis on the Stability of Protein Therapeutics during Accelerated Formulation Studies" *Journal of Pharmaceutical Sciences*, 2009, pp. 4501-4510, vol. 98, No. 12.
Hecklau, C. et al. "S-Sulfocysteine simplifies fed-batch processes and increases the CHO specific productivity via anti-oxidant activity" *Journal of Biotechnology*, Dec. 2, 2015, pp. 53-63, vol. 218.
Kitazawa, M. et al. "Intracellular redox regulation by a cystine derivative suppresses UV-induced NF-κB activation" *FEBS Letters*, Aug. 2002, pp. 106-110, vol. 526, No. 1-3.
Kshirsagar, R. et al. "Controlling Trisulfide Modification in Recombinant Monoclonal Antibody Produced in Fed-Batch Cell Culture" *Biotechnology and Bioengineering*, Oct. 2012, pp. 2523-2532, vol. 109, No. 10.
Oh, H. K. et al. "Effect of N-Acetylcystein on Butyrate-Treated Chinese Hamster Ovary Cells to Improve the Production of Recombinant Human Interferon-β-1a" *Biotechnol. Prog.*, 2005, pp. 1154-1164, vol. 21, No. 4.
Purdie, J. et al. "Cell Culture Media Impact on Drug Product Solution Stability" *Biotechnology Prog.*, 2016, pp. 998-1008, vol. 32, No. 4.
Seibel, R. et al. "Impact of S-sulfocysteine on fragments and trisulfide bond linkages in monoclonal antibodies" *MABS*, 2017, pp. 889-897, vol. 9, No. 6.
Zang, L. et al. "Metabolomics Profiling of Cell Culture Media Leading to the Identification of Riboflavin Photosensitized Degradation of Tryptophan Causing Slow Growth in Cell Culture" *Anal. Chem.*, 2011, pp. 5422-5430, vol. 83.
Written Opinion in International Application No. PCT/EP2018/083010, dated Feb. 4, 2019, pp. 1-8.

\* cited by examiner

*Primary Examiner* — Adam Weidner
(74) *Attorney, Agent, or Firm* — SALIWANCHIK, LLOYD & EISENSCHENK

(57) ABSTRACT

The present invention relates to methods for reducing the heterogeneity of a population of recombinant proteins produced in cell culture, said methods comprising growing host cells producing a recombinant protein in a cell culture medium wherein the cell culture medium comprises one or more cysteine/cystine analogs.

23 Claims, 26 Drawing Sheets
Specification includes a Sequence Listing.

Figure 1 : Viable cell concentration

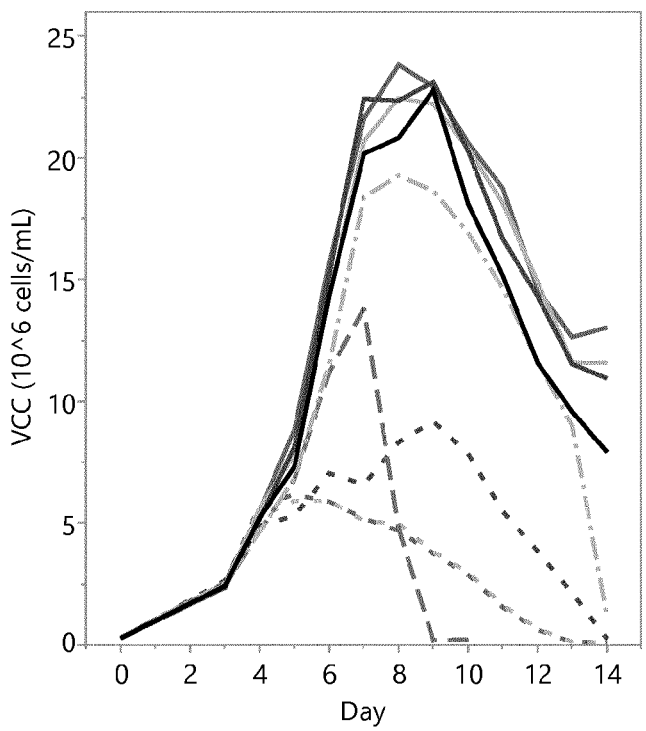

Overlay

— Control 100% Cysteine Feed
····· 100% N-acetyl-cysteine Feed
····· 100% N,N'-diacetyl cystine Feed
····· 100% N,N'-diacetyl-L-cystine dimethylester Feed
━ ━ 100% S-Sulfocysteine Feed
━━━ 50% N-acetyl-cysteine 50% Cysteine Feed
━━━ 50% N,N'-diacetyl cystine 50% Cysteine Feed
━━━ 50% N,N'-diacetyl-L-cystine dimethylester 50% Cysteine Feed
━ ━ 50% S-Sulfocysteine 50% Cysteine Feed

Figure 2 : Relative % change in Mab titer on day 14 with respect to control (100% Cysteine Feed)
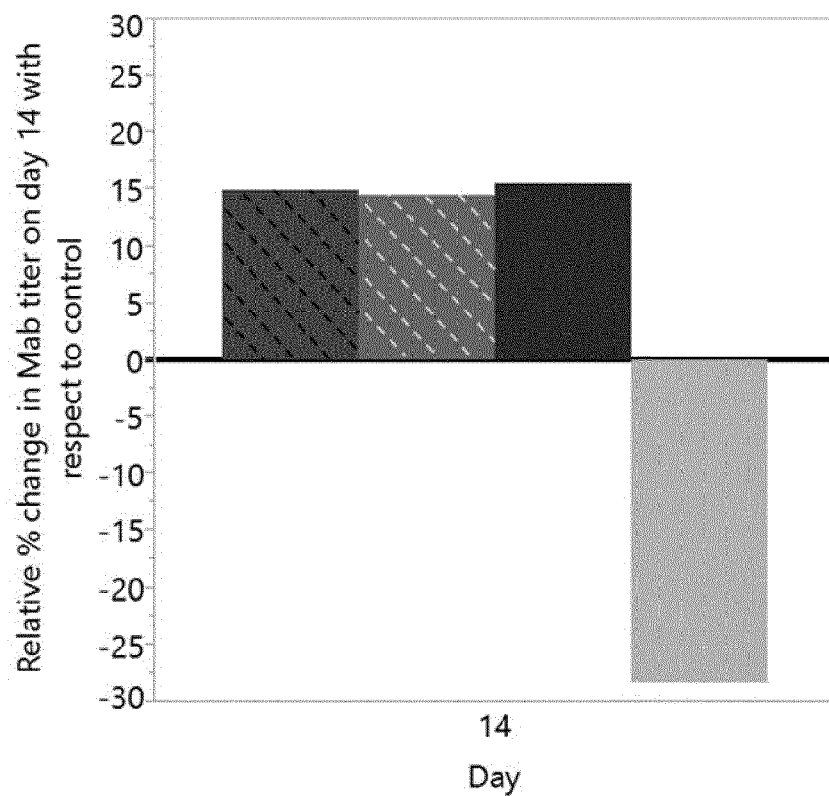
Overlay
- 50% N-acetyl-cysteine 50% Cysteine Feed
- 50% N,N'-diacetyl cystine 50% Cysteine Feed
- 50% N,N'-diacetyl-L-cystine dimethylester 50% Cysteine Feed
- 50% S-Sulfocysteine 50% Cysteine Feed Figure 3 : Relative % change in color intensity (b*value) level on day 14 with respect to control (100% Cysteine Feed)
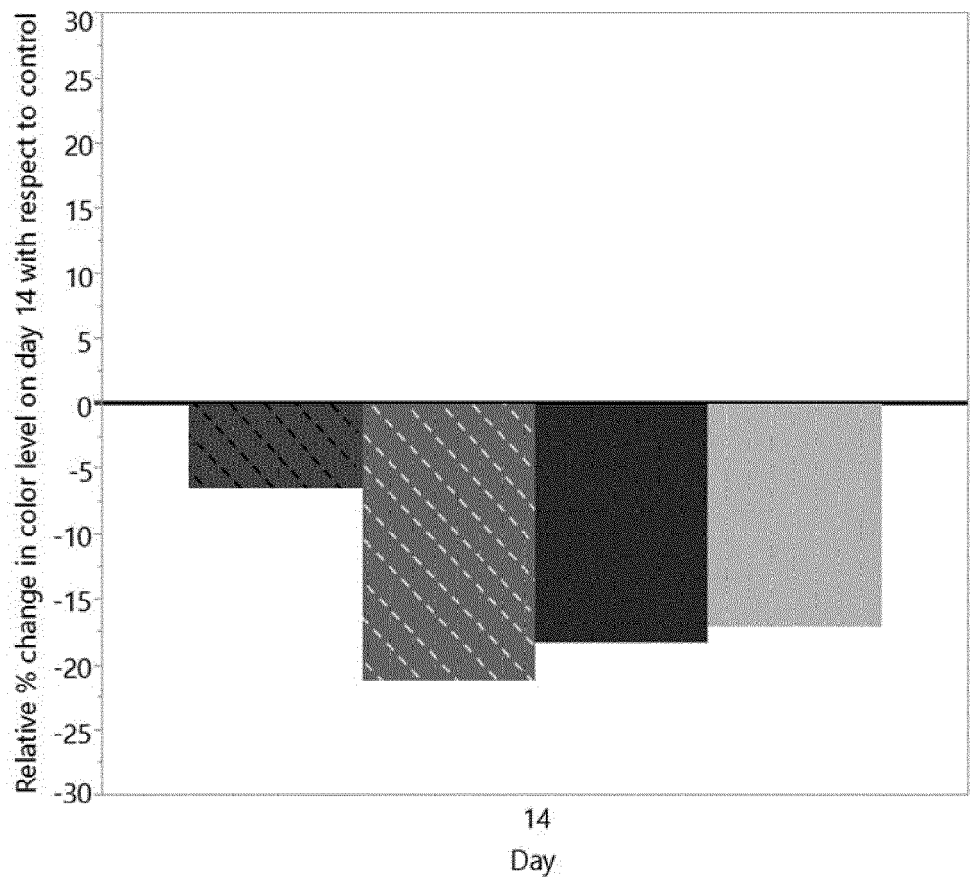
Overlay
■ 50% N-acetyl-cysteine 50% Cysteine Feed
▧ 50% N,N'-diacetyl cystine 50% Cysteine Feed
▨ 50% N,N'-diacetyl-L-cystine dimethylester 50% Cysteine Feed
▦ 50% S-Sulfocysteine 50% Cysteine Feed Figure 4 : Relative % change in acidic species level on day 14 with respect to control (100% Cysteine Feed)
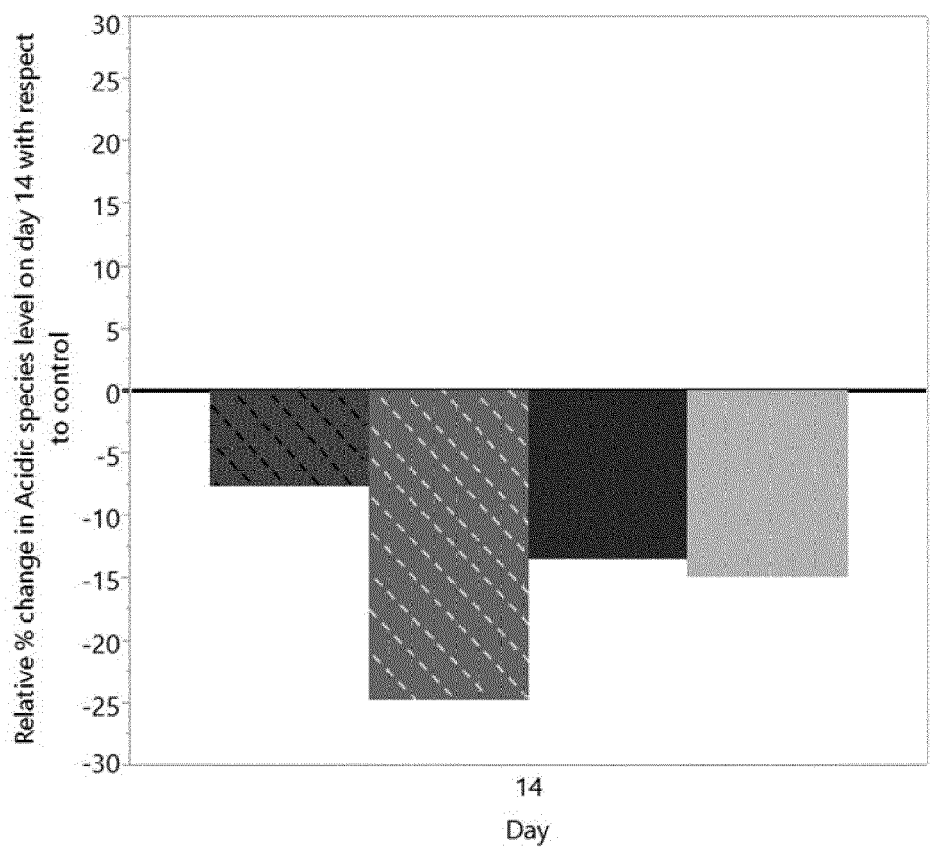
Overlay
- 50% N-acetyl-cysteine 50% Cysteine Feed
- 50% N,N'-diacetyl cystine 50% Cysteine Feed
- 50% N,N'-diacetyl-L-cystine dimethylester 50% Cysteine Feed
- 50% S-Sulfocysteine 50% Cysteine Feed Figure 5. Main charge species level on day 14
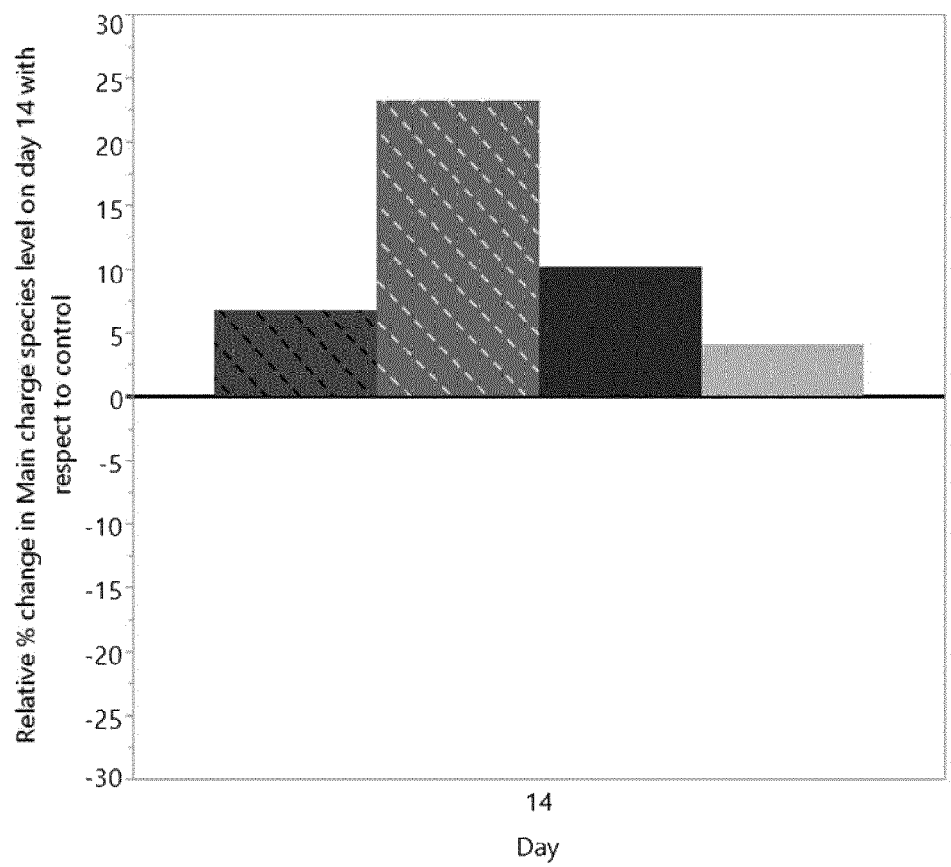
Overlay
- 50% N-acetyl-cysteine 50% Cysteine Feed
- 50% N,N'-diacetyl cystine 50% Cysteine Feed
- 50% N,N'-diacetyl-L-cystine dimethylester 50% Cysteine Feed
- 50% S-Sulfocysteine 50% Cysteine Feed Figure 6 : Viable cell concentration
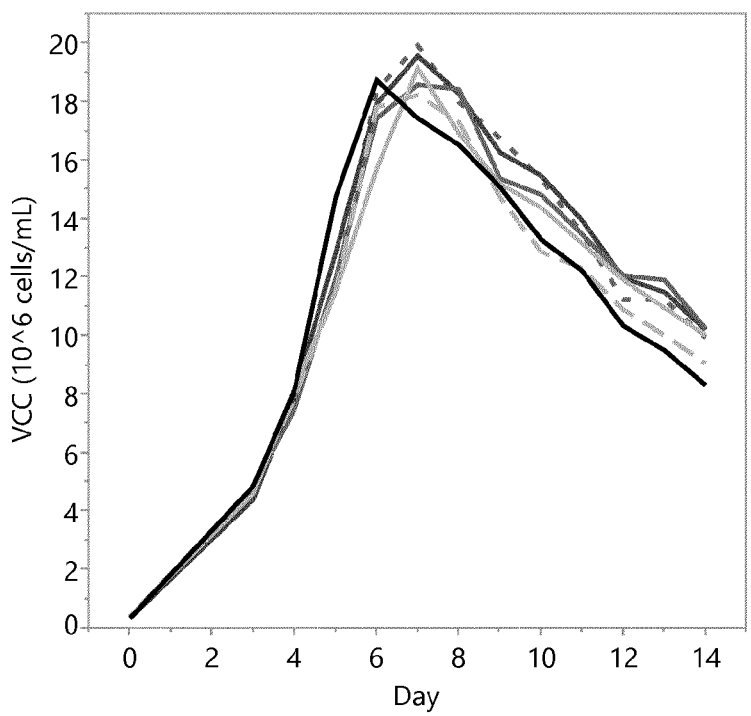
Overlay
— Control 100% Cysteine Feed n=2
····· 50% Cysteine Feed
━━ 50% N,N'-diacetyl cystine 50% Cysteine Feed
▬▬ 50% N,N'-diacetyl-L-cystine dimethylester 50% Cysteine Feed
───── 50% N-acetyl-cysteine 50% Cysteine Feed
── ── 50% S-Sulfocysteine 50% Cysteine Feed Figure 7 : Relative % change in Mab titer on day 14 with respect to control (100% Cysteine Feed)
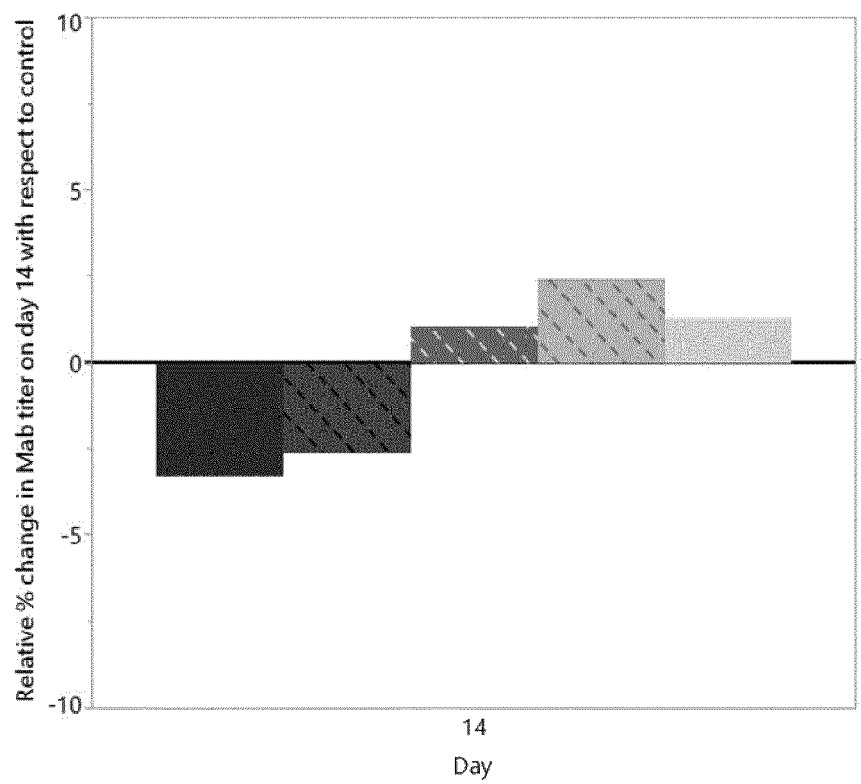
Overlay
- 50% Cysteine Feed
- 50% N,N'-diacetyl cystine 50% Cysteine Feed
- 50% N,N'-diacetyl-L-cystine dimethylester 50% Cysteine Feed
- 50% N-acetyl-cysteine 50% Cysteine Feed
- 50% S-Sulfocysteine 50% Cysteine Feed

Figure 8 : Relative % change in acidic species level on day 14 with respect to control (100% Cysteine Feed)
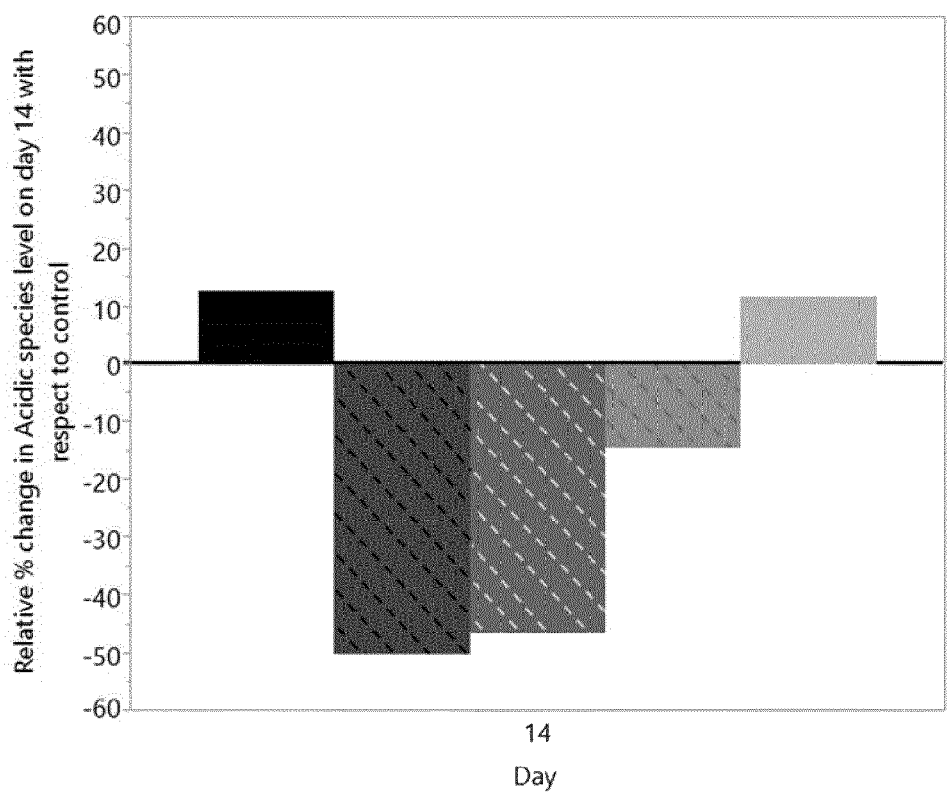
Overlay
- 50% Cysteine Feed
- 50% N,N'-diacetyl cystine 50% Cysteine Feed
- 50% N,N'-diacetyl-L-cystine dimethylester 50% Cysteine Feed
- 50% N-acetyl-cysteine 50% Cysteine Feed
- 50% S-Sulfocysteine 50% Cysteine Feed Figure 9 : Relative % change in main charge species level on day 14 with respect to control (100% Cysteine Feed)
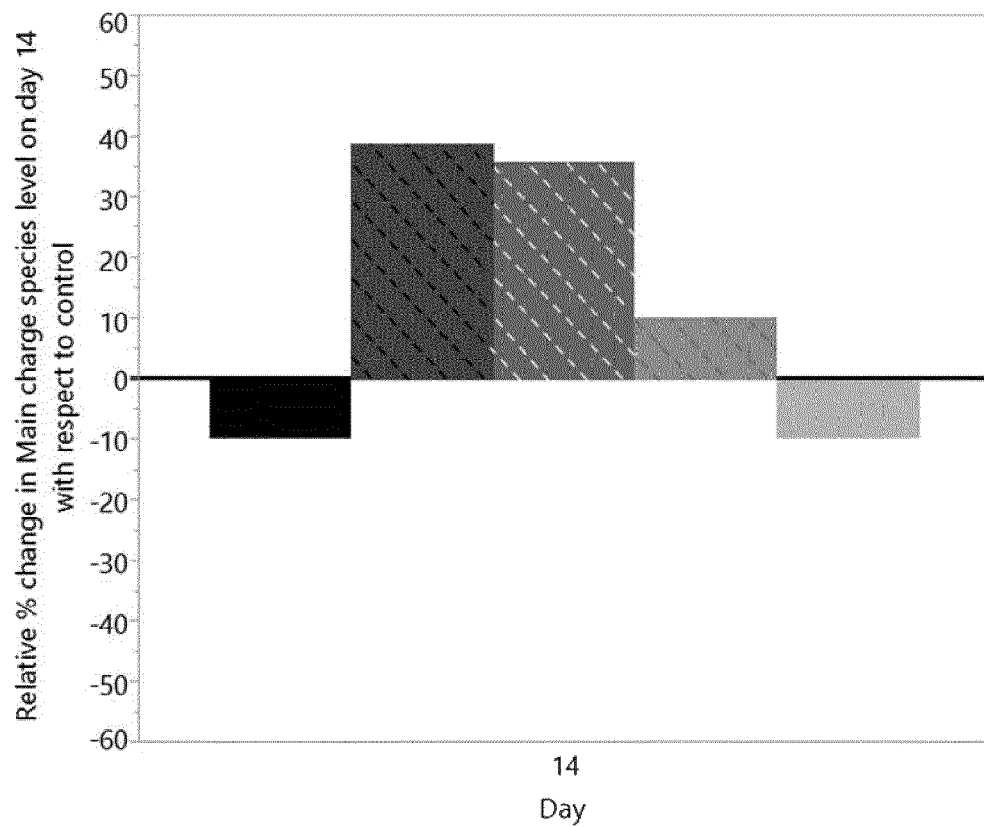
Overlay
- 50% Cysteine Feed
- 50% N,N'-diacetyl cystine 50% Cysteine Feed
- 50% N,N'-diacetyl-L-cystine dimethylester 50% Cysteine Feed
- 50% N-acetyl-cysteine 50% Cysteine Feed
- 50% S-Sulfocysteine 50% Cysteine Feed Figure 10 : Cell growth profile for cell line 1 in 2L bioreactor
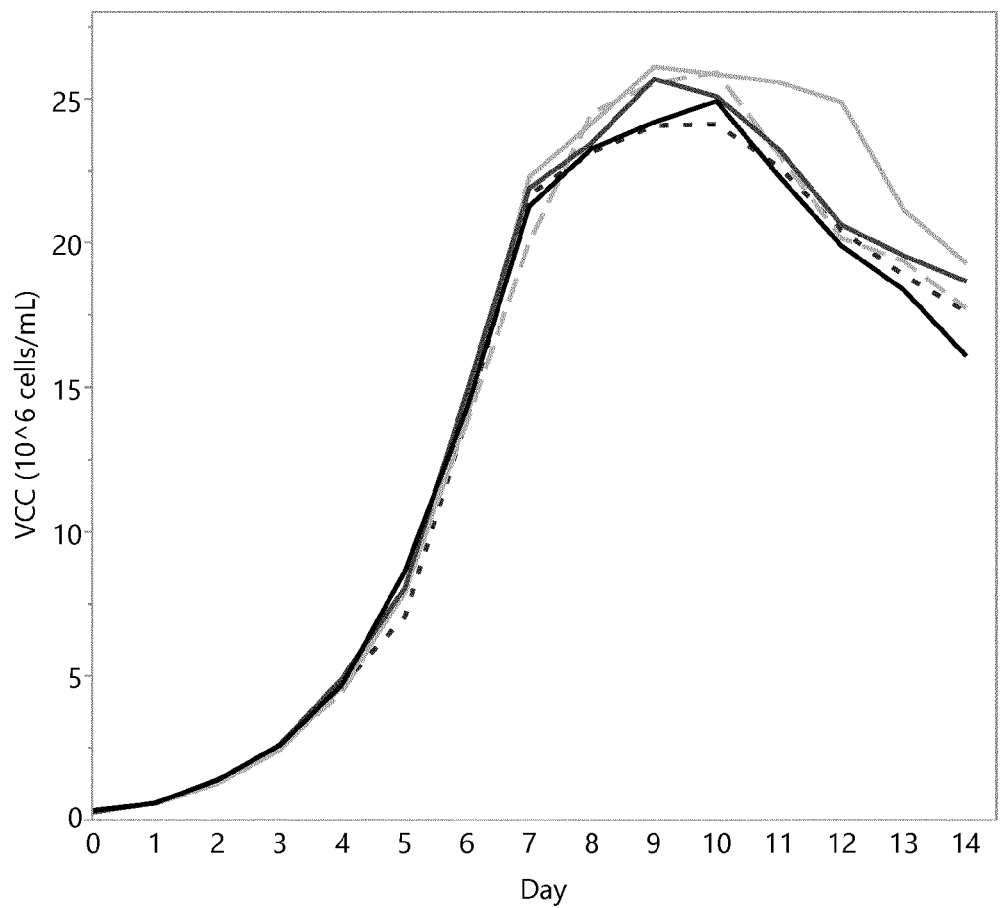
Overlay
— Control 100% Cysteine Feed
····· 50% Cysteine Feed
▬ 50% N-acetyl-cysteine 50% Cysteine Feed
▬ 50% N,N'-diacetyl cystine 50% Cysteine Feed
▬ ▬ 50% N,N'-diacetyl-L-cystine dimethylester 50% Cysteine Feed Figure 11 : Relative % change in Mab titer with respect to the control for cell line 1 in 2L Bioreactor
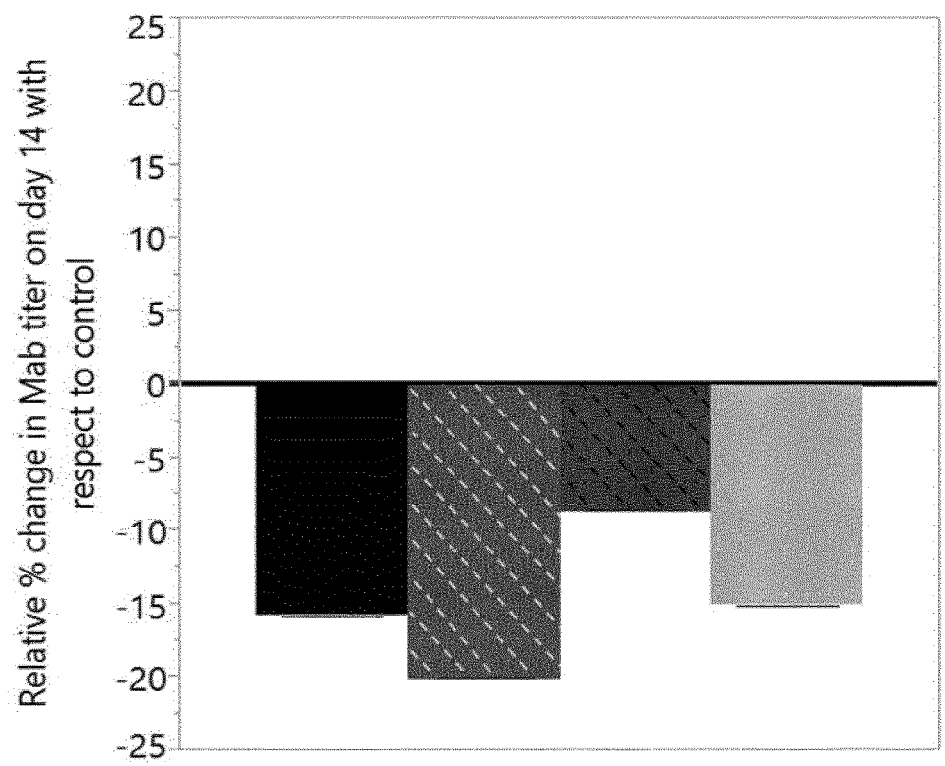
Overlay
- 50% Cysteine Feed
- 50% N,N'-diacetyl cystine 50% Cysteine Feed
- 50% N,N'-diacetyl-L-cystine dimethylester 50% Cysteine Feed
- 50% N-acetyl-cysteine 50% Cysteine Feed Figure 12 : Relative % change in acidic species level with respect to the control for cell line 1 in 2L bioreactor
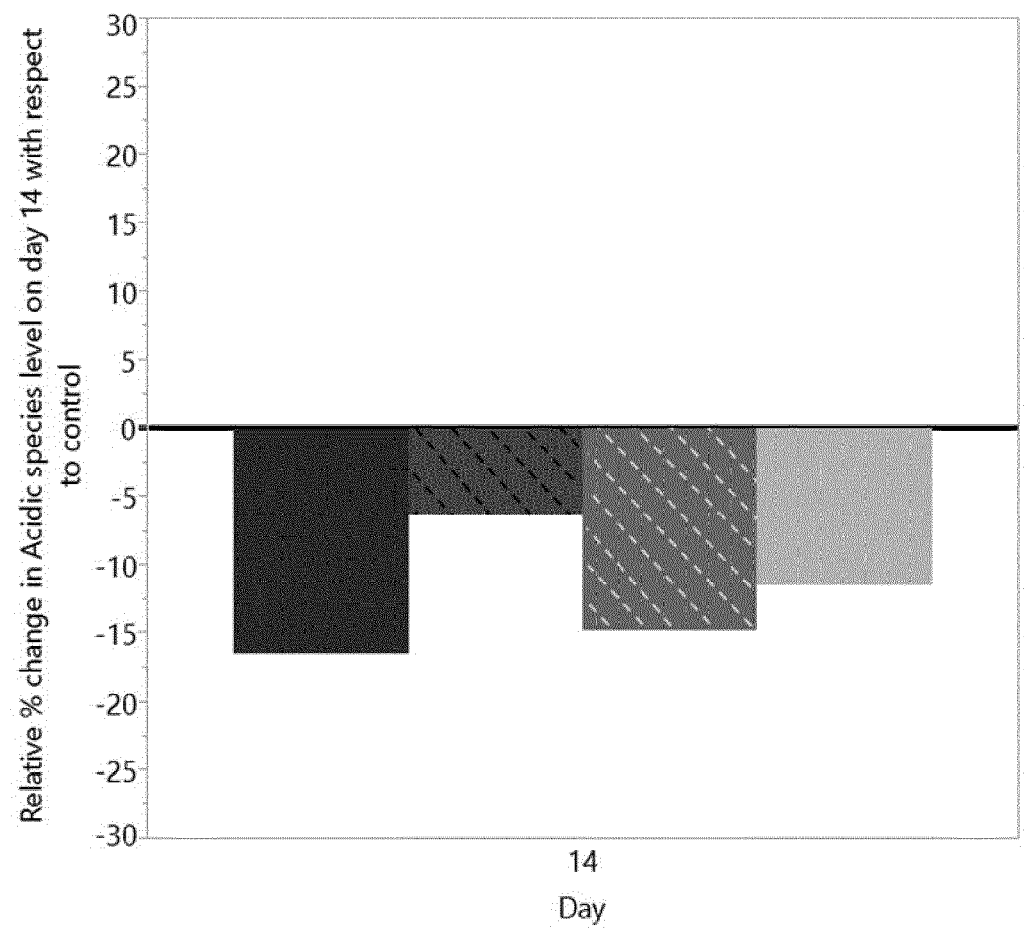
Overlay
- 50% Cysteine Feed
- 50% N,N'-diacetyl cystine 50% Cysteine Feed
- 50% N,N'-diacetyl-L-cystine dimethylester 50% Cysteine Feed
- 50% N-acetyl-cysteine 50% Cysteine Feed Figure 13 :Relative % change in main charge species level with respect to the control for cell line 1 in 2L bioreactor
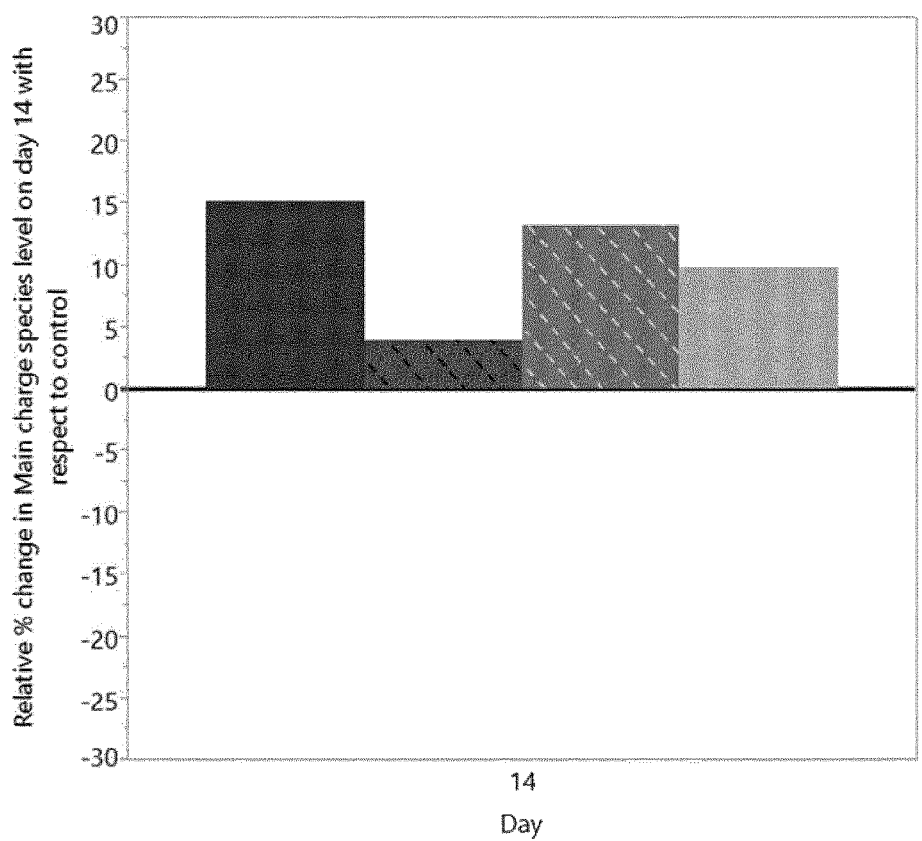
Overlay
- 50% Cysteine Feed
- 50% N,N'-diacetyl cystine 50% Cysteine Feed
- 50% N,N'-diacetyl-L-cystine dimethylester 50% Cysteine Feed
- 50% N-acetyl-cysteine 50% Cysteine Feed Figure 14 : Relative % change in color intensity (b* value) with respect to the control for cell line 1 in 2L bioreactor
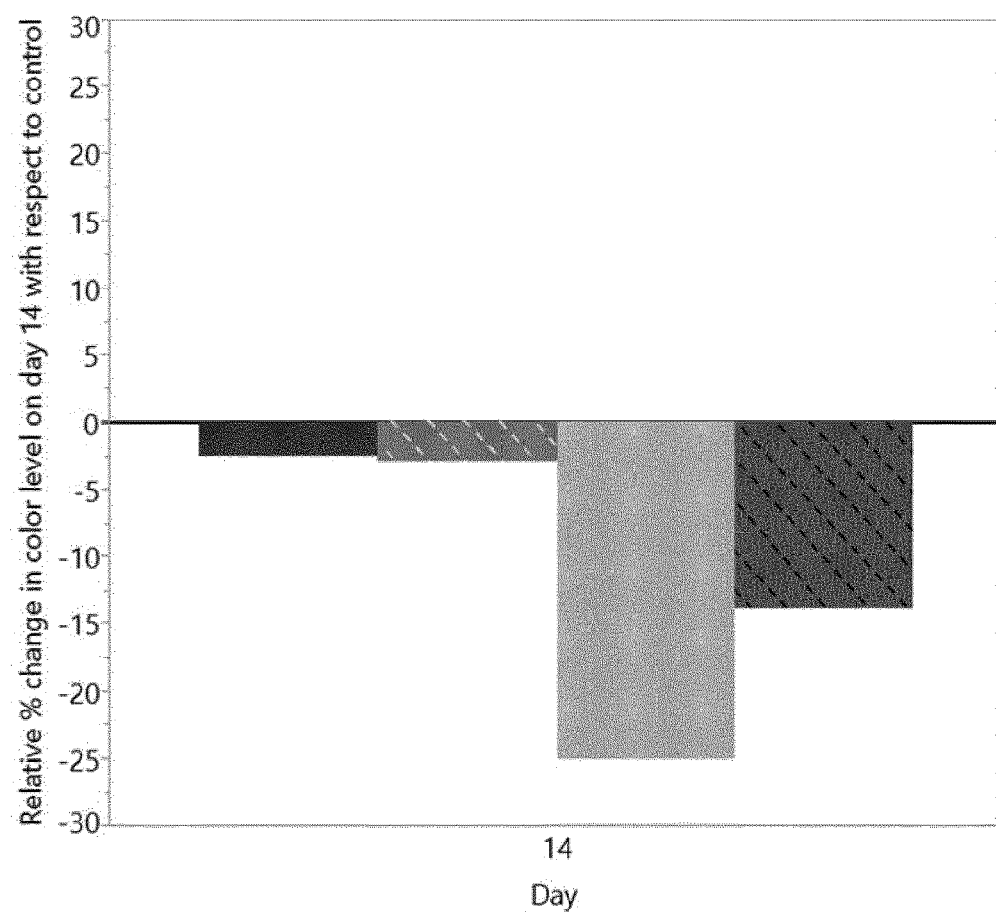
Overlay
- 50% Cysteine Feed
- 50% N,N'-diacetyl cystine 50% Cysteine Feed
- 50% N,N'-diacetyl-L-cystine dimethylester 50% Cysteine Feed
- 50% N-acetyl-cysteine 50% Cysteine Feed Figure 15 : Cell growth profile for cell line 2 in 2L bioreactor
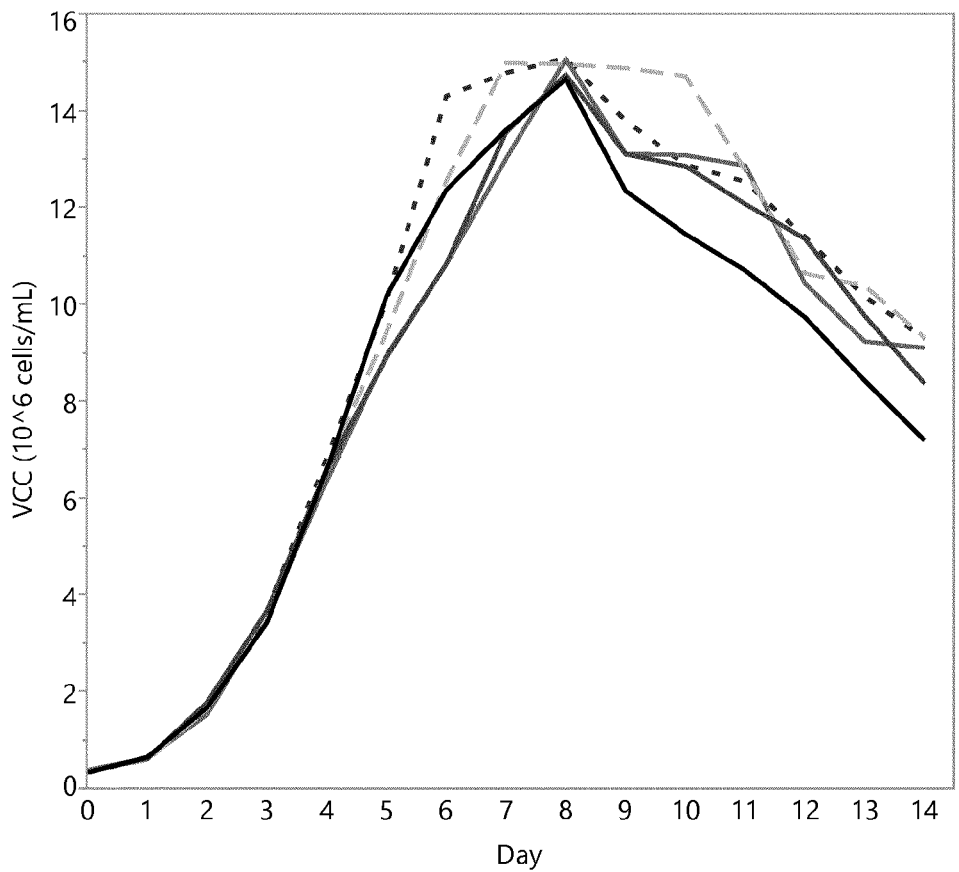
Overlay
— Control 100% Cysteine Feed
····· 50% Cysteine Feed
━━ 50% N,N'-diacetyl cystine 50% Cysteine Feed
━ ━ 50% N,N'-diacetyl-L-cystine dimethylester 50% Cysteine Feed
━━ 50% N-acetyl-cysteine 50% Cysteine Feed Figure 16 : Relative % change in Mab titer with respect to the control for cell line 2 in 2L Bioreactor
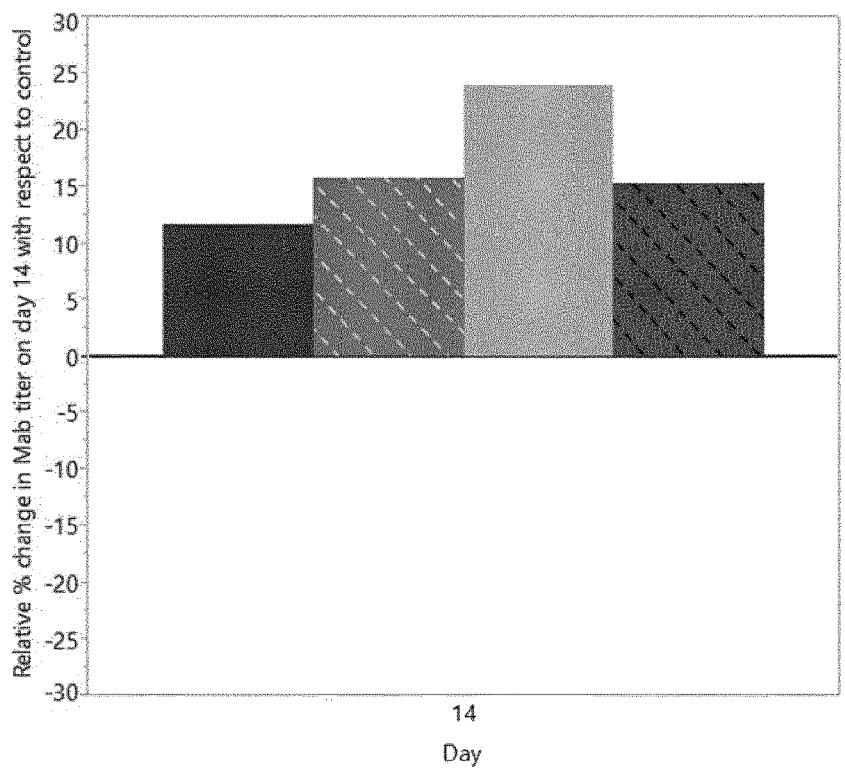
Overlay
- 50% Cysteine Feed
- 50% N-acetyl-cysteine 50% Cysteine Feed
- 50% N,N'-diacetyl cystine 50% Cysteine Feed
- 50% N,N'-diacetyl-L-cystine dimethylester 50% Cysteine Feed Figure 17 : Relative % change in acidic species level with respect to the control for cell line 2 in 2L bioreactor
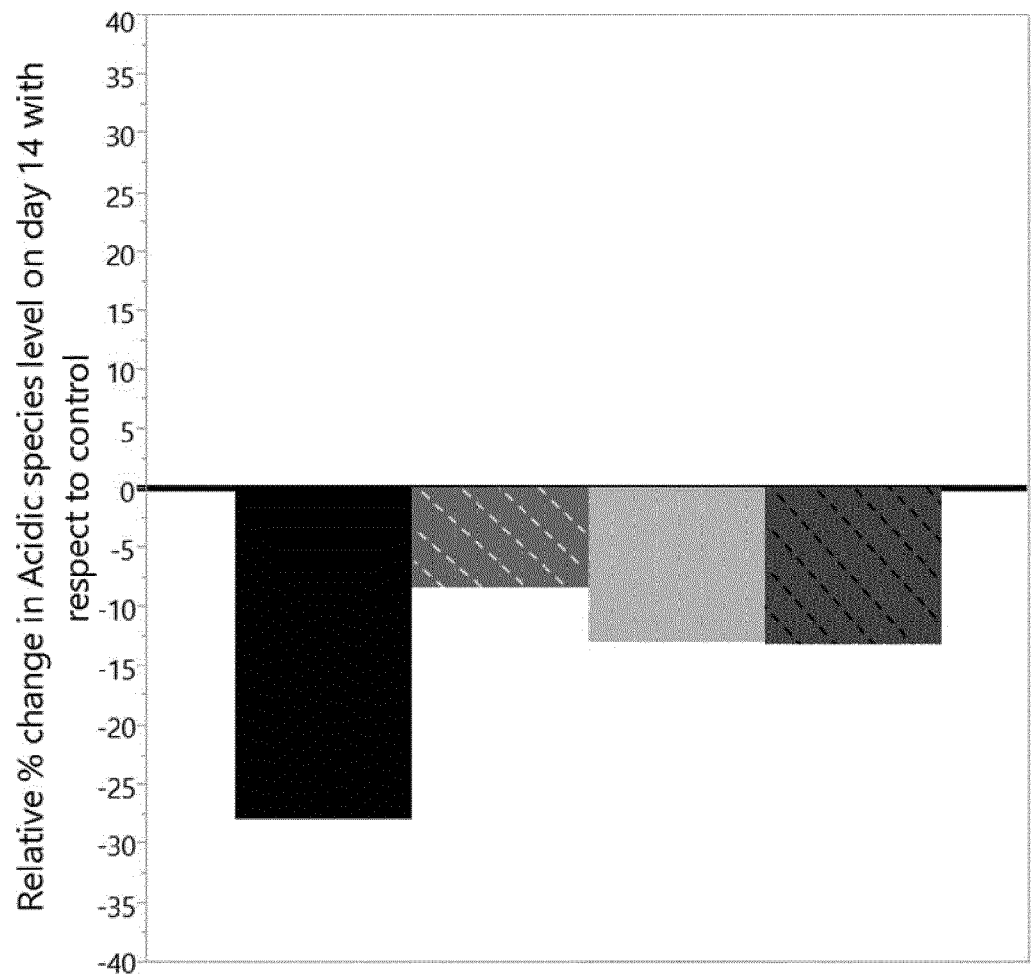
Overlay
- 50% Cysteine Feed
- 50% N-acetyl-cysteine 50% Cysteine Feed
- 50% N,N'-diacetyl cystine 50% Cysteine Feed
- 50% N,N'-diacetyl-L-cystine dimethylester 50% Cysteine Feed Figure 18: Relative % change in main charge species level with respect to the control for cell line 2 in 2L bioreactor
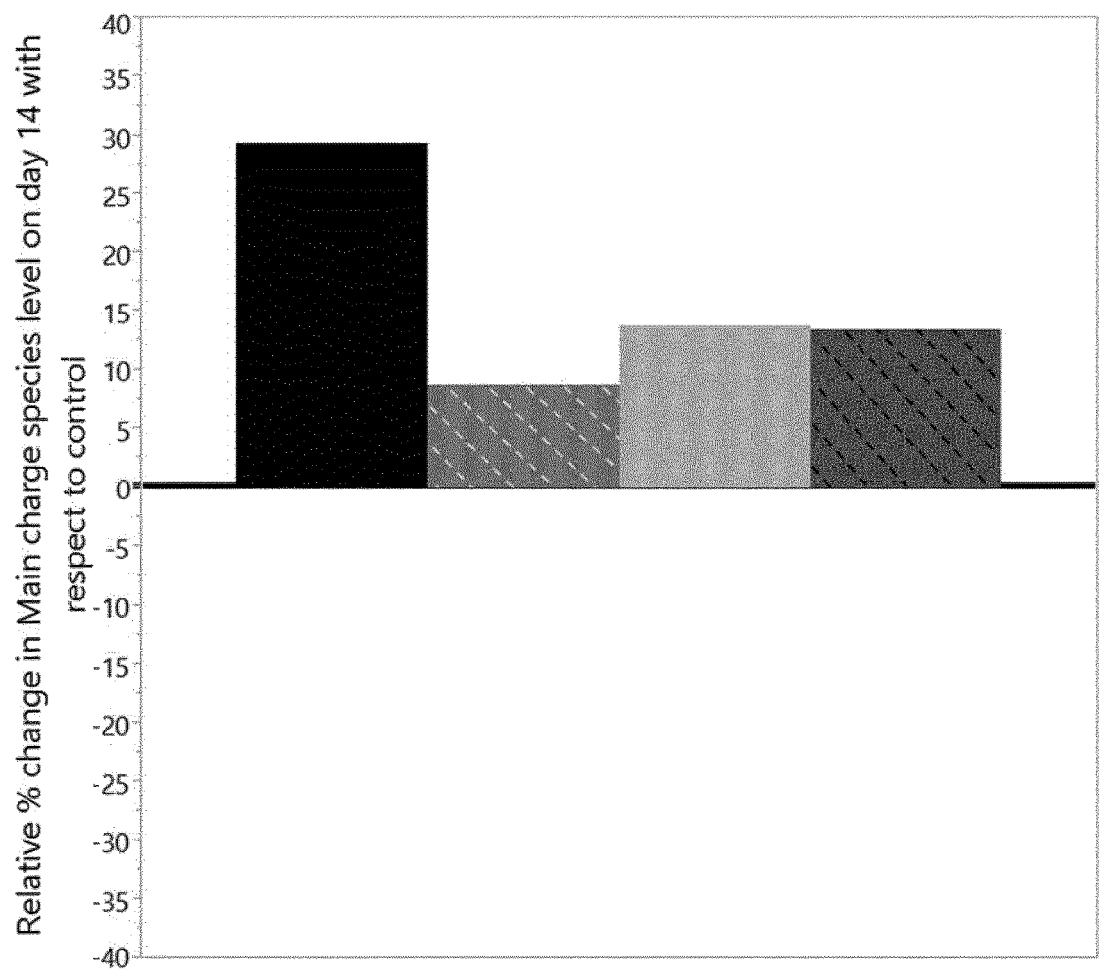
Overlay
- 50% Cysteine Feed
- 50% N-acetyl-cysteine 50% Cysteine Feed
- 50% N,N'-diacetyl cystine 50% Cysteine Feed
- 50% N,N'-diacetyl-L-cystine dimethylester 50% Cysteine Feed Figure 19 : Average cell growth profile from data sets 1 and 2 in 2L bioreactors (error bars = 1SD)
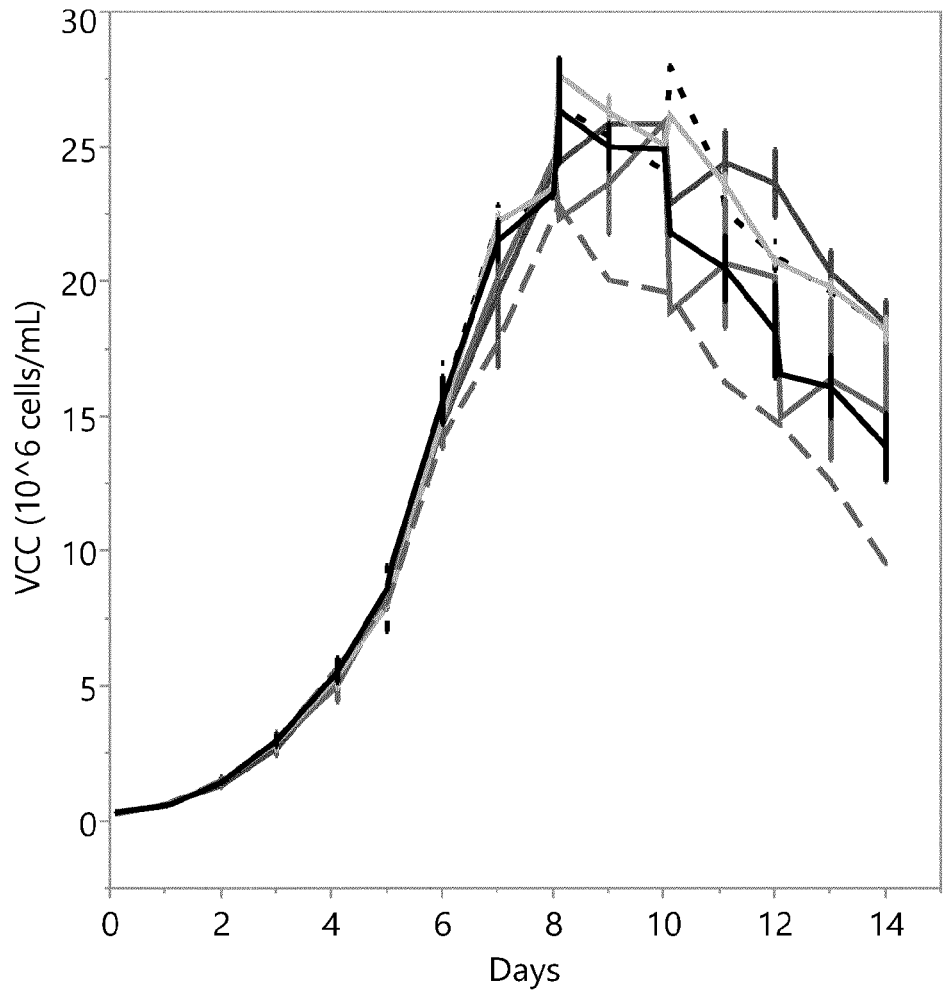
Overlay
····· 50% Cysteine Feed n=2
━ 50% N,N'-diacetyl cystine 50% Cysteine Feed n=2
━ 50% N,N'-diacetyl-L-cystine dimethylester 50% Cysteine Feed n=2
━ 50% N-acetyl-cysteine 50% Cysteine Feed n=2
━· 50% S-Sulfocysteine 50% Cysteine Feed
━ Control 100% Cysteine Feed Figure 20 : Relative % change in Mab titer with respect to the control. Data sets 1 and 2 average values (error bars = 1SD)
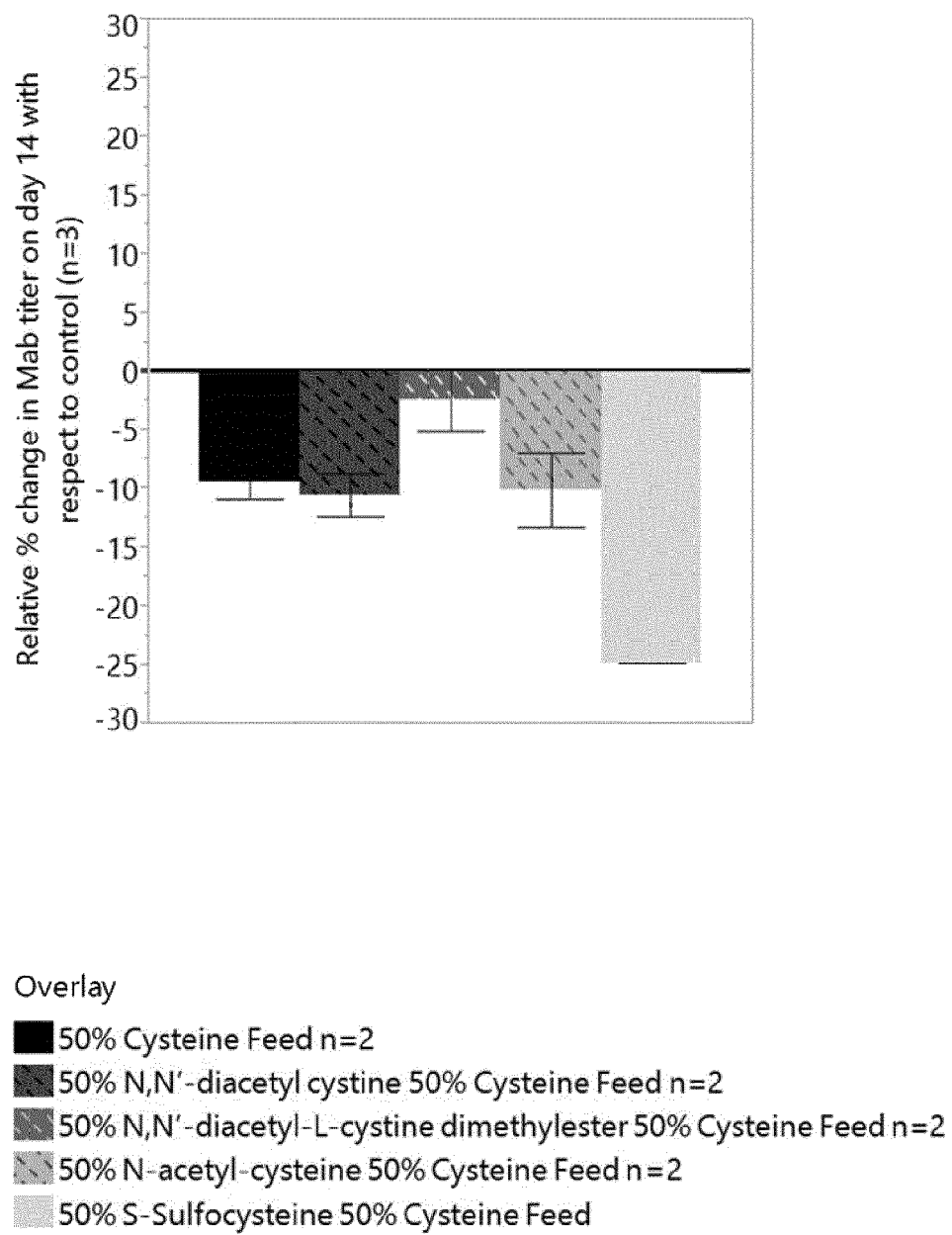
Overlay
- 50% Cysteine Feed n=2
- 50% N,N'-diacetyl cystine 50% Cysteine Feed n=2
- 50% N,N'-diacetyl-L-cystine dimethylester 50% Cysteine Feed n=2
- 50% N-acetyl-cysteine 50% Cysteine Feed n=2
- 50% S-Sulfocysteine 50% Cysteine Feed Figure 21 : Relative % change in acidic species level with respect to the control. Data sets 1 and 2 average values (error bars = 1SD)
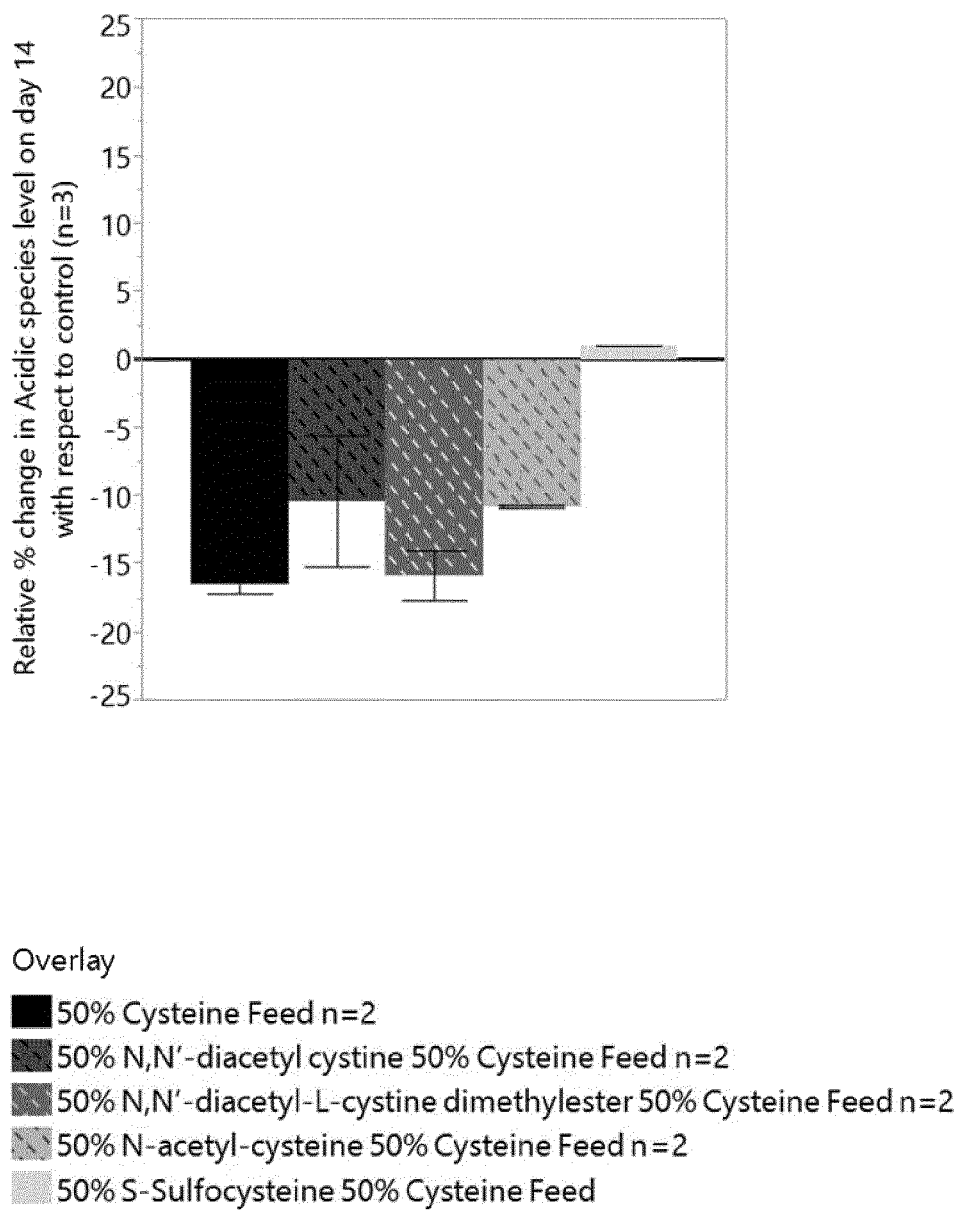
Overlay
- 50% Cysteine Feed n=2
- 50% N,N'-diacetyl cystine 50% Cysteine Feed n=2
- 50% N,N'-diacetyl-L-cystine dimethylester 50% Cysteine Feed n=2
- 50% N-acetyl-cysteine 50% Cysteine Feed n=2
- 50% S-Sulfocysteine 50% Cysteine Feed Figure 22 : Relative % change in main charge species level with respect to the control. Data sets 1 and 2 average values (error bars = 1SD)
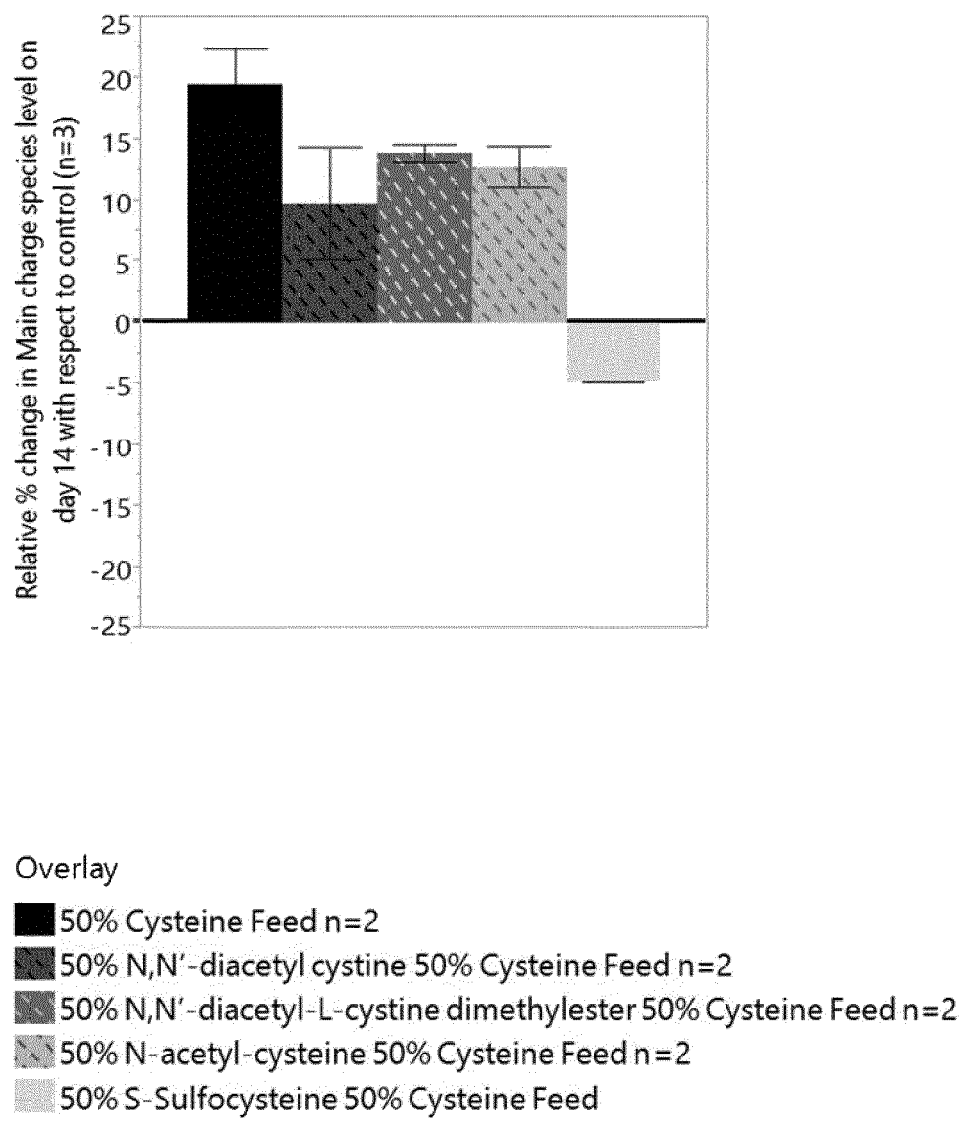
Overlay
- 50% Cysteine Feed n=2
- 50% N,N'-diacetyl cystine 50% Cysteine Feed n=2
- 50% N,N'-diacetyl-L-cystine dimethylester 50% Cysteine Feed n=2
- 50% N-acetyl-cysteine 50% Cysteine Feed n=2
- 50% S-Sulfocysteine 50% Cysteine Feed Figure 23 : Relative % change in color intensity (b* value) with respect to the control. Data sets 1 and 2 average values (error bars = 1SD)
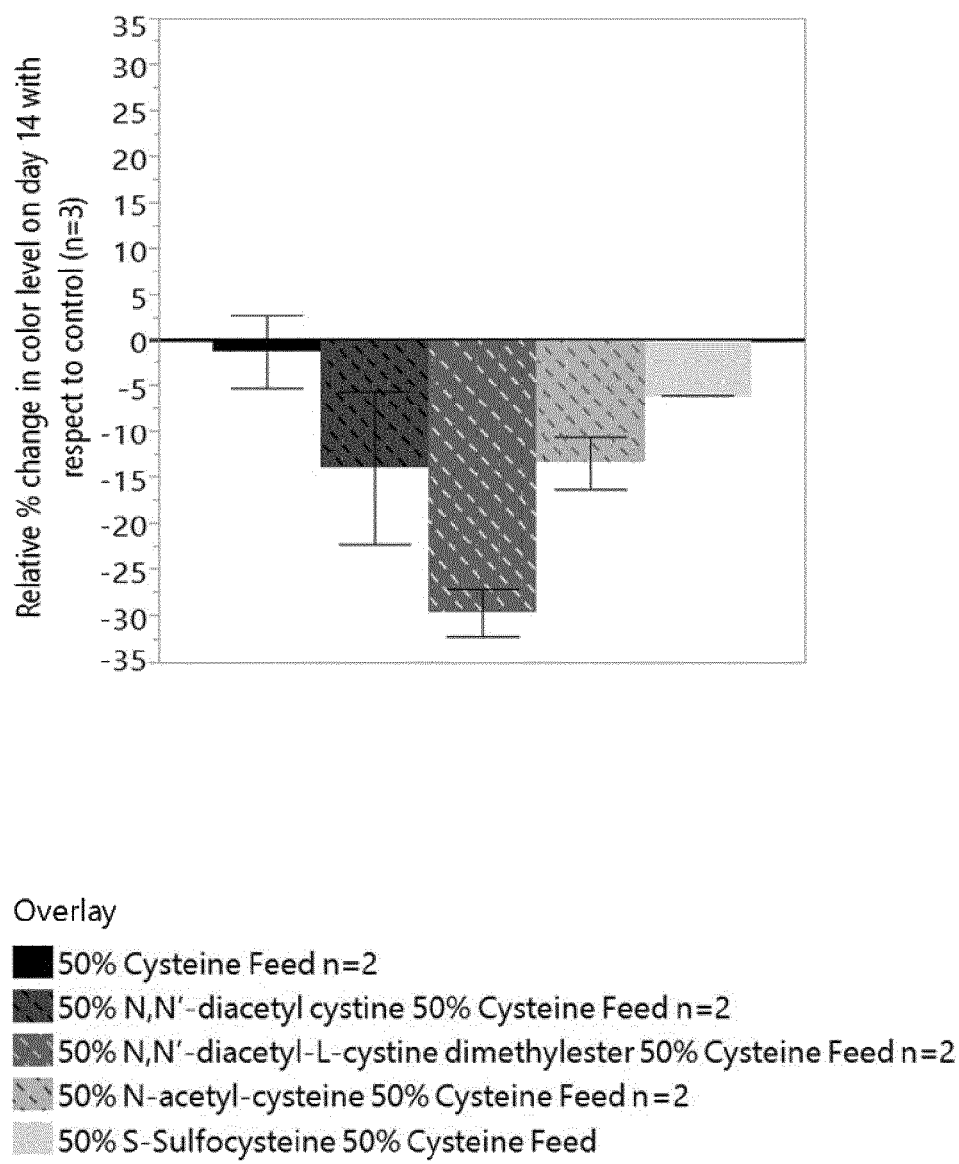
Overlay
- 50% Cysteine Feed n=2
- 50% N,N'-diacetyl cystine 50% Cysteine Feed n=2
- 50% N,N'-diacetyl-L-cystine dimethylester 50% Cysteine Feed n=2
- 50% N-acetyl-cysteine 50% Cysteine Feed n=2
- 50% S-Sulfocysteine 50% Cysteine Feed

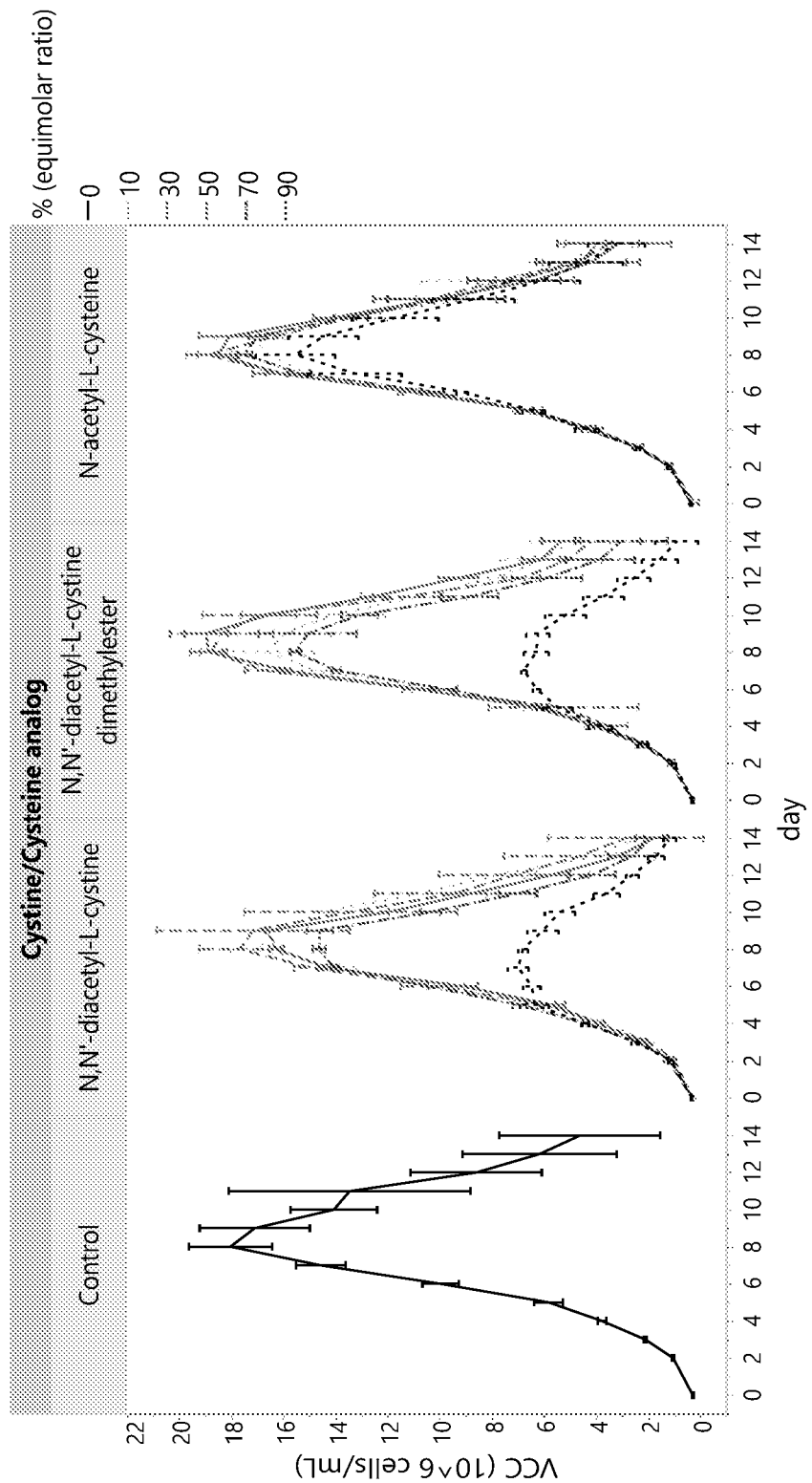
Figure 24 : Cell growth profile for cell line 1 in 15mL bioreactor.

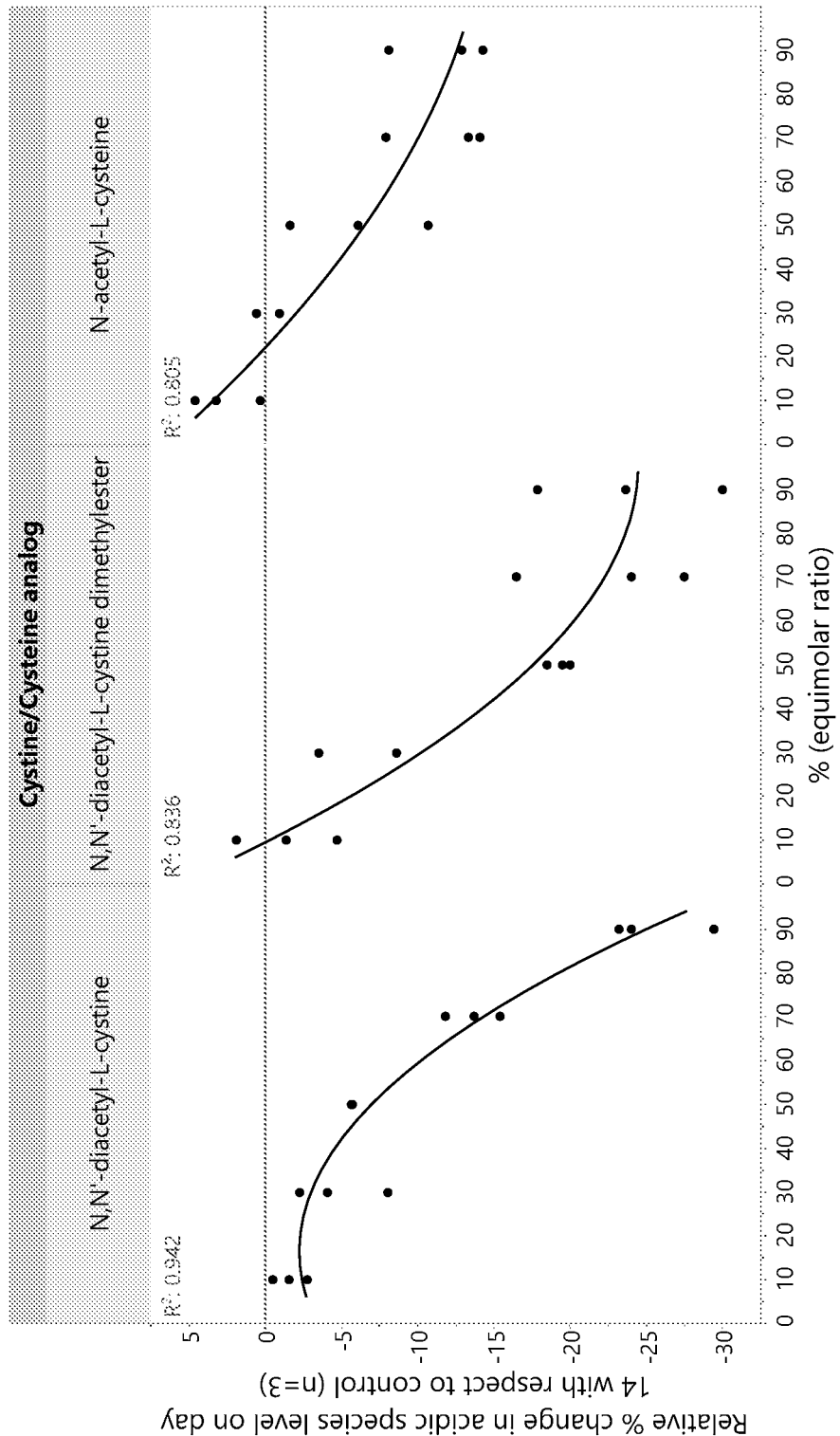
Figure 25 : Relative % change in acidic species level with respect to the control in response to different cysteine/cystine analog level.

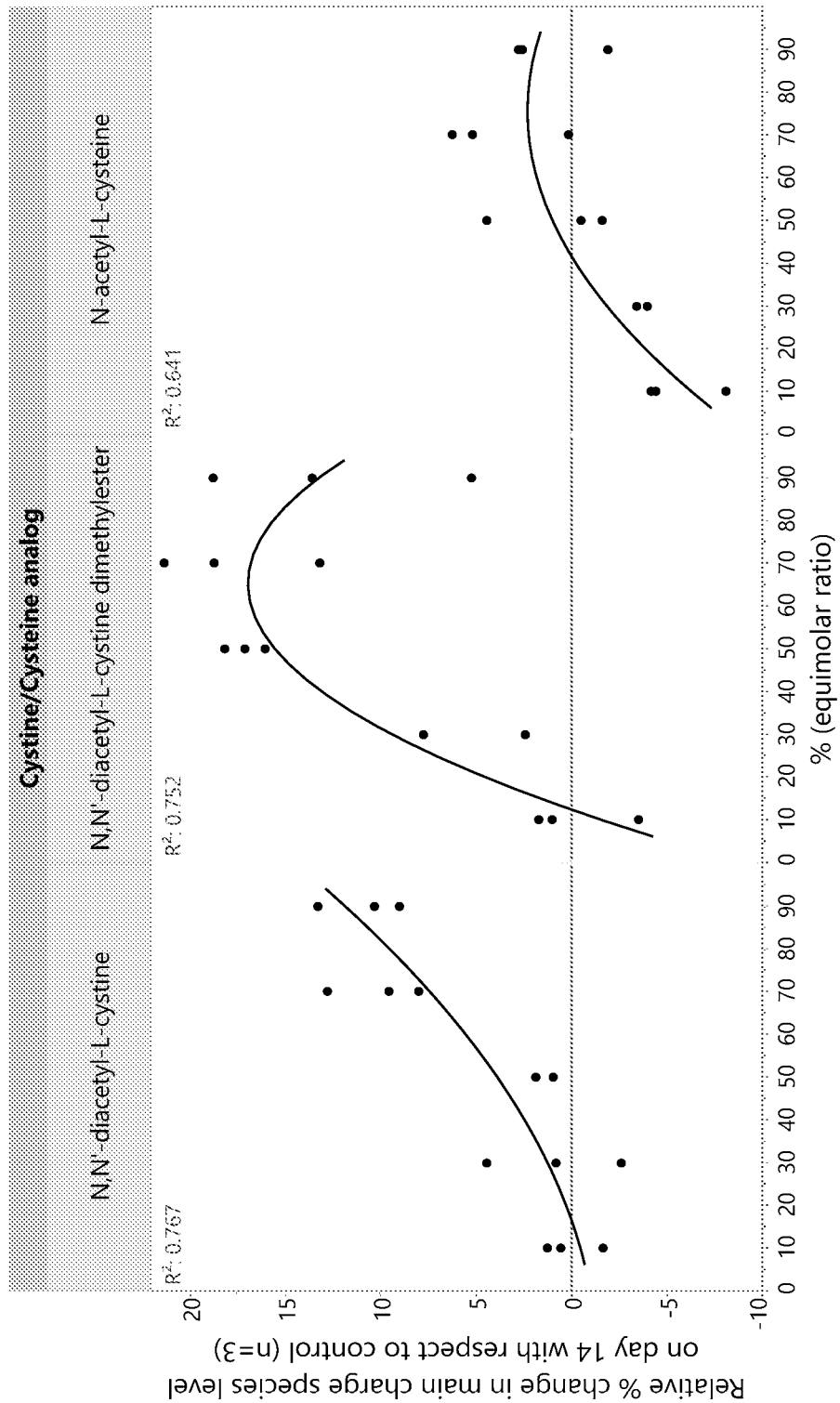
Figure 26: Relative % change in main charge species level with respect to the control in response to different cysteine/cystine analog level.

CELL CULTURE METHODS

CROSS-REFERENCE TO RELATED APPLICATION

This application is the U.S. national stage application of International Patent Application No. PCT/EP2018/083010, filed Nov. 29, 2018.

The Sequence Listing for this application is labeled "Seq-List.txt" which was created on Apr. 17, 2020 and is 11 KB. The entire content of the sequence listing is incorporated herein by reference in its entirety.

FIELD OF THE INVENTION

The present invention belongs to the field of the manufacture of recombinant proteins, in particular antibodies. More specifically, it relates to cell culture methods for producing recombinant proteins with reduced heterogeneity during commercial scale manufacturing.

BACKGROUND OF THE INVENTION

Development of recombinant proteins as therapeutic proteins, such as therapeutic antibodies, requires production of the recombinant proteins at an industrial scale. In order to achieve this, different expression systems, both prokaryotic and eukaryotic systems, may be employed. Over the past two decades, however, the majority of the therapeutic proteins approved as therapeutic have been manufactured through mammalian cell cultures and such systems remain the preferred expression systems for producing large quantity of recombinant proteins for human use.

Mammalian cell cultures, however, present significant challenges. The titer of recombinant protein produced is generally very low compared with other eukaryotic productions systems, such as those based on yeast and insect cells. Over the last 30 years, much effort has been dedicated to establishing the basic parameters of cell culture and recombinant protein expression with much focus of the research dedicated to reaching optimal cell growth through changes of the composition of the cell culture media (see e.g. Hecklau C., et al. J Biotech 218 (2016) 53-63; Zang Li. et al. Anal. Chem 83 (2011) 5422-5430) and operating conditions and, development of large bioreactors. For example, L-cysteine is one of the essential amino acids that is commonly added in media and feeds. Cysteine derivatives, such as S-Sulfocysteine and N-acetyl-cysteine, have been used to improve specific productivity in cell culture (Hecklau et al., supra; Oh et al. (2005) Biotechnol. Prog. 21:1154).

Whilst yield is still a very important aspect of mammalian cell culture, in recent years, the focus has shifted towards controlling product quality and process consistency at all stages of development and production scale. Therapeutic proteins produced by mammalian cell culture exhibit varying levels of heterogeneity. Such heterogeneity includes, but is not limited to, different glycosylation patterns, differences resulting from deamidation or oxidation, different charge or size variants. Heterogeneity of recombinant proteins may also lead to differences in product color, e.g. between different batches of the same protein manufactured by the same manufacturing process. Such heterogeneity and in particular differences in color, of the recombinant protein of interest, becomes more apparent when the therapeutic proteins are formulated at high concentrations. In recent years, there has been a steady trend toward subcutaneous delivery of therapeutic proteins which requires formulating therapeutic proteins at high concentrations. High concentrations have also been associated with increased aggregate levels (Purdie J., et al. Biotechnology Progress, 2016). Increased charge variants, such as increased levels of acidic species may affect protein stability (Banks D. D., et al. Journal of pharmaceutical sciences, 2009) whilst the color of the concentrated therapeutic protein may be more intense.

Cell culture conditions, such as the composition of the medium (Kshirsagar R., et al. Biotechnology and Bioengineering, 109:10, 2523-2532 (2012); US 2013/0281355; WO 2013/158275) and the growing conditions, including pH and temperature (U.S. Pat. No. 8,765,413) have been shown to impact the quality attributes of therapeutic proteins. Yet, there remains the need to provide further improved cell culture methods for the production of therapeutic proteins, and in particular, therapeutic antibodies with minimal heterogeneity.

SUMMARY OF THE INVENTION

The present invention addresses the above-identified need by adding cysteine/cystine analogs and/or partially replacing cysteine/cystine by cysteine/cystine analogs in the medium used for production of recombinant proteins in cell culture.

Accordingly, in a first aspect, the invention relates to a method for reducing the heterogeneity of a population of recombinant proteins produced in cell culture, said method comprising growing host cells producing a recombinant protein in a cell culture medium wherein the cell culture medium comprises one or more cysteine/cystine analogs.

In a second aspect, the invention relates to a method for producing a recombinant protein preparation comprising:
  (i) inoculating said host cells in a basal medium, wherein the basal medium optionally comprises an initial amount of:
    (a) cysteine/cystine analogs; and/or
    (b) cysteine and/or cystine,
  (ii) progressing the culture through a production phase wherein the recombinant protein is produced by the cells, wherein, during said production phase, the cell culture medium is supplemented with:
    (a) cysteine/cystine analogs; and/or
    (b) cysteine and/or cystine,
  wherein (a) and (b) may be added simultaneously or sequentially,
  wherein, when the contents of the basal medium and the total supplements added are added up, the molar ratio of (a) to (b) is between 1:18 and 18:1.

In a third aspect, the invention relates to A method for producing a recombinant protein preparation comprising:
  (i) inoculating said host cells in a basal medium, wherein the basal medium optionally comprises an initial amount of:
    (a) cysteine/cystine analogs; and/or
    (b) cysteine and/or cystine,
  (ii) progressing the culture through a production phase wherein the recombinant protein is produced by the cells, wherein, during said production phase, the cell culture medium is supplemented with:
    (a) cysteine/cystine analogs; and/or
    (b) cysteine and/or cystine,
  wherein (a) and (b) may be added simultaneously or sequentially,
  wherein, when the contents of the basal medium and the total supplements added are added up, the molar ratio of (a) to (b) is between 1:18 and 18:1.

In a further aspect, the invention relates to a recombinant protein preparation obtainable or obtained by the method according to the invention.

In an even further aspect, the invention relates to a cell culture medium suitable for culturing mammalian cells comprising N,N'-diacetyl-L-cystine-dimethylester.

BRIEF DESCRIPTION OF THE DRAWINGS

FIG. 1: Viable cell concentrations

FIG. 2: Relative % change in Mab titer on day 14 compared to control (100% Cysteine Feed)

FIG. 3: Relative % change in color intensity (b*value) level on day 14 compared to control (100% Cysteine Feed)

FIG. 4: Relative % change in acidic species level on day 14 compared to control (100% Cysteine Feed)

FIG. 5: Relative % change in main charge species level on day 14 compared to control (100% Cysteine Feed)

FIG. 6: Viable cell concentrations

FIG. 7: Relative % change in Mab titer on day 14 compared to control (100% Cysteine Feed)

FIG. 8: Relative % change in acidic species level on day 14 compared to control (100% Cysteine Feed)

FIG. 9: Relative % change in main charge species level on day 14 compared to control (100% Cysteine Feed)

FIG. 10: Cell growth profile for cell line 1 in 2 L bioreactor (viable cell concentrations)

FIG. 11: Relative % change in Mab titer compared to control for cell line 1 in 2 L bioreactor FIG. 12 Relative % change in acidic species level compared to control for cell line 1 in 2 L bioreactor FIG. 13: Relative % change in main charge species level compared to control for cell line 1 in 2 L bioreactor FIG. 14: Relative % change in color intensity (b* value) with respect to the control for cell line 1 in 2 L bioreactor FIG. 15: Cell growth profile for cell line 2 in 2 L bioreactor (viable cell concentrations)

FIG. 16: Relative % change in Mab titer compared to control for cell line 2 in 2 L bioreactor FIG. 17 Relative % change in acidic species level compared to control for cell line 2 in 2 L bioreactor FIG. 18: Relative % change in main charge species level compared to control for cell line 2 in 2 L bioreactor FIG. 19: Average cell growth profile from data sets 1 and 2 in 2 L bioreactors (error bars=1SD)

FIG. 20: Relative % change in Mab titer with respect to the control. Data sets 1 and 2 average values (error bars=1SD)

FIG. 21: Relative % change in acidic species level with respect to the control. Data sets 1 and 2 average values (error bars=1SD)

FIG. 22: Relative % change in main charge species level with respect to the control. Data sets 1 and 2 average values (error bars=1SD)

FIG. 23: Relative % change in color intensity (b* value) with respect to the control. Data sets 1 and 2 average values (error bars=1SD)

FIG. 24: Cell growth profile for cell line 1 in 15 mL bioreactor

FIG. 25: Relative % change in acidic species level with respect to the control in response to different cysteine/cystine analog level.

FIG. 26: Relative % change in main charge species level with respect to the control in response to different cysteine/cystine analog level.

DETAILED DESCRIPTION OF THE INVENTION

As described above, in a first aspect, the invention relates to a method for reducing the heterogeneity of a population of recombinant proteins produced in cell culture, said method comprising growing host cells producing a recombinant protein in a cell culture medium wherein the cell culture medium comprises one or more cysteine/cystine analogs.

The method of the invention particularly reduces coloration of recombinant proteins. Thus, in an independent aspect, the invention relates to a method for reducing coloration of a population of recombinant proteins produced in cell culture, said method comprising growing host cells producing a recombinant protein in a cell culture medium comprising one or more cysteine/cystine analogs.

In a further independent aspect, the invention relates to a method for producing a recombinant protein preparation comprising:
(i) inoculating said host cells in a basal medium, wherein the basal medium optionally comprises an initial amount of:
(a) cysteine/cystine analogs; and/or
(b) cysteine and/or cystine,
(ii) progressing the culture through a production phase wherein the recombinant protein is produced by the cells, wherein, during said production phase, the cell culture medium is supplemented with:
(a) cysteine/cystine analogs; and/or
(b) cysteine and/or cystine,
wherein (a) and (b) may be added simultaneously or sequentially,
wherein, when the contents of the basal medium and the total supplements added are added up, the molar ratio of (a) to (b) is between 1:18 and 18:1.

Heterogeneity

The invention is based on the finding that by adding cysteine/cystine analogs to the cell culture medium during the production phase in a process for manufacturing a recombinant protein, the heterogeneity of the recombinant polypeptides produced is reduced, without reducing the titer of the recombinant polypeptides at the end of the production.

The heterogeneity is preferably reduced with respect to:
a. color or intensity of color;
b. charge heterogeneity, preferably by reducing acidic peak group species (APG) and/or basic peak group species (BPG), whereby the main charge species does not decrease; and/or
c. amino acid oxidation, preferably methionine oxidation.

The term "heterogeneity" as used herein refers to differences between individual molecules, e.g. recombinant proteins, in a population of molecules produced by the same manufacturing process, or within the same manufacturing batch. Heterogeneity can result from incomplete or inhomogeneous modifications of the recombinant polypeptides, e.g. due to post-translational modifications of the polypeptide or to misincorporation during transcription or translation. Post-translational modifications can e.g. be the result of deamination reactions and/or oxidation reactions and/or covalent addition of small molecules such as glycation reactions and/or isomerization reactions and/or fragmentation reactions and/or other reactions and also include variation on the glycation patterns. The chemo-physical manifestation of such heterogeneity leads to various characteristics in the resulting recombinant polypeptide preparations which include, but are not limited to, charge variant profile, color or color intensity and molecular weight profile.

The terms "colored" or "color" when used herein indicate that a liquid solution, such as a concentrated protein preparation is not colorless. Following the definition of the European pharmacopeia, a solution is colorless if it has the appearance of water R or the solvent or is not more intensely colored than reference solution B9 (European pharmacopeia 2.2.2). A possible way to measure the reduction of color or intensity of color of recombinant proteins in cell culture, which can be used according to this invention, is by measuring relative spectral power distribution of CIE Standard Illuminant A Color intensity using a spectrophotometer by transmission, e.g. using UltrascanPro, and by comparing the data to the CIE (commission internationale de l'éclairage) scale for example by comparing the b*value.

The reduction of the charge heterogeneity, is preferably defined by measuring the acidic peak group (APG) species in the population of recombinant proteins produced in the cell culture. A possible way to measure the APG reduction, is by determining via Imaged Capillary Electrophoresis (e.g. PROTEINSIMPLE iCE3) the relative percentage of acidic (APG for Acidic Peak Group) isoforms of the recombinant proteins produced in a cell culture medium with or without the cysteine/cysteine analogs, which recombinant protein is at time of measurement preferably purified. When measuring the isoforms of the recombination proteins, besides the APG also the basic isoforms (Basic Peak Group (BPG)) and the main charge species are measured, wherein the main charge species represents the isoform of the recombinant protein that one wishes to obtain. It is preferred that when the APG is decreased, there is substantially no increase of the BPG. Preferably, when the APG is decreased, the main charge species level increases.

As described, the invention is related to manufacturing a recombinant protein wherein the heterogeneity of the recombinant polypeptides produced is reduced, without reducing the yield of the recombinant polypeptides. Preferably, the titer of the recombinant polypeptides is increased. According to the invention "the titer" is the concentration of the recombinant polypeptide at the end of the production phase, unless indicated differently.

Cysteine/Cystine Analogs

The term "cysteine analogs" or "cysteine derivatives" when used herein means one or more compounds which are structural analogs of cysteine, with the exception of cysteine itself.

The term "cystine analogs" or "cystine derivatives" when used herein means one or more compounds which are structural analogs of cysteine, with the exception of cystine itself.

The term "cysteine/cystine analogs" means "cysteine analogs" or "cystine analogs" or a mixture of "cysteine analogs" and "cystine analogs".

The term "cysteine/cystine derivatives" means "cysteine derivatives" or "cystine derivatives" or a mixture of "cysteine derivatives" and "cystine derivatives".

In one embodiment according to the present invention, the cysteine/cystine analogs comprise or consist of one or more compounds selected from the compounds represented by formula 1 and 2, and salts thereof:

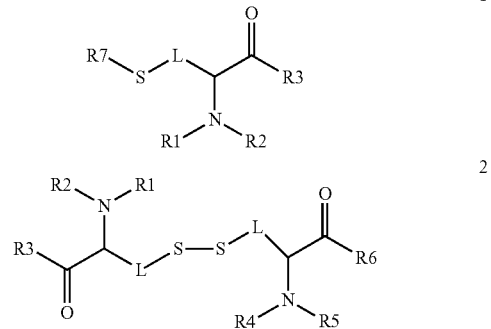

wherein,

R1, R2, R4 and R5 independently represent hydrogen, amino carbonyl, $C_{2-22}$acyl, $C_{1-22}$alkyl which group is optionally substituted by one or two substituents selected from hydroxy and $C_{1-22}$alkoxy; $C_{1-22}$ heteroalkyl, hydroxysulphonyl, $C_{1-22}$alkylsulphonyl, or $C_{5-22}$aryl sulphonyl;

R3 and R6 independently represent hydroxy; $NH_2$; $C_{1-22}$alkoxy wherein one or more carbons of the $C_{1-22}$ alkyl may be optionally replaced by an aryl or an heteroaryl; $C_{1-22}$ alkylamino which group is optionally substituted by a hydroxy or a $C_{1-22}$ alkyl; hydroxy amino; $C_{1-22}$ alkoxy amino; $C_{1-22}$ alkylamino wherein one or more carbons of the $C_{1-22}$alkyl are replaced by an aryl or an heteroaryl; $C_{1-22}$heteroalkylamino; di($C_{1-22}$ alkyl)amino which is optionally substituted by a hydroxy; di($C_{1-22}$alkyl)amino wherein one or more carbons of the $C_{1-22}$alkyl are replaced by an aryl or heteroaryl; or di($C_{1-22}$heteroalkyl)amino;

R7 represents hydrogen, phosphate or sulphate.

L represents an optionally substituted $C_{1-10}$alkylene chain; and with the proviso that the compound is not cysteine or cystine.

The term "$C_{1-22}$alkyl" as used herein refers to aliphatic hydrocarbon groups which may be straight or branched and may comprise 1 to 22 carbon atoms in the chain. Generally, $C_{1-22}$alkyl groups which may be present on the compounds of use in the invention include $C_{6-22}$ alkyl groups, $C_{12-22}$ alkyl groups, $C_{1-16}$ alkyl groups, $C_{1-10}$ alkyl groups and $C_{1-6}$ alkyl groups. Examples of $C_{12-22}$ alkyl groups include palmitinyl and stearyl.

The term "$C_{5-22}$aryl" as used herein, refers to an unsaturated aromatic carbocyclic group of from 5 to 22 carbon atoms having a single ring or multiple condensed rings. Generally, $C_{5-22}$ aryl groups which may be present on the compounds of use in the invention include $C_{5-14}$ aryl groups, suitably include $C_{5-10}$ aryl groups. Examples of $C_{5-22}$aryl groups are phenyl and naphtyl.

The term "$C_{5-22}$heteroaryl" as used herein represents aromatic carbocyclic groups of from 5 to 22 carbon atoms having a single ring or multiple condensed rings, wherein one or more of the said carbon atoms have been replaced by one or more heteroatoms selected from oxygen, sulphur and nitrogen. Generally, $C_{5-22}$ heteroaryl groups which may be present on the compounds of use in the invention include $C_{5-14}$ heteroaryl aryl groups, suitably include $C_{5-10}$ heteroaryl groups.

The term "$C_{2-22}$acyl" as used herein refers to a group represented by formula —(C=O)R wherein R represents a $C_{1-22}$ alkyl group as defined here above. Generally, $C_{2-22}$acyl groups which may be present on the compounds of use in the present invention include $C_{2-6}$acyl groups, $C_{6-22}$acyl groups, and $C_{12-22}$acyl groups. Examples of such $C_{2-6}$acyl are methyl carbonyl, ethyl carbonyl, and butyl carbonyl. Examples of $C_{12-22}$acyl groups include palmitinyl carbonyl and stearyl carbonyl.

The term "$C_{1-22}$alkoxy" as used herein refers to a group represented by formula —O—R, wherein R represents a $C_{1-22}$ alkyl group as defined here above. Generally, $C_{1-22}$alkoxy groups which may be present on the compounds of use in the present invention include $C_{1-6}$alkoxygroups $C_{6-22}$alkoxy groups and $C_{12-22}$alkoxy groups. Examples of $C_{1-6}$alkoxy groups are methoxy and ethoxy. Examples of $C_{12-22}$alkoxy groups include palmitinyloxy and stearyloxy.

The term "$C_{1-22}$heteroalkyl" as used herein refers to a $C_{1-22}$ alkyl as defined above wherein one or more carbon atoms are replaced by one or more oxygen or nitrogen atom. Generally, $C_{1-22}$heteroalkyl groups which may be present on the compounds of use in the present invention include $C_{1-6}$heteroalkyl groups, $C_{6-22}$heteroalkyl groups and $C_{12-22}$heteroalkyl groups. Examples of $C_{1-22}$heteroalkyl include oligomers of ethylene glycol.

The term "hydroxysulphonyl" as used herein refers to a group represented by formula —S(=O)$_2$—OH.

The term "$C_{1-22}$alkyl sulphonyl" as used herein refers to a group represented by formula —S(=O)$_2$—R, wherein R represents a $C_{1-22}$ alkyl group as defined here above. Generally, $C_{1-22}$ alkyl sulphonyl groups which may be present on the compounds of use in the present invention include $C_{1-6}$ alkyl sulphonyl groups and $C_{6-22}$ alkyl sulphonyl groups, $C_{12-22}$ alkyl sulphonyl groups. Examples of $C_{1-22}$alkyl sulphonyl include methyl sulphonyl, ethyl sulphonyl, and tert-butyl sulphonyl.

The term "$C_{5-22}$aryl sulphonyl" as used herein refers to a group represented by formula —S(=O)$_2$—R', wherein R' represents a $C_{5-22}$ aryl group as defined here above. Examples of $C_{5-22}$aryl sulphonyl include phenyl sulphonyl and tolyl sulphonyl.

The term "$C_{1-22}$ alkylamino" as used herein refers to a group represented by formula —NH—R, wherein R represents a $C_{1-22}$ alkyl group as defined here above. Generally, $C_{1-22}$alkylamino groups which may be present on the compounds of use in the present invention include $C_{1-6}$alkylamino groups, $C_{6-22}$alkylamino groups and $C_{12-22}$alkylamino groups. Examples of $C_{1-22}$alkyl amino include methylamino, ethylamino, and butylamino.

The term $C_{1-22}$ alkoxy amino as used herein refers to a group represented by formula —NH—OR wherein R represents a $C_{1-22}$ alkyl group as defined here above. Generally, $C_{1-22}$alkoxyamino groups which may be present on the compounds of use in the present invention include $C_{1-6}$alkoxyamino groups, $C_{6-22}$alkoxyamino groups and $C_{12-22}$alkoxyamino groups. Examples of $C_{1-22}$alkyl amino include methylamino, ethylamino, and butylamino.

The term "di($C_{1-22}$ alkyl)amino" as used herein refers to by formula —NRR' wherein R and R' represent independently a $C_{1-22}$ alkyl group as defined here above. Generally, di($C_{1-22}$ alkyl)amino groups which may be present on the compounds of use in the present invention include di($C_{1-6}$ alkyl)amino, di($C_{6-22}$ alkyl)amino and di($C_{12-22}$ alkyl) amino. Examples of di($C_{1-22}$alkyl) amino include dimethyl amino, (methyl)(ethyl)amino, diethyl amino, propyl amino and butyl amino.

The term "$C_{1-22}$heteroalkylamino" as used herein refers to a group represented by formula —NH—R, wherein R represents a $C_{1-22}$ heteroalkyl group as defined here above. Generally, $C_{1-22}$heteroalkylamino groups which may be present on the compounds of use in the present invention include $C_{1-6}$heteroalkylamino, $C_{6-22}$heteroalkylamino and $C_{12-22}$heteroalkylamino.

The term "di($C_{1-22}$heteroalkyl)amino" as used herein refers to by formula —NRR' wherein R and R' represent independently a $C_{1-22}$ heteroalkyl group as defined here above. Generally, di($C_{1-22}$ heteroalkyl)amino groups which may be present on the compounds of use in the present invention include di($C_{1-6}$ heteroalkyl)amino, di($C_{6-22}$ heteroalkyl)amino and di($C_{12-22}$ heteroalkyl)amino.

The term "$C_{1-10}$ alkylene chain" refers to a divalent straight or branched alkylene chain containing 1 to 10 carbon atoms. Typical examples of "$C_{1-10}$ alkylene chain" include methylene, ethylene, propylene and butylene.

The term "amino carbonyl" as used herein refers to a group represented by formula —CO—N(R$_a$R$_b$) wherein the carbon of —CO binds to nitrogen of the cysteine/cystine analog and wherein R$_a$ and R$_b$ independently from each other represents a $C_{1-22}$alkyl as defined above.

In one embodiment according to the present invention, the cysteine/cystine analogs are selected from cysteine analogs represented by formula 1, wherein R1, R2, R3, R4, R5, R6 R7 and L are as defined here above. In a particular aspect of this embodiment, R7 represents hydrogen.

In another embodiment according to the present invention, the cysteine/cysteine analogs are selected from cystine analogs represented by formula 2, wherein R1, R2, R3, R4, R5, R6, R7 and L are as defined here above.

Generally, R1, R2, R4 and R5 independently represent hydrogen, $C_{2-22}$acyl, $C_{1-22}$alkyl which group is optionally substituted by one or two substituents selected from hydroxy and $C_{1-22}$alkoxy; or $C_{1-22}$ heteroalkyl.

Generally, R3 and R6 independently represent hydroxy; NH$_2$; $C_{1-22}$alkoxy wherein one or more carbons of the $C_{1-22}$ alkyl may be optionally replaced by an aryl or an heteroaryl; $C_{1-22}$ alkylamino which group is optionally substituted by a hydroxy; or di($C_{1-22}$ alkyl)amino which is optionally substituted by a hydroxy.

Generally, R7 represents hydrogen.

Generally, L represents a $C_{1-4}$alkylene chain, optionally substituted, by one or more $C_{1-6}$ alkyl, preferably, two methyl groups.

Suitably, R1 represents hydrogen or $C_{2-22}$acyl. Typically, R1 represents hydrogen or $C_{2-6}$acyl. Illustratively, R1 represents hydrogen or acetyl. In a particular embodiment R1 represents hydrogen.

Suitably, R2 represents hydrogen or $C_{2-22}$ acyl. Typically, represents hydrogen or $C_{2-6}$acyl. Illustratively, R2 represents hydrogen or acetyl.

Suitably, R3 represents hydroxy or $C_{1-22}$alkoxy. Typically, R3 hydroxy or $C_{1-6}$alkoxy. Illustratively, R3 represents hydroxy or methoxy.

Suitably, R4 represents hydrogen or $C_{2-22}$ acyl. Typically, R4 represents hydrogen or $C_{2-6}$acyl. Illustratively, R4 represents hydrogen or acetyl. In a particular embodiment, R4 represents hydrogen.

Suitably, R5 represents hydrogen or $C_{2-22}$ acyl. Typically, R5 represents hydrogen or hydrogen or $C_{2-6}$acyl. Illustratively, R5 represents acetyl.

Suitably, R6 represents hydroxy or $C_{1-22}$alkoxy. Typically, R6 represents hydroxy or $C_{1-6}$alkoxy. Illustratively, R6 represents hydroxy or methoxy.

Suitably, L represents methylene or ethylene. Illustratively, L represents methylene.

In one embodiment, the cysteine/cystine analogs comprises one or more compounds selected from the compounds represented by formula 1, and salts thereof, wherein L, R1, R2, R3 and R7 areas defined above,
with the provisos
(i) that if one of the R1 or R2 groups, represents, $C_{6-22}$acyl, $C_{6-22}$alkyl which group is optionally substituted by one or two substituents selected from hydroxy and $C_{1-22}$alkoxy; $C_{6-22}$ heteroalkyl, hydroxysulphonyl, $C_{6-22}$alkylsulphonyl, or $C_{5-22}$aryl sulphonyl; then the remaining R1 or R2 group represents independently hydrogen, amino carbonyl, $C_{2-6}$acyl, $C_{1-6}$alkyl which group is optionally substituted by one or two substituents selected from hydroxy and $C_{1-6}$alkoxy; $C_{1-6}$ heteroalkyl, hydroxysulphonyl, $C_{1-6}$alkylsulphonyl, or $C_{5-10}$aryl sulphonyl; and R3 represents hydroxy; $NH_2$; $C_{1-6}$alkoxy wherein one or more carbons of the $C_{1-22}$ alkyl may be optionally replaced by an aryl or an heteroaryl; $C_{1-6}$ alkylamino which group is optionally substituted by a hydroxy or a $C_{1-6}$ alkyl; hydroxy amino; $C_{1-6}$ alkoxy amino; $C_{1-6}$ alkylamino wherein one or more carbons of the $C_{1-6}$alkyl are replaced by an aryl or an heteroaryl; $C_{1-6}$heteroalkylamino; di($C_{1-6}$ alkyl)amino which is optionally substituted by a hydroxy; di($C_{1-6}$alkyl) amino wherein one or more carbons of the $C_{1-6}$alkyl are replaced by an aryl or heteroaryl; or di($C_{1-6}$heteroalkyl) amino; and (ii) that if R3 represents $C_{6-22}$alkoxy wherein one or more carbons of the $C_{6-22}$ alkyl may be optionally replaced by an aryl or an heteroaryl; $C_{6-22}$ alkylamino which group is optionally substituted by a hydroxy or a $C_{1-22}$ alkyl; hydroxy amino; $C_{6-22}$ alkoxy amino; $C_{6-22}$ alkylamino wherein one or more carbons of the $C_{1-22}$alkyl are replaced by an aryl or an heteroaryl; $C_{6-22}$heteroalkylamino; di($C_{6-22}$ alkyl)amino which is optionally substituted by a hydroxy; di($C_{6-22}$alkyl) amino wherein one or more carbons of the $C_{6-22}$alkyl are replaced by an aryl or heteroaryl; or di($C_{6-22}$heteroalkyl) amino, then R1 and R2 independently represents hydrogen, amino carbonyl, $C_{2-6}$acyl, $C_{1-6}$alkyl which group is optionally substituted by one or two substituents selected from hydroxy and $C_{1-6}$alkoxy; $C_{1-6}$ heteroalkyl, hydroxysulphonyl, $C_{1-6}$alkylsulphonyl, or $C_{5-10}$aryl sulphonyl.

In one embodiment, the cysteine/cystine analogs comprise or consist of the compound represented by formula 2, and salts thereof, wherein L, R1, R2, R3, R4, R5, R6 and R7 are as defined above, with the provisos:

(i) that if one of the of R1 and R2 groups represents $C_{6-22}$acyl, $C_{6-22}$alkyl which group is optionally substituted by one or two substituents selected from hydroxy and $C_{1-22}$alkoxy; $C_{6-22}$ heteroalkyl, hydroxysulphonyl, $C_{6-22}$alkylsulphonyl, or $C_{5-22}$aryl sulphonyl; and if one of the R4 and R5 groups represents $C_{6-22}$acyl, $C_{6-22}$alkyl which group is optionally substituted by one or two substituents selected from hydroxy and $C_{1-22}$alkoxy; $C_{6-22}$ heteroalkyl, hydroxysulphonyl, $C_{6-22}$alkylsulphonyl, or $C_{5-22}$aryl sulphonyl, then the remaining R1, R2, R4, or R5 groups independently represent hydrogen, amino carbonyl, $C_{2-6}$acyl, $C_{1-6}$alkyl which group is optionally substituted by one or two substituents selected from hydroxy and $C_{1-6}$alkoxy; $C_{1-6}$ heteroalkyl, hydroxysulphonyl, $C_{1-6}$alkylsulphonyl, or $C_{5-10}$aryl sulphonyl; and R3 and R6 independently represents hydroxy; NH2; $C_{1-6}$alkoxy wherein one or more carbons of the $C_{1-22}$ alkyl may be optionally replaced by an aryl or an heteroaryl; $C_{1-6}$ alkylamino which group is optionally substituted by a hydroxy or a $C_{1-6}$ alkyl; hydroxy amino; $C_{1-6}$ alkoxy amino; $C_{1-6}$ alkylamino wherein one or more carbons of the $C_{1-6}$alkyl are replaced by an aryl or an heteroaryl; $C_{1-6}$heteroalkylamino; di($C_{1-6}$ alkyl)amino which is optionally substituted by a hydroxy; di($C_{1-6}$alkyl)amino wherein one or more carbons of the $C_{1-6}$alkyl are replaced by an aryl or heteroaryl; or di($C_{1-6}$heteroalkyl)amino;

(ii) that if only if one of R1, R2, R4 and R5 groups independently represent $C_{6-22}$acyl, $C_{6-22}$alkyl which group is optionally substituted by one or two substituents selected from hydroxy and $C_{1-22}$alkoxy; $C_{6-22}$ heteroalkyl, hydroxysulphonyl, $C_{6-22}$alkylsulphonyl, or $C_{5-22}$aryl sulphonyl; then one of R3 and R6 may r represent $C_{6-22}$alkoxy wherein one or more carbons of the $C_{1-22}$ alkyl may be optionally replaced by an aryl or an heteroaryl; $C_{6-22}$ alkylamino which group is optionally substituted by a hydroxy or a $C_{1-22}$ alkyl; $C_{6-22}$ alkoxy amino; $C_{6-22}$ alkylamino wherein one or more carbons of the $C_{1-22}$alkyl are replaced by an aryl or an heteroaryl; $C_{6-22}$heteroalkylamino; di($C_{6-22}$ alkyl)amino which is optionally substituted by a hydroxy; di($C_{6-22}$alkyl)amino wherein one or more carbons of the $C_{6-22}$alkyl are replaced by an aryl or heteroaryl; or di($C_{6-22}$heteroalkyl) amino;

(iii) that if none of the R1, R2, R4 and R5 groups represents $C_{6-22}$acyl, $C_{6-22}$alkyl which group is optionally substituted by one or two substituents selected from hydroxy and $C_{1-22}$alkoxy; $C_{6-22}$ heteroalkyl, hydroxysulphonyl, $C_{6-22}$alkylsulphonyl, or $C_{5-22}$aryl sulphonyl; then R3 and R6 may both represent independently $C_{6-22}$alkoxy wherein one or more carbons of the $C_{1-22}$ alkyl may be optionally replaced by an aryl or an heteroaryl; $C_{6-22}$ alkylamino which group is optionally substituted by a hydroxy or a $C_{1-22}$ alkyl; $C_{6-22}$ alkoxy amino; $C_{6-22}$ alkylamino wherein one or more carbons of the $C_{1-22}$alkyl are replaced by an aryl or an heteroaryl; $C_{6-22}$heteroalkylamino; di($C_{6-22}$ alkyl)amino which is optionally substituted by a hydroxy; di($C_{6-22}$alkyl)amino wherein one or more carbons of the $C_{6-22}$alkyl are replaced by an aryl or heteroaryl; or di($C_{6-22}$heteroalkyl)amino.

The present invention also includes within its scope salts of cysteine/cystine analogs of formula 1 and 2.

Salts according to the invention may be formed by reaction of a hydroxy group present on the cysteine/cystine analogs. Such salts include alkali metal salts, for example sodium, potassium or lithium salts; alkali earth metal salts, for example magnesium or calcium salts; ammonium salts, for example tetra alkyl or aryl ammonium salts; sulphonium salts, for example trialkyl or aryl sulphonium; and phosphonium salts, for example tetra alkyl or aryl phosphonium salts.

Alternatively, such salts may be formed by reaction of an amino group present on the cysteine/cysteine analogs. Such salts typically result from the reaction of the amino group with an inorganic acid or an organic acid and include mono- or di-HCl salts, $H_2SO_4$ salts, $H_3PO_4$ salts, acetate and fumarate.

Suitably, the cysteine/cystine analogs as defined here above have the same chirality as L-cysteine.

In a particular embodiment of the present invention the cysteine/cysteine analogs are selected from N,N'-diacetyl-L-cystine-dimethylester, N-Acetyl-L-cysteine and N,N'-Diacetyl-L-cystine.

In a particular aspect of this embodiment, the cysteine/cystine analogs consists of, N,N'-diacetyl-L-cystine-dimethylester represented by formula 2a ((Ac-Cys-OMe)$_2$.

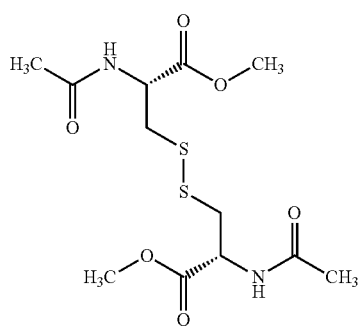

Cysteine/cysteine analogs according to the present invention may be commercially available or may be synthesized from L-cysteine or L-cystine by methods known to the skilled in the art.

Cell Culture

As it will be apparent from the description of the invention hereinafter, in most embodiments of the method of the invention, the cell culture medium is supplemented with cysteine and/or cystine, i.e. such supplementation may be performed with:
cysteine; or
cystine; or
cysteine and cystine.

Cysteine and cystine in the cell culture medium are in constant equilibrium wherein two molecules of cysteine oxidize into a molecule of cystine and reduce back to two molecules of cysteine.

The term "cell culture" or grammatical variations thereof includes, but it is not limited to, a plurality of host cells, preferably mammalian host cells, suitably engineered and/or manipulated to express (i.e. to produce) one or more recombinant polypeptides maintained or grown in cell culture medium for a particular period of time, e.g. the production phase.

The term "production phase" according to the present invention comprises that stage of cell culturing during the process for manufacturing a recombinant protein when the cells express (i.e. produce) the recombinant polypeptide(s). The production phase begins when the titer of the desired product increases and ends with harvest of the cells or the cell culture fluid or supernatant. Typically, at the beginning of the production phase, the cell culture is transferred to a production vessel, such as a bioreactor. Harvest is the step during which the cell culture fluid is removed from the e.g. production vessel, in order for the recombinant protein e.g. the recombinant antibody, to be recovered and purified in subsequent steps.

Preferred host cells are mammalian host cells, most preferably Chinese Hamster Ovary (CHO) cells. Mammalian cells, and in particular CHO cells, may be cultured in any medium that will support their growth and expression of the recombinant polypeptide, preferably the medium is a medium that is free of animal-derived products such as animal serum and peptone. There are different cell culture media available to the person skilled in the art, each medium comprising different combinations of vitamins, amino acids, hormones, growth factors, ions, buffers, nucleosides, glucose or an equivalent energy source, present at appropriate concentrations to enable cell growth and protein production. Suitable media have e.g. been described in WO98/08934 and US2006/0148074 (both incorporated herein in their entirety). Further suitable commercially available media that could be used in the present invention or be modified to fulfill the cysteine/cysteine analog and/or cysteine and/or cystine requirements include, but are not limited to, AmpliCHO CD medium, Dynamis™ Medium, EX-CELL® Advanced™ CHO Fed-batch System, CD FortiCHO™ medium, CP OptiCHO™ medium, Minimum Essential Media (MEM), BalanCD® CHO Growth A Medium, ActiPro™ medium, DMEM—Dulbecco's Modified Eagle Medium and RPMI-1640 medium.

In a preferred embodiment of the method of the invention, wherein said cell culture medium comprises:
(a) cysteine/cystine analogs; and
(b) cysteine and/or cystine,
wherein the molar ratio of (a) to (b) is between 1:18 and 18:1.

Preferably, said molar ratio of (a) to (b) is between 1:15 and 15:1, e.g. between 1:12 and 12:1, such as between 1:10 and 10:1, e.g. between 1:8 and 8:1, such as between 1:6 and 6:1, e.g. between 1:4 and 4:1, such as between 1:3 and 3:1, e.g. between 1:2 and 2:1, such as between 1.5:1 and 1:1.5, e.g. a molar ratio of 1:1.

Referred to the above preferred embodiment, it is noted that a skilled person knows that the ratio of (a) and (b) depends on whether the dimer form or the monomer form is taken as a reference point. Since cysteine and cystine in the cell culture medium are in constant equilibrium the ratio is considered relative to the cysteine equivalent, wherein it is assumed that all the cystine is in its reduced form. The following table gives as example how the ratio differs depending whether a cysteine analog or a cystine analog is taken into account.

| Molar ratio cysteine analog:cysteine | Molar ratio cystine analog:cysteine |
|---|---|
| 18:1 | 9:1 |
| 12:1 | 6:1 |
| 1:1 | 1:2 |
| 1:2 | 1:1 |
| 1:6 | 1:3 |
| 1:12 | 1:6 |
| 1:18 | 1:9 |

In another preferred embodiment, the method comprises the steps of:
(i) inoculating said host cells in a basal medium, wherein the basal medium optionally comprises an initial amount of:
(a) cysteine/cystine analogs; and/or
(b) cysteine and/or cystine,
(ii) progressing the culture through a production phase wherein the recombinant protein is produced by the cells, wherein, during said production phase, the cell culture medium is supplemented with:
(a) cysteine/cystine analogs; and/or
(b) cysteine and/or cystine,
wherein (a) and (b) may be added simultaneously or sequentially,
wherein, when the contents of the basal medium and the total supplements added are added up, the molar ratio of (a) to (b) is between 1:18 and 18:1.

Preferably, in the above-mentioned embodiments, said molar ratio of (a) to (b) is between 1:15 and 15:1, e.g. between 1:12 and 12:1, such as between 1:10 and 10:1, e.g. between 1:8 and 8:1, such as between 1:6 and 6:1, e.g.

between 1:4 and 4:1, such as between 1:3 and 3:1, e.g. between 1:2 and 2:1, such as between 1.5:1 and 1:1.5, e.g. a molar ratio of 1:1.

Referred to the above preferred embodiment, it is noted that a skilled person knows that the ratio of (a) and (b) depends on whether the dimer form or the monomer form is taken as a reference point. Since cysteine and cystine in the cell culture medium are in constant equilibrium the ratio is considered relative to the cysteine equivalent, wherein it is assumed that all the cystine is in its reduced form.

In a preferred embodiment according to the method of the invention, said cell culture medium comprises:
(a) cysteine/cystine analogs; and
(b) cysteine and/or cystine,
wherein, the molar amount of (a) is from 10 to 90 percent in view of the total molar amount of (a) and (b), wherein in case a cysteine analog is used, the molar amount of (b) is calculated in view of cysteine equivalents; and
wherein in case a cystine analog is used, the molar amount of (b) is calculated in view of cystine equivalents.

In the above embodiment, the molar amount of (a) in view of the total molar amount of (a) and (b) is preferably from 20 to 90 percent; such as from 30 to 90 percent, e.g. from 40 to 90 percent or e.g. from 50 to 90 percent, such as from 20 to 80 percent; such as from 30 to 80 percent, e.g. from 40 to 80 percent or e.g. from 50 to 80 percent, such as from 20 to 70 percent, from 30 to 70 percent, e.g. from 40 to 70 percent or e.g. from 50 to 70 percent.

Particularly preferred is wherein the cystine analog is N,N'-diacetyl-L-cystine-dimethylester or N,N'-Diacetyl-L-cystine, wherein the molar amount (a) in view of the total molar amount of (a) and (b) is from 20 to 90 percent, more preferably from 30 to 90 percent, such as from 20 to 70 percent, e.g. from 30 to 70 percent, or wherein the cysteine analog is N-Acetyl-L-cysteine, wherein the molar amount (a) in view of the total molar amount of (a) and (b) is from 50 to 90 percent, preferably form 50 to 80 percent, more preferably from 50 to 70 percent.

In another embodiment, the method comprises the steps of:
(i) inoculating said host cells in a basal medium, wherein the basal medium optionally comprises an initial amount of:
(a) cysteine/cystine analogs; and/or
(b) cysteine and/or cystine,
(ii) progressing the culture through a production phase wherein the recombinant protein is produced by the cells, wherein, during said production phase, the cell culture medium is supplemented with:
(a) cysteine/cystine analogs; and/or
(b) cysteine and/or cystine,
wherein (a) and (b) may be added simultaneously or sequentially,
wherein, when the contents of the basal medium and the total supplements added are added up, the molar amount of (a) in view of the total molar amount of (a) and (b) is from 10 to 90 percent, wherein in case a cysteine analog is used, the molar amount of (b) is calculated in view of cysteine equivalent; and
wherein in case a cystine analog is used, the molar amount of (b) is calculated in view of cystine equivalent.

In the above embodiment, the molar amount of (a) in view of the total molar amount of (a) and (b) is preferably from 20 to 90 percent; such as from 30 to 90 percent, e.g. from 40 to 90 percent or e.g. from 50 to 90 percent, such as from 20 to 80 percent; from 30 to 80 percent, e.g. from 40 to 80 percent or e.g. from 50 to 80 percent, such as from 20 to 70 percent, from 30 to 70 percent, e.g. from 40 to 70 percent or e.g. from 50 to 70 percent.

Particularly preferred is wherein the cystine analog is N,N'-diacetyl-L-cystine-dimethylester or N,N'-Diacetyl-L-cystine, wherein the molar amount (a) in view of the total molar amount of (a) and (b) is from 20 to 90 percent, more preferably from 30 to 90 percent, such as from 20 to 70 percent, e.g. from 30 to 70 percent, or wherein the cysteine analog is N,Acetyl-L-cysteine, wherein the molar amount (a) in view of the total molar amount of (a) and (b) is from 50 to 90 percent, preferably form 50 to 80 percent, more preferably from 50 to 70 percent.

In one embodiment, the concentration of (b) in said basal medium is equivalent to between 0.05 and 5 mmol/L of cysteine, such as between 0.1 and 1 mmol/L, e.g. between 0.2 and 0.6 mmol/L.

"equivalent to X mol of cysteine" herein indicates that if dimer forms, such as cystine or cystine analogs are used, they should be counted double for the purposes of calculating the amount to be used or added. E.g. 1 mmol/L of cystine is equivalent to 2 mmol/L of cysteine.

In another embodiment, during the production phase, the medium is supplemented with (a) cysteine/cystine analogs and (b) cysteine and/or cystine, wherein the sum of (a) and (b) added to the culture over the entire production phase is equivalent to between 1 and 75 mmol/L of cysteine, such as between 1 and 50 mmol/L, e.g. between 1 and 20 mmol/L, such as between 2 and 20 mmol/L, e.g. between 4 and 10 mmol/L.

In another embodiment, during the production phase, the medium is supplemented daily with (a) cysteine/cystine analogs and (b) cysteine and/or cystine, wherein the daily addition brings the concentration of (a)+(b) to a concentration equivalent to between 0.05 and 5 mmol/L of cysteine, such as between 0.1 and 1 mmol/L.

The production phase is operated preferably in a fed-batch mode, but any other mode such as batch, perfusion or chemostat modes can be used as an alternative.

Cell culture can take place in any suitable container such as a shake flask or a bioreactor, which may or may not be operated in a fed-batch mode depending on the scale of production required. These bioreactors may be either stirred-tank or air-lift reactors. Preferable, the production phase is carried out in a bioreactor, preferably with a volume of equal or more than 50 L, equal or more than 100 L, equal or more than 500 L, equal or more than 1000 L, equal or more than 2,000 L, equal or more than 5,000 L, equal or more than 10,000 L or equal or more than 20,000 L.

Preferably, the recombinant protein is produced during a production phase, wherein the production phase preferably has a duration of at least 7 days, more preferably at least 14 days.

In preferred embodiments, the culture is supplemented daily in the production phase.

In one embodiment of the method of the invention, the cell culture medium is supplemented with:
cysteine or cystine up to a total amount of from 10 wt % to 30 wt % of the expected total amount of recombinant protein produced; and/or
tryptophan up to a total amount of from 8 wt % to 35 wt % of the expected total amount of recombinant protein produced.

The total amount of cysteine or cystine and/or tryptophan added may be expressed herein as a percentage of the total amount of recombinant polypeptide produced. The term "wt %" as used herein refers to percentage of weight. "Total"

refers to the total amount as determined at the end of the production phase, i.e. the total amount of cysteine or cystine and/or tryptophan added over the course of the production phase and the total amount of recombinant protein produced over the course of the production phase, wherein the total amount of recombinant protein produced is measured at the end of the production phase.

The total amount of cysteine or cystine or tryptophan added is calculated as a function of the feed rate (or feed volume) and the concentration of cysteine or cystine or tryptophan in that feed and the concentration of cysteine or cystine or tryptophan in the medium where the feed is added per volume of feed added. The quantity of recombinant polypeptide produced is calculated as a function of the final volume of the cell culture medium and the final recombinant polypeptide titer. The ratio of these two calculated parameters is the total amount of cysteine or cystine and/or tryptophan added per quantity of recombinant polypeptide produced.

The host cells may initially (in step a.) be grown in a cell culture medium which may or may not already include cysteine/cystine analogs, cysteine, cystine and/or tryptophan. If the cell culture medium already includes an initial amount of cysteine/cystine analogs, cysteine, cystine and/or tryptophan, then the total amount will include this initial amount.

In one embodiment of the process of the invention, the cell culture medium is supplemented with cysteine or cystine up to a total amount of from 12.06 wt % to 28.03 wt % of the expected total amount of recombinant polypeptide produced, such as a total amount of from 12 wt % to 28 wt %, e.g. from 12 wt % to 25 wt %, such as from 12 wt % to 20 wt % of the expected total amount of recombinant polypeptide produced.

In another embodiment of the process of the invention, wherein the cell culture medium is supplemented with tryptophan up to a total amount of from 8.84 wt % to 32.06 wt % of the expected total amount of recombinant polypeptide produced, such as a total amount of from 8 wt % to 30 wt %, e.g. from 8 wt % to 25 wt %, such as from 8 wt % to 20 wt % of the expected total amount of recombinant polypeptide produced.

In another embodiment of the method of the invention,
the cysteine or cystine concentration in the cell culture does not exceed 0.9 g/L at any time point during the production phase, preferably wherein the cysteine or cystine concentration in the cell culture does not exceed 0.3 g/L at any time point during the production phase, and/or
the tryptophan concentration in the cell culture does not exceed 0.6 g/L at any time point during the production phase, preferably wherein the tryptophan concentration in the cell culture does not exceed 0.3 g/L at any time point during the production phase.

In a further embodiment of the method of the invention,
the total amount of cysteine or cystine provided during the process is from 2.9 to 12 g/($10^{12}$ cells), such as from 2.9 to 7 g/($10^{12}$ cells), e.g. from 5.6 to 7 g/($10^{12}$ cells), wherein cells refers to the expected integral viable cell count at the end of the production phase, and/or
the total amount of tryptophan provided during the process is from 2.5 to 7 g/($10^{12}$ cells), such as from 2.5 to 3.5 g/($10^{12}$ cells/L), wherein cells refers to the expected integral viable cell count at the end of the production phase.

It should be understood that the skilled person would know how to measure the amount of cysteine or cystine and/or tryptophan added to and/or present in a cell culture at a specific phase, such as the production phase. Similarly, the skilled person would know how to measure the total amount of recombinant polypeptide produced by a cell culture and consequently apply the teaching of the present invention to achieve the desired technical effect.

In order to design a process wherein the amounts of cysteine or cystine and/or tryptophan per total amount of recombinant polypeptide produced are kept within certain ranges, it may be required to perform one or more initial experiments to determine the approximate levels of recombinant polypeptide produced by particular host cells under particular culturing conditions. Once the approximate total levels of recombinant polypeptide produced are known, a process according to the invention can be designed wherein the amounts of cysteine or cystine and/or tryptophan per total amount of recombinant polypeptide produced are kept within the specified ranges.

Various strategies may be employed for reaching the total amount of cysteine/cystine analogs, cysteine, cystine and/or tryptophan in the cell culture medium during the production phase. In one embodiment, the total amount may be reached by adding cysteine/cystine analogs, cysteine, cystine and/or tryptophan right at the beginning of the production phase, for example only once or as being already included in the production cell culture medium. In another embodiment, the total amount may be reached by the summation of additions, for example daily addition or continuous addition, during the production phase. In yet another embodiment, the total amount may be reached by a combination of the initial cysteine/cystine analogs, cysteine, cystine and/or tryptophan concentration in the cell culture fluid at the start of the production phase, and by way of additions.

Accordingly, in one embodiment of the process of the invention, the total amount of cysteine/cystine analogs, cysteine, cystine and/or tryptophan in the cell culture medium is reached by adding cysteine/cystine analogs, cysteine, cystine and/or tryptophan to the cell culture medium:
  a. at the beginning of the production phase,
  b. once or multiple times at any time point during the production phase,
  c. through continuous addition during the production phase, or
  d. in any combination of a., b. and c.

In a further independent aspect, the invention relates to a cell culture medium suitable for culturing mammalian cells comprising N,N'-diacetyl-L-cystine-dimethylester.

Recombinant Polypeptides

The process of the invention can be used to produce any type of recombinant protein or polypeptide, including for example, peptides or larger polypeptides having significant tertiary structure as well as e.g. glycoproteins and multimeric proteins.

In some embodiments, the recombinant protein produced is a protein which, when produced under standard conditions, would result in a colored preparation at high concentration. Such coloration can be reduced or avoided using the method of the invention. Thus, in a preferred embodiment of the method of the invention, the recombinant protein is a protein which is not colorless at a concentration of 10 mg/ml or more, such as 50 mg/ml or more, when produced by host cells grown in a cell culture medium not comprising cysteine/cystine analogs, wherein color e.g. is determined as described in the Examples herein. Protein preparations, such as antibodies, that are to be administered subcutaneously to a patient, often have even higher proteins concentrations of e.g. 100 mg/ml or more, or even more than 150 mg/ml. At such concentrations, undesirable coloration frequently becomes a problem. Thus, in another preferred embodiment, the recombinant protein is a protein which, when produced by host cells grown in a cell culture medium not comprising cysteine/cystine analogs is not colorless at a concentration of 100 mg/ml or more, such as 150 mg/ml or more.

In a preferred embodiment, the recombinant protein produced in the process according to the invention is an antibody or an antigen-binding fragment thereof.

The term "antibody" or "antibodies" as used herein includes e.g. both monoclonal and polyclonal antibodies as well as both monospecific and multispecific, such as bispecific, antibodies.

Antibody" or "antibodies" include antibodies' of any species, in particular of mammalian species, typically having two heavy chains and two light chains, human antibodies of any isotype, including $IgA_1$, $IgA_2$, IgD, $IgG_1$, $IgG_{2a}$, $IgG_{2b}$, $IgG_3$, $IgG_4$ IgE, and IgM and modified variants thereof, non-human primate antibodies, e.g. from chimpanzee, baboon, rhesus or cynomolgus monkey, rodent antibodies, e.g. from mouse, rat or rabbit; goat or horse antibodies, and derivatives thereof, or of bird species such as chicken antibodies or of fish species such as shark antibodies. The term "antibody" or "antibodies" also refers to "chimeric" antibodies in which a first portion of at least one heavy and/or light chain antibody sequence is from a first species and a second portion of the heavy and/or light chain antibody sequence is from a second species. Chimeric antibodies of interest herein include "primatized" antibodies comprising variable domain antigen-binding sequences derived from a non-human primate (e.g. Old-World Monkey, such as baboon, rhesus or cynomolgus monkey) and human constant region sequences. "Humanized" antibodies are chimeric antibodies that contain a sequence derived from non-human antibodies. For the most part, humanized antibodies are human antibodies (recipient antibody) in which residues from a hypervariable region of the recipient are replaced by residues from a hypervariable region or complementarity determining region (CDR) of a non-human species (donor antibody) such as mouse, rat, rabbit, chicken or non-human primate, having the desired specificity, affinity, and activity. In most instances residues of the human (recipient) antibody outside of the CDR; i.e. in the framework region (FR), are additionally replaced by corresponding non-human residues. Furthermore, humanized antibodies may comprise residues that are not found in the recipient antibody or in the donor antibody. These modifications are made to further refine antibody performance. Humanization reduces the immunogenicity of non-human antibodies in humans, thus facilitating the application of antibodies to the treatment of human diseases. Humanized antibodies and several different technologies to generate them are well known in the art. The term "antibody" or "antibodies" also refers to human antibodies, which can be generated as an alternative to humanization. For example, it is possible to produce transgenic animals (e.g., mice) that are capable, upon immunization, of producing a full repertoire of human antibodies in the absence of production of endogenous murine antibodies. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies with specificity against a particular antigen upon immunization of the transgenic animal carrying the human germ-line immunoglobulin genes with said antigen. Technologies for producing such transgenic animals and technologies for isolating and producing the human antibodies from such transgenic animals are known in the art. Alternatively, in the transgenic animal; e.g. mouse, only the immunoglobulin genes coding for the variable regions of the mouse antibody are replaced with corresponding human variable immunoglobulin gene sequences. The mouse germline immunoglobulin genes coding for the antibody constant regions remain unchanged. In this way, the antibody effector functions in the immune system of the transgenic mouse and consequently the B cell development are essentially unchanged, which may lead to an improved antibody response upon antigenic challenge in vivo. Once the genes coding for a particular antibody of interest have been isolated from such transgenic animals the genes coding for the constant regions can be replaced with human constant region genes in order to obtain a fully human antibody. The term "antibody" or "antibodies" as used herein, also refers to an aglycosylated antibody.

The term "antigen-binding fragment thereof" or grammatical variations thereof as used herein refers to an antibody fragment. A fragment of an antibody comprises at least one heavy or light chain immunoglobulin domain as known in the art and binds to one or more antigen(s). Examples of antibody fragments according to the invention include Fab, Fab', F(ab')$_2$, and Fv and scFv fragments; as well as diabodies, triabodies, tetrabodies, minibodies, domain antibodies (dAbs), such as sdAbs, VHH or camelid antibodies (e.g. from camels or llamas such as Nanobodies™) and VNAR fragments, single-chain antibodies, bispecific, trispecific, tetraspecific or multispecific antibodies formed from antibody fragments or antibodies, including but not limited to Fab-Fv or Fab-Fv-Fv constructs. When used herein, antibody fragments also include molecules which comprises non-immunoglobulin-derived sequences in addition to immunoglobulin domains, e.g. in the form of fusion proteins. Antibody fragments as defined above are known in the art.

In a particularly preferred embodiment, the antibody or antigen-binding fragment thereof produced through the methods according to the invention is (Table 1):

1) an antibody or antigen-binding fragment thereof which
   a. comprises CDR-H1 having the sequence as defined in SEQ ID NO:1; CDR-H2 having the sequence as defined in SEQ ID NO:2; CDR-H3 having the sequence as defined in SEQ ID NO:3; CDR-L1 having the sequence as defined in SEQ ID NO:4; CDR-L2 having the sequence as defined in SEQ ID NO:5 and CDR-L3 having the sequence as defined in SEQ ID NO:6; or
   b. comprises a light variable region having the sequence as defined in SEQ ID NO: 7 and a heavy variable region having the sequence as defined in SEQ ID NO: 8; or
   c. comprises a light variable region having at least 80% identity or similarity, preferably 90% identity or similarity to the sequence as defined in SEQ ID NO: 7 and a heavy variable region having at least 80% identity or similarity, preferably 90% identity or similarity to the sequence as defined in SEQ ID NO: 8;
   d. comprises a light variable region having the sequence as defined in SEQ ID NO: 7 and a heavy chain having the sequence as defined in SEQ ID NO: 11; or e. comprises a light variable region having at least 80% identity or similarity, preferably 90% identity or similarity to the sequence as defined in SEQ ID NO: 7 and a heavy chain having at least 80% identity or similarity, preferably 90% identity or similarity to the sequence as defined in SEQ ID NO: 11; or
2) an antibody which comprises a light chain having the sequence as defined in SEQ ID NO: 9 and a heavy chain having the sequence as defined in SEQ ID NO: 10; or
3) an antibody which comprises a light chain having at least 80% identity or similarity, preferably 90% identity or similarity to the sequence as defined in SEQ ID NO: 9 and a heavy chain having at least 80% identity or similarity, preferably 90% identity or similarity to the sequence as defined in SEQ ID NO: 10.

Complementarity determining regions ("CDR") are defined herein according to the Kabat definition. The Kabat definition is a standard for numbering the residues in an antibody and it is typically used to identify CDR regions (Kabat et al., (1991), 5th edition, NIH publication No. 91-3242).

The recombinant protein or the preferred antibody or antigen-binding fragment thereof may be typically produced by host cells containing a vector encoding the polypeptide or antibody nucleotide sequence. Antibodies or antigen-binding fragment thereof may comprise only a heavy or light chain polypeptide, in which case only a heavy chain or light chain polypeptide coding sequence needs to be used to transfect the cells. For production of products comprising both heavy and light chains, the cells may be transfected with two vectors, a first vector encoding a light chain polypeptide and a second vector encoding a heavy chain polypeptide. Alternatively, a single vector may be used, the vector including sequences encoding light chain and heavy chain polypeptides.

Optional Further Steps

The method of the invention optionally further comprises a step of recovering the recombinant protein from the cell culture medium. Subsequently, the recombinant protein may be purified, e.g. if the protein is an antibody, using Protein A chromatography. The method further optionally comprises a step of formulating the purified recombinant protein, e.g. into a formulation with a high protein concentration, such as

```
CDR-H1            GFTFSNYGMV
SEQ ID NO: 1

CDR-H2            YIDSDGDNTYYRDSVKG
SEQ ID NO: 2

CDR-H3            GIVRPFLY
SEQ ID NO: 3

CDR-L1            KSSQSLVGASGKTYLY
SEQ ID NO: 4

CDR-L2            LVSTLDS
SEQ ID NO: 5

CDR-L3            LQGTHFPHT
SEQ ID NO: 6

Light variable    DIQMTQSPSS LSASVGDRVT ITCKSSQSLV GASGKTYLYW
region            LFQKPGKAPK RLIYLVSTLD SGIPSRFSGS GSGTEFTLTI
SEQ ID NO: 7      SSLQPEDFAT YYCLQGTHFP HTFGQGTKLE IK Heavy variable    EVPLVESGGG LVQPGGSLRL SCAVSGFTFS NYGMVWVRQA
region            PGKGLEWVAY IDSDGDNTYY RDSVKGRFTI SRDNAKSSLY
SEQ ID NO: 8      LQMNSLRAED TAVYYCTTGI VRPFLYWGQG TLVTVS Light chain       DIQMTQSPSS LSASVGDRVT ITCKSSQSLV GASGKTYLYW
SEQ ID NO: 9      LFQKPGKAPK RLIYLVSTLD SGIPSRFSGS GSGTEFTLTI
                  SSLQPEDFAT YYCLQGTHFP HTFGQGTKLE IKRTVAAPSV
                  FIFPPSDEQL KSGTASVVCL LNNFYPREAK VQWKVDNALQ
                  SGNSQESVTE QDSKDSTYSL SSTLTLSKAD YEKHKVYACE
                  VTHQGLSSPV TKSFNRGEC Heavy chain       EVPLVESGGG LVQPGGSLRL SCAVSGFTFS NYGMVWVRQA
SEQ ID NO: 10     PGKGLEWVAY IDSDGDNTYY RDSVKGRFTI SRDNAKSSLY
                  LQMNSLRAED TAVYYCTTGI VRPFLYWGQG TLVTVSSAST
                  KGPSVFPLAP CSRSTSESTA ALGCLVKDYF PEPVTVSWNS
                  GALTSGVHTF PAVLQSSGLY SLSSVVTVPS SSLGTKTYTC
                  NVDHKPSNTK VDKRVESKYG PPCPPCPAPE FLGGPSVFLF
                  PPKPKDTLMI SRTPEVTCVV VDVSQEDPEV QFNWYVDGVE
                  VHNAKTKPRE EQFNSTYRVV SVLTVLHQDW LNGKEYKCKV
                  SNKGLPSSIE KTISKAKGQP REPQVYTLPP SQEEMTKNQV
                  SLTCLVKGFY PSDIAVEWES NGQPENNYKT TPPVLDSDGS
                  FFLYSRLTVD KSRWQEGNVF SCSVMHEALH NHYTQKSLSL
                  SLGK Fab heavy chain   EVPLVESGGG LVQPGGSLRL SCAVSGFTFS NYGMVWVRQA
SEQ ID NO: 11     PGKGLEWVAY IDSDGDNTYY RDSVKGRFTI SRDNAKSSLY
                  LQMNSLRAED TAVYYCTTGI VRPFLYWGQG TLVTVSSAST
                  KGPSVFPLAP SSKSTSGGTA ALGCLVKDYF PEPVTVSWNS
                  GALTSGVHTF PAVLQSSGLY SLSSVVTVPS SSLGTQTYIC
                  NVNHKPSNTK VDKKVEPKSC
``` a concentration of 10 mg/ml or more, e.g. 50 mg/ml or more, such as 100 mg/ml or more, e.g. 150 mg/ml or more. In a further embodiment, the protein is lyophilised or spray-dried. The protein may be administered in a dry form to a patient or be reconstituted into a liquid formation prior to administration.

Products Obtained or Obtainable by the Method of the Invention

In a further aspect, the invention relates to a recombinant protein preparation, such as a bulk recombinant protein preparation, obtainable or obtained by the methods according to the invention. The recombinant proteins, preferably the antibodies or antigen-binding fragments thereof in said preparation so obtained exhibit reduced heterogeneity as compared to the same recombinant proteins obtained with the same process, but wherein the medium does not include cysteine/cystine analogs. In preferred embodiments, the preparation is colorless.

Further Aspects and Embodiments of the Invention

1. A method for reducing the heterogeneity of a population of recombinant proteins produced in cell culture, said method comprising growing host cells producing a recombinant protein in a cell culture medium wherein the cell culture medium comprises one or more cysteine/cystine analogs wherein the reduction of the heterogeneity is obtained without substantially reducing the titer of the recombinant proteins at the end of the production.
2. The method according to embodiment 1, wherein said reduction of heterogeneity comprises reducing
   a. color or intensity of color;
   b. charge heterogeneity, preferably by reducing acidic peak group species (APG) and/or basic peak group species (BPG), whereby the main charge species substantially does not decrease; and/or
   c. amino acid oxidation, preferably methionine oxidation.
3. In one embodiment according to the present invention, the cysteine/cystine analogs comprise or consist of one or more compounds selected from the compounds represented by formula 1 and 2, and salts thereof:

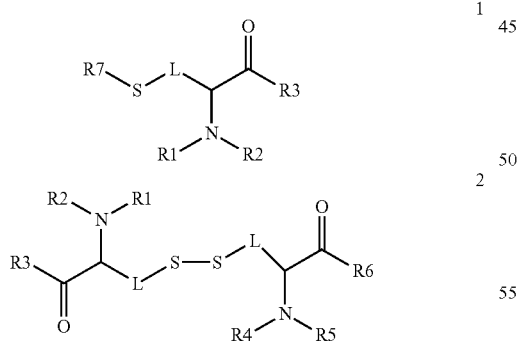

wherein,

R1, R2, R4 and R5 independently represent hydrogen, amino carbonyl, $C_{2-22}$acyl, $C_{1-22}$alkyl which group is optionally substituted by one or two substituents selected from hydroxy and $C_{1-22}$alkoxy; $C_{1-22}$ heteroalkyl, hydroxysulphonyl, $C_{1-22}$alkylsulphonyl, or $C_{5-22}$aryl sulphonyl;

R3 and R6 independently represent hydroxy; NH$_2$; $C_{1-22}$alkoxy wherein one or more carbons of the $C_{1-22}$ alkyl may be optionally replaced by an aryl or an heteroaryl; $C_{1-22}$ alkylamino which group is optionally substituted by a hydroxy or a $C_{1-22}$ alkyl; hydroxy amino; $C_{1-22}$ alkoxy amino; $C_{1-22}$ alkylamino wherein one or more carbons of the $C_{1-22}$alkyl are replaced by an aryl or an heteroaryl; $C_{1-22}$heteroalkylamino; di($C_{1-22}$ alkyl)amino which is optionally substituted by a hydroxy; di($C_{1-22}$alkyl) amino wherein one or more carbons of the $C_{1-22}$alkyl are replaced by an aryl or heteroaryl; or di($C_{1-22}$heteroalkyl)amino;

R7 represents hydrogen, phosphate or sulphate;

L represents an optionally substituted $C_{1-10}$alkylene chain; and with the proviso that the compound is not cysteine or cystine.

4. The method according to embodiment 3, wherein $C_{1-22}$alkyl refers to aliphatic hydrocarbon groups which may be straight or branched and may comprise 1 to 22 carbon atoms in the chain, such as $C_{6-22}$ alkyl groups, $C_{12-22}$ alkyl groups, $C_{1-16}$ alkyl groups, $C_{1-10}$ alkyl groups and $C_{1-6}$ alkyl groups.
5. The method according to embodiment 3 or 4, wherein $C_{5-22}$aryl refers to an unsaturated aromatic carbocyclic group of from 5 to 22 carbon atoms having a single ring or multiple condensed rings, such as $C_{5-14}$ aryl groups, $C_{5-10}$ aryl groups.
6. The method according to any of the embodiments 3 to 5, wherein "$C_{5-22}$heteroaryl" represents aromatic carbocyclic groups of from 5 to 22 carbon atoms having a single ring or multiple condensed rings, wherein one or more of the said carbon atoms have been replaced by one or more heteroatoms selected from oxygen, sulphur and nitrogen and wherein $C_{5-22}$heteroaryl include $C_{5-14}$ heteroaryl aryl groups, suitably include $C_{5-10}$ heteroaryl groups.
7. The method according to any of the embodiments 3 to 5, wherein $C_{2-22}$acyl refers to a group represented by formula —(C=O)R wherein R represents a $C_{1-22}$ alkyl group as defined here above, and include $C_{2-6}$acyl groups, $C_{6-22}$acyl groups, and $C_{12-22}$acyl groups.
8. The method according to any of the embodiments 3 to 7, wherein $C_{1-22}$alkoxy refers to a group represented by formula —O—R, wherein R represents a $C_{1-22}$ alkyl group as defined here above and include $C_{1-6}$alkoxy-groups $C_{6-22}$alkoxy groups and $C_{12-22}$alkoxy groups.
9. The method according to any of the embodiments 3 to 8, wherein $C_{1-22}$heteroalkyl refers to a $C_{1-22}$ alkyl as defined above wherein one or more carbon atoms are replaced by one or more oxygen or nitrogen atom and include $C_{1-6}$heteroalkyl groups, $C_{6-22}$heteroalkyl groups and $C_{12-22}$heteroalkyl groups.
10. The method according to any of the embodiments 3 to 9, wherein hydroxysulphonyl refers to a group represented by formula —S(=O)$_2$—OH.
11. The method according to any of the embodiments 3 to 10, wherein 1-22alkyl sulphonyl refers to a group represented by formula —S(=O)2-R, wherein R represents a C1-22 alkyl group as defined here above and include C1-6 alkyl sulphonyl groups and C6-22 alkyl sulphonyl groups, C12-22 alkyl sulphonyl groups.
12. The method according to any of the embodiments 3 to 11, wherein $C_{5-22}$aryl sulphonyl as used herein refers to a group represented by formula —S(=O)$_2$—R', wherein R' represents a $C_{5-22}$ aryl group as defined here above.

13. The method according to any of the embodiments 3 to 12, wherein $C_{1-22}$ alkylamino refers to a group represented by formula —NH—R wherein R represents a $C_{1-22}$ alkyl group as defined here above and include $C_{1-6}$alkylamino groups, $C_{6-22}$alkylamino groups and $C_{12-22}$alkylamino groups.

14. The method according to any of the embodiments 3 to 13, wherein $C_{1-22}$ alkoxy amino refers to a group represented by formula —NH—OR wherein R represents a $C_{1-22}$ alkyl group as defined here above and include $C_{1-6}$alkoxyamino groups, $C_{6-22}$alkoxyamino groups and $C_{12-22}$alkoxyamino groups.

15. The method according to any of the embodiments 3 to 14, wherein di($C_{1-22}$ alkyl)amino refers to by formula —NRR' wherein R and R' represent independently a $C_{1-22}$ alkyl group as defined here above and include di($C_{1-6}$ alkyl)amino, di($C_{6-22}$ alkyl)amino and di($C_{12-22}$ alkyl)amino.

16. The method according to any of the embodiments 3 to 15, wherein $C_{1-22}$heteroalkylamino refers to a group represented by formula —NH—R wherein R represents a $C_{1-22}$ heteroalkyl group as defined here above and include $C_{1-6}$heteroalkylamino, $C_{6-22}$heteroalkylamino and $C_{12-22}$heteroalkylamino.

17. The method according to any of the embodiments 3 to 16, wherein di($C_{1-22}$heteroalkyl)amino refers to by formula —NRR' wherein R and R' represent independently a $C_{1-22}$ heteroalkyl group as defined here above and include di($C_{1-6}$ heteroalkyl)amino, di($C_{6-22}$ heteroalkyl)amino and di($C_{12-22}$ heteroalkyl)amino.

18. The method according to any of the embodiments 3 to 17, wherein $C_{1-10}$ alkylene chain refers to a divalent straight or branched alkylene chain containing 1 to 10 carbon atoms and include methylene, ethylene, propylene and butylene.

19. The method according to any of the embodiments 3 to 18, wherein "amino carbonyl" refers to a group represented by formula —CO—N($R_a R_b$) wherein the carbon of —CO binds to nitrogen of the cysteine/cystine analog and wherein $R_a$ and $R_b$ independently from each other represent a $C_{1-22}$alkyl as defined above.

20. The method according to any of the embodiments 3 to 19, wherein the cysteine/cystine analogs are selected from cysteine analogs represented by formula 1, wherein R1, R2, R3, R4, R5, R6 R7 and L are as defined here above.

21. The method according to any of the embodiments 3 to 20, wherein R7 represents hydrogen.

22. The method according to any of the embodiments 3 to 21, wherein the cysteine/cysteine analogs are selected from cystine analogs represented by formula 2, wherein R1, R2, R3, R4, R5, R6, R7 and L are as defined here above.

23. The method according to any of the embodiments 3 to 22, wherein R1, R2, R4 and R5 independently represent hydrogen, $C_{2-22}$acyl, $C_{1-22}$alkyl which group is optionally substituted by one or two substituents selected from hydroxy and $C_{1-22}$alkoxy; or $C_{1-22}$ heteroalkyl.

24. The method according to any of the embodiments 3 to 23, wherein R3 and R6 independently represent hydroxy; $NH_2$; $C_{1-22}$alkoxy wherein one or more carbons of the $C_{1-22}$ alkyl may be optionally replaced by an aryl or an heteroaryl; $C_{1-22}$ alkylamino which group is optionally substituted by a hydroxy; or di($C_{1-22}$ alkyl)amino which is optionally substituted by a hydroxy.

25. The method according to any of the embodiments 3 to 24, wherein L represents a $C_{1-4}$alkylene chain, optionally substituted, by one or more $C_{1-6}$ alkyl, preferably, two methyl groups.

26. The method according to any of the embodiments 3 to 25, wherein R1 represents hydrogen or $C_{2-22}$acyl, such as. hydrogen or $C_{2-6}$acyl.

27. The method according to any of the embodiments 3 to 26, wherein R2 represents hydrogen or $C_{2-22}$ acyl, such as $C_{2-6}$acyl.

28. The method according to any of the embodiments 3 to 27, wherein R3 represents hydroxy or $C_{1-22}$alkoxy such as $C_{1-6}$alkoxy.

29. The method according to any of the embodiments 3 to 28, wherein R4 represents hydrogen or $C_{2-22}$ acyl such as $C_{2-6}$acyl.

30. The method according to any of the embodiments 3 to 29, wherein R5 represents hydrogen or $C_{2-22}$ acyl such as hydrogen or $C_{2-6}$acyl.

31. The method according to any of the embodiments 3 to 30, wherein R6 represents hydroxy or $C_{1-22}$alkoxy such as $C_{1-6}$alkoxy.

32. The method according to any of the embodiments 3 to 31, wherein L represents methylene or ethylene.

33. The method according to any of the embodiments 3 to 32, wherein the cysteine/cystine analogs comprises one or more compounds selected from the compounds represented by formula 1, and salts thereof, wherein L, R1, R2, R3 and R7 areas defined above, with the provisos (i) that if one of the R1 or R2 groups, represents, $C_{6-22}$acyl, $C_{6-22}$alkyl which group is optionally substituted by one or two substituents selected from hydroxy and $C_{1-22}$alkoxy; $C_{6-22}$ heteroalkyl, hydroxysulphonyl, $C_{6-22}$alkylsulphonyl, or $C_{5-22}$aryl sulphonyl; then the remaining R1 or R2 group represents independently hydrogen, amino carbonyl, $C_{2-6}$acyl, $C_{1-6}$alkyl which group is optionally substituted by one or two substituents selected from hydroxy and $C_{1-6}$alkoxy; $C_{1-6}$ heteroalkyl, hydroxysulphonyl, $C_{1-6}$alkylsulphonyl, or $C_{5-10}$aryl sulphonyl; and R3 represents hydroxy; $NH_2$; $C_{1-6}$alkoxy wherein one or more carbons of the $C_{1-22}$ alkyl may be optionally replaced by an aryl or an heteroaryl; $C_{1-6}$ alkylamino which group is optionally substituted by a hydroxy or a $C_{1-6}$ alkyl; hydroxy amino; $C_{1-6}$ alkoxy amino; $C_{1-6}$ alkylamino wherein one or more carbons of the $C_{1-6}$alkyl are replaced by an aryl or an heteroaryl; $C_{1-6}$heteroalkylamino; di($C_{1-6}$ alkyl)amino which is optionally substituted by a hydroxy; di($C_{1-6}$alkyl) amino wherein one or more carbons of the $C_{1-6}$alkyl are replaced by an aryl or heteroaryl; or di($C_{1-6}$heteroalkyl)amino; and (ii) that if R3 represents $C_{6-22}$alkoxy wherein one or more carbons of the $C_{6-22}$ alkyl may be optionally replaced by an aryl or an heteroaryl; $C_{6-22}$ alkylamino which group is optionally substituted by a hydroxy or a $C_{1-22}$ alkyl; hydroxy amino; $C_{6-22}$ alkoxy amino; $C_{6-22}$ alkylamino wherein one or more carbons of the $C_{1-22}$alkyl are replaced by an aryl or an heteroaryl; $C_{6-22}$heteroalkylamino; di($C_{6-22}$ alkyl)amino which is optionally substituted by a hydroxy; di($C_{6-22}$alkyl) amino wherein one or more carbons of the $C_{6-22}$alkyl are replaced by an aryl or heteroaryl; or di($C_{6-22}$heteroalkyl)amino, then R1 and R2 independently represents hydrogen, amino carbonyl, $C_{2-6}$acyl, $C_{1-6}$alkyl which group is optionally substituted by one or two substituents selected from hydroxy and $C_{1-6}$alkoxy; $C_{1-6}$ heteroalkyl, hydroxysulphonyl, $C_{1-6}$alkylsulphonyl, or $C_{5-10}$aryl sulphonyl.

34. The method according to any of the embodiments 3 to 33, wherein the cysteine/cystine analogs comprise or consist of the compound represented by formula 2, and salts thereof, wherein L, R1, R2, R3, R4, R5, R6 and R7 are as defined above, with the provisos:
    (i) that if
    one of the of R1 and R2 groups represents $C_{6-22}$acyl, $C_{6-22}$alkyl which group is optionally substituted by one or two substituents selected from hydroxy and $C_{1-22}$alkoxy; $C_{6-22}$ heteroalkyl, hydroxysulphonyl, $C_{6-22}$alkylsulphonyl, or $C_{5-22}$aryl sulphonyl; and if one of the R4 and R5 groups represents $C_{6-22}$acyl, $C_{6-22}$alkyl which group is optionally substituted by one or two substituents selected from hydroxy and $C_{1-22}$alkoxy; $C_{6-22}$ heteroalkyl, hydroxysulphonyl, $C_{6-22}$alkylsulphonyl, or $C_{5-22}$aryl sulphonyl, then
    the remaining R1, R2, R4, or R5 groups independently represent hydrogen, amino carbonyl, $C_{2-6}$acyl, $C_{1-6}$alkyl which group is optionally substituted by one or two substituents selected from hydroxy and $C_{1-6}$alkoxy; $C_{1-6}$ heteroalkyl, hydroxysulphonyl, $C_{1-6}$alkylsulphonyl, or $C_{5-10}$aryl sulphonyl; and
    R3 and R6 independently represents hydroxy; NH2; $C_{1-6}$alkoxy wherein one or more carbons of the $C_{1-22}$ alkyl may be optionally replaced by an aryl or an heteroaryl; $C_{1-6}$ alkylamino which group is optionally substituted by a hydroxy or a $C_{1-6}$ alkyl; hydroxy amino; $C_{1-6}$ alkoxy amino; $C_{1-6}$ alkylamino wherein one or more carbons of the $C_{1-6}$alkyl are replaced by an aryl or an heteroaryl; $C_{1-6}$heteroalkylamino; di($C_{1-6}$ alkyl)amino which is optionally substituted by a hydroxy; di($C_{1-6}$alkyl)amino wherein one or more carbons of the $C_{1-6}$alkyl are replaced by an aryl or heteroaryl; or di($C_{1-6}$heteroalkyl)amino;
    (ii) that if only if one of R1, R2, R4 and R5 groups independently represent $C_{6-22}$acyl, $C_{6-22}$alkyl which group is optionally substituted by one or two substituents selected from hydroxy and $C_{1-22}$alkoxy; $C_{6-22}$ heteroalkyl, hydroxysulphonyl, $C_{6-22}$alkylsulphonyl, or $C_{5-22}$aryl sulphonyl; then
    one of R3 and R6 may r represent $C_{6-22}$alkoxy wherein one or more carbons of the $C_{1-22}$ alkyl may be optionally replaced by an aryl or an heteroaryl; $C_{6-22}$ alkylamino which group is optionally substituted by a hydroxy or a $C_{1-22}$ alkyl; $C_{6-22}$ alkoxy amino; $C_{6-22}$ alkylamino wherein one or more carbons of the $C_{1-22}$alkyl are replaced by an aryl or an heteroaryl; $C_{6-22}$heteroalkylamino; di($C_{6-22}$ alkyl)amino which is optionally substituted by a hydroxy; di($C_{6-22}$alkyl) amino wherein one or more carbons of the $C_{6-22}$alkyl are replaced by an aryl or heteroaryl; or di($C_{6-22}$heteroalkyl)amino;
    (iii) that if none of the R1, R2, R4 and R5 groups represents $C_{6-22}$acyl, $C_{6-22}$alkyl which group is optionally substituted by one or two substituents selected from hydroxy and $C_{1-22}$alkoxy; $C_{6-22}$ heteroalkyl, hydroxysulphonyl, $C_{6-22}$alkylsulphonyl, or $C_{5-22}$aryl sulphonyl; then
    R3 and R6 may both represent independently $C_{6-22}$alkoxy wherein one or more carbons of the $C_{1-22}$ alkyl may be optionally replaced by an aryl or an heteroaryl; $C_{6-22}$ alkylamino which group is optionally substituted by a hydroxy or a $C_{1-22}$ alkyl; $C_{6-22}$ alkoxy amino; $C_{6-22}$ alkylamino wherein one or more carbons of the $C_{1-22}$alkyl are replaced by an aryl or an heteroaryl; $C_{6-22}$heteroalkylamino; di($C_{6-22}$ alkyl)amino which is optionally substituted by a hydroxy; di($C_{6-22}$alkyl)amino wherein one or more carbons of the $C_{6-22}$alkyl are replaced by an aryl or heteroaryl; or di($C_{6-22}$heteroalkyl)amino.

35. The method according to any of the embodiments 3 to 34, wherein the cysteine/cystine analogs comprise or consist of salts of formula 1 and 2.

36. The method according the embodiment 35, wherein the salts are formed by reaction of a hydroxy group present on the cysteine/cystine analogs.

37. The method according the embodiments 35 or 36, wherein the salts include alkali metal salts, for example sodium, potassium or lithium salts; alkali earth metal salts, for example magnesium or calcium salts; ammonium salts, for example tetra alkyl or aryl ammonium salts; sulphonium salts, for example trialkyl or aryl sulphonium; and phosphonium salts, for example tetra alkyl or aryl phosphonium salts.

38. The method according any one embodiments 35 to 37, wherein the salts are formed by reaction of an amino group present on the cysteine/cysteine analogs, such as the reaction of the amino group with an inorganic acid or an organic acid and include mono- or di-HCl salts, $H_2SO_4$ salts, $H_3PO_4$ salts, acetate and fumarate.

39. The method according any one embodiments 3 to 38, wherein the cysteine/cysteine analogs as defined here above have the same chirality as L-cysteine.

40. The method according any one embodiments 3 to 39, wherein the cysteine/cysteine analogs are selected from N,N'-diacetyl-L-cystine-dimethylester, N-Acetyl-L-cysteine and N,N'-Diacetyl-L-cystine, or S-sulfocysteine.

41. The method according to any one of embodiments 3 to 40, wherein the cysteine/cystine analogs comprise, or consist of, compounds that have the same chirality as L-cysteine.

42. The method according to any one of embodiments 3 to 41, wherein the cysteine/cystine analogs consists of, N,N'-diacetyl-L-cystine-dimethylester.

43. The method according to any one of the preceding embodiments, wherein said cell culture medium comprises:
    (a) cysteine/cystine analogs; and
    (b) cysteine and/or cystine,
    wherein the molar ratio of (a) to (b) is between 1:18 and 18:1.

44. The method according to any one of the preceding embodiments, wherein the method comprises the steps of:
    (i) inoculating said host cells in a basal medium, wherein the basal medium optionally comprises an initial amount of:
    (a) cysteine/cystine analogs; and/or
    (b) cysteine and/or cystine,
    (ii) progressing the culture through a production phase wherein the recombinant protein is produced by the cells, wherein, during said production phase, the cell culture medium is supplemented with:
    (a) cysteine/cystine analogs; and/or
    (b) cysteine and/or cystine,
    wherein (a) and (b) may be added simultaneously or sequentially, wherein, when the contents of the basal medium and the total supplements added are added up, the molar ratio of (a) to (b) is between 1:18 and 18:1.
45. The method according to embodiment 43 or 44, wherein said molar ratio of (a) to (b) is between 1:15 and 15:1, e.g. between 1:12 and 12:1, such as between 1:10 and 10:1, e.g. between 1:8 and 8:1, such as between 1:6 and 6:1, e.g. between 1:4 and 4:1, such as between 1:3 and 3:1, e.g. between 1:2 and 2:1, such as between 1.5:1 and 1:1.5, e.g. a molar ratio of 1:1.
46. The method according to embodiment 43 or 44, wherein the concentration of (b) in said basal medium is equivalent to between 0.05 and 5 mmol/L of cysteine, such as between 0.1 and 1 mmol/L, e.g. between 0.2 and 0.6 mmol/L.
47. The method according to any one of embodiments 43 to 46, wherein, during the production phase, the medium is supplemented with (a) cysteine/cystine analogs and (b) cysteine and/or cystine, wherein the sum of (a) and (b) added to the culture over the entire production phase is equivalent to between 1 and 75 mmol/L of cysteine, such as between 2 and 20 mmol/L, e.g. between 4 and 10 mmol/L.
48. The method according to any one of embodiments 43 to 46, wherein, during the production phase, the medium is supplemented daily with (a) cysteine/cystine analogs and (b) cysteine and/or cystine, wherein the daily addition brings the concentration of (a)+(b) to a concentration equivalent to between 0.05 and 5 mmol/L of cysteine, such as between 0.1 and 1 mmol/L.
49. The method according to any one of embodiments 43 to 48, wherein, during said production phase, the cell culture medium is supplemented with:
cysteine or cystine up to a total amount of from 10 wt % to 30 wt % of the expected total amount of recombinant protein produced; and/or
tryptophan up to a total amount of from 8 wt % to 35 wt % of the expected total amount of recombinant protein produced.
50. The method according to any one of embodiments 43 to 49, wherein
the cysteine or cystine concentration in the cell culture does not exceed 0.9 g/L at any time point during the production phase, preferably wherein the cysteine or cystine concentration in the cell culture does not exceed 0.3 g/L at any time point during the production phase, and/or
the tryptophan concentration in the cell culture does not exceed 0.6 g/L at any time point during the production phase, preferably wherein the tryptophan concentration in the cell culture does not exceed 0.3 g/L at any time point during the production phase.
51. The method according to any one of embodiments 43 to 50, wherein
the total amount of cysteine or cystine provided during the process is from 2.9 to 12 g/($10^{12}$ cells), such as from 2.9 to 7 g/($10^{12}$ cells), wherein cells refers to the expected integral viable cell count at the end of the production phase, and/or
the total amount of tryptophan provided during the process is from 2.5 to 7 g/($10^{12}$ cells), such as from 2.5 to 3.5 g/($10^{12}$ cells/L), wherein cells refers to the expected integral viable cell count at the end of the production phase.
52. The method according to any one of the preceding embodiments, wherein the method is a batch method.
53. The method according to any one of the preceding embodiments, wherein the recombinant protein is produced during a production phase, preferably wherein the production phase has a duration of at least 7 days, more preferably at least 14 days.
54. The method according to any one of the preceding embodiments, wherein the culture is supplemented daily in the production phase.
55. The method according to any one of the preceding embodiments, wherein the production phase is carried out in a bioreactor, preferably with a volume of equal or more than 50 L, equal or more than 100 L, equal or more than 500 L, equal or more than 1000 L, equal or more than 2,000 L, equal or more than 5,000 L, equal or more than 10,000 L or equal or more than 20,000 L.
56. The method according to any one of the preceding embodiments, wherein the host cells are mammalian cells, preferably CHO cells.
57. The method according to any one of the preceding embodiments, wherein the recombinant protein is an antibody or an antigen-binding fragment thereof.
58. The method according to embodiment 57, wherein the antibody or antigen-binding fragment thereof is:
i) an antibody or antigen-binding fragment thereof which
a. comprises CDR-H1 having the sequence as defined in SEQ ID NO:1; CDR-H2 having the sequence as defined in SEQ ID NO:2; CDR-H3 having the sequence as defined in SEQ ID NO:3; CDR-L1 having the sequence as defined in SEQ ID NO:4; CDR-L2 having the sequence as defined in SEQ ID NO:5 and CDR-L3 having the sequence as defined in SEQ ID NO:6; or
b. comprises a light variable region having the sequence as defined in SEQ ID NO: 7 and a heavy variable region having the sequence as defined in SEQ ID NO: 8; or
c. comprises a light variable region having at least 80% identity or similarity, preferably 90% identity or similarity to the sequence as defined in SEQ ID NO: 7 and a heavy variable region having at least 80% identity or similarity, preferably 90% identity or similarity to the sequence as defined in SEQ ID NO: 8;
d. comprises a light variable region having the sequence as defined in SEQ ID NO: 7 and a heavy chain having the sequence as defined in SEQ ID NO: 11; or
e. comprises a light variable region having at least 80% identity or similarity, preferably 90% identity or similarity to the sequence as defined in SEQ ID NO: 7 and a heavy chain having at least 80% identity or similarity, preferably 90% identity or similarity to the sequence as defined in SEQ ID NO: 11; or
ii) an antibody which comprises a light chain having the sequence as defined in SEQ ID NO: 9 and a heavy chain having the sequence as defined in SEQ ID NO: 10; or
iii) an antibody which comprises a light chain having at least 80% identity or similarity, preferably 90% identity or similarity to the sequence as defined in SEQ ID NO: 9 and a heavy chain having at least 80% identity or similarity, preferably 90% identity or similarity to the sequence as defined in SEQ ID NO: 10.

59. The method according to any one of the preceding embodiments, wherein the recombinant protein is a protein which is not colorless at a concentration of 10 mg/ml or more, such as 50 mg/ml or more, when produced by host cells grown in a cell culture medium not comprising cysteine/cystine analogs, wherein color e.g. is determined as described in the Examples herein.
60. The method according to any one of the preceding embodiments, wherein the method comprises the step of recovering the recombinant protein from the cell culture medium and a further step of purifying the recombinant protein.
61. The method according to embodiment 60 wherein the purification comprises Protein A chromatography.
62. The method according to embodiment 60 or 61, further comprising the step of formulating the purified recombinant protein.
63. A method for producing a recombinant protein preparation comprising:
    (i) inoculating said host cells in a basal medium, wherein the basal medium optionally comprises an initial amount of:
    (a) cysteine/cystine analogs; and/or
    (b) cysteine and/or cystine,
    (ii) progressing the culture through a production phase wherein the recombinant protein is produced by the cells, wherein, during said production phase, the cell culture medium is supplemented with:
    (a) cysteine/cystine analogs; and/or
    (b) cysteine and/or cystine,
    wherein (a) and (b) may be added simultaneously or sequentially,
    wherein, when the contents of the basal medium and the total supplements added are added up, the molar ratio of (a) to (b) is between 1:18 and 18:1.
64. The method according to embodiment 63, wherein the cysteine/cystine analogs are as described in embodiments 3-41 above.
65. The method according embodiments 63 or 64, wherein said molar ratio of (a) to (b) is between 1:15 and 15:1, e.g. between 1:12 and 12:1, such as between 1:10 and 10:1, e.g. between 1:8 and 8:1, such as between 1:6 and 6:1, e.g. between 1:4 and 4:1, such as between 1:3 and 3:1, e.g. between 1:2 and 2:1, such as between 1.5:1 and 1:1.5, e.g. a molar ratio of 1:1.
66. The method according to any one of embodiments 63 to 65, wherein the concentration of (b) in said basal medium is equivalent to between 0.05 and 5 mmol/L of cysteine, such as between 0.1 and 1 mmol/L, e.g. between 0.2 and 0.6 mmol/L.
67. The method according to any one of embodiments 63 to 66, wherein, during the production phase, the medium is supplemented with (a) cysteine/cystine analogs and (b) cysteine and/or cystine, wherein the sum of (a) and (b) added to the culture over the entire production phase is equivalent to between 1 and 75 mmol/L of cysteine, such as between 2 and 20 mmol/L, e.g. between 4 and 10 mmol/L.
68. The method according to any one of embodiments 63 to 67, wherein, during the production phase, the medium is supplemented daily with (a) cysteine/cystine analogs and (b) cysteine and/or cystine, wherein the daily addition brings the concentration of (a)+(b) to a concentration equivalent to between 0.05 and 5 mmol/L of cysteine, such as between 0.1 and 1 mmol/L.
69. The method according to any one of embodiments 63 to 68, wherein, during said production phase, the cell culture medium is supplemented with:
    cysteine or cystine up to a total amount of from 10 wt % to 30 wt % of the expected total amount of recombinant protein produced; and/or
    tryptophan up to a total amount of from 8 wt % to 35 wt % of the expected total amount of recombinant protein produced.
70. The method according to any one of embodiments 63 to 69, wherein
    the cysteine or cystine concentration in the cell culture does not exceed 0.9 g/L at any time point during the production phase, preferably wherein the cysteine or cystine concentration in the cell culture does not exceed 0.3 g/L at any time point during the production phase, and/or
    the tryptophan concentration in the cell culture does not exceed 0.6 g/L at any time point during the production phase, preferably wherein the tryptophan concentration in the cell culture does not exceed 0.3 g/L at any time point during the production phase.
71. The method according to any one of embodiments 63 to 70, wherein
    the total amount of cysteine or cystine provided during the process is from 2.9 to 12 g/($10^{12}$ cells), such as from 2.9 to 7 g/($10^{12}$ cells), wherein cells refers to the expected integral viable cell count at the end of the production phase, and/or
    the total amount of tryptophan provided during the process is from 2.5 to 7 g/($10^{12}$ cells), such as from 2.5 to 3.5 g/($10^{12}$ cells/L), wherein cells refers to the expected integral viable cell count at the end of the production phase.
72. The method according to any one of embodiments 63 to 71, wherein the method is a batch method.
73. The method according to any one of embodiments 63 to 72, wherein the recombinant protein is produced during a production phase, preferably wherein the production phase has a duration of at least 7 days, more preferably at least 14 days.
74. The method according to any one of embodiments 63 to 73, wherein the culture is supplemented daily in the production phase.
75. The method according to any one of embodiments 63 to 74, wherein the production phase is carried out in a bioreactor, preferably with a volume of equal or more than 50 L, equal or more than 100 L, equal or more than 500 L, equal or more than 1000 L, equal or more than 2,000 L, equal or more than 5,000 L, equal or more than 10,000 L or equal or more than 20,000 L.
76. The method according to any one of embodiments 63 to 75, wherein the host cells are mammalian cells, preferably CHO cells.
77. The method according to any one any one of embodiments 63 to 76, wherein the recombinant protein is an antibody or an antigen-binding fragment thereof.
78. The method according to embodiment 77, wherein the antibody or antigen-binding fragment thereof is:
    i) an antibody or antigen-binding fragment thereof which
    a. comprises CDR-H1 having the sequence as defined in SEQ ID NO:1; CDR-H2 having the sequence as defined in SEQ ID NO:2; CDR-H3 having the sequence as defined in SEQ ID NO:3; CDR-L1 having the sequence as defined in SEQ ID NO:4; CDR-L2 having the sequence as defined in SEQ ID NO:5 and CDR-L3 having the sequence as defined in SEQ ID NO:6; or
b. comprises a light variable region having the sequence as defined in SEQ ID NO: 7 and a heavy variable region having the sequence as defined in SEQ ID NO: 8; or
c. comprises a light variable region having at least 80% identity or similarity, preferably 90% identity or similarity to the sequence as defined in SEQ ID NO: 7 and a heavy variable region having at least 80% identity or similarity, preferably 90% identity or similarity to the sequence as defined in SEQ ID NO: 8;
d. comprises a light variable region having the sequence as defined in SEQ ID NO: 7 and a heavy chain having the sequence as defined in SEQ ID NO: 11; or
e. comprises a light variable region having at least 80% identity or similarity, preferably 90% identity or similarity to the sequence as defined in SEQ ID NO: 7 and a heavy chain having at least 80% identity or similarity, preferably 90% identity or similarity to the sequence as defined in SEQ ID NO: 11; or
ii) an antibody which comprises a light chain having the sequence as defined in SEQ ID NO: 9 and a heavy chain having the sequence as defined in SEQ ID NO: 10; or
iii) an antibody which comprises a light chain having at least 80% identity or similarity, preferably 90% identity or similarity to the sequence as defined in SEQ ID NO: 9 and a heavy chain having at least 80% identity or similarity, preferably 90% identity or similarity to the sequence as defined in SEQ ID NO: 10.

79. The method according to any one of embodiments 63 to 78, wherein the recombinant protein is a protein which is not colorless at a concentration of 10 mg/ml or more, such as 50 mg/ml or more, when produced by host cells grown in a cell culture medium not comprising cysteine/cystine analogs, wherein color e.g. is determined as described in the Examples herein.
80. The method according to any one of embodiments 63 to 79, wherein the method comprises the step of recovering the recombinant protein from the cell culture medium and a further step of purifying the recombinant protein.
81. The method according to embodiment 80 wherein the purification comprises Protein A chromatography.
82. The method according to embodiment 80 or 81, further comprising the step of formulating the purified recombinant protein.
83. The method according to any one of embodiments 63 to 82, wherein said host cells are CHO cells and said cysteine/cystine analog is N,N'-diacetyl-L-cystine-dimethylester.
84. A recombinant protein preparation obtainable or obtained by the method according to any one of the preceding embodiments.
85. A cell culture medium suitable for culturing mammalian cells comprising N,N'-diacetyl-L-cystine-dimethylester.

The invention will now be further described by way of examples with references to embodiments illustrated in the accompanying drawings.

EXAMPLES

Abbreviations mAb: monoclonal antibody; Cys: cysteine or cystine; APG: acidic peak group; VCC: viable cell count; DO: dissolved oxygen; $CO_2$: carbon dioxide; CHO: Chinese Hamster Ovary; UPLC: Ultra Performance Liquid Chromatography.

Example 1

The ability of cysteine/cystine derivatives to reduce color and acidic species of an antibody preparation produced recombinantly by host cells grown in cell culture was evaluated. For this experiment, a scale-down model in shake flask was used. CHO-DG44 cells producing a full-length antibody, mAb1, were inoculated in 100 mL of basal media at a seeding density of $0.35 \times 10^6$ cells/mL mAb1 comprises a light chain having the sequence as defined in SEQ ID NO: 9 and a heavy chain having the sequence as defined in SEQ ID NO: 10.

The shake flask vessels were 250 mL shake flasks (corning) disposed in an agitated incubator (Infors) protected from light. The cells were cultivated for 14 days at 36.8° C. with 80% humidity. The cell cultures were agitated at 140 rpm at the beginning of the process. The agitation was increased during the process progressively to reach 250 rpm to maintain a DO % at 40% in the shake flask, as is it done in a 2 L bioreactor process. The cell culture was maintained at pH 7.0±0.2 by decreasing the $CO_2$ in the incubator from 5% before the process to 2% during the process. Cells were cultured in a fed-batch mode with bolus addition of Feed every day of culture. The basal media contained 0.04 mmol/L of cysteine+0.38 mmol/L of cystine. The Feed contained 153.3 mmol/L of cystine. Over the entire 14-day production phase, the total volume of Feed added corresponded to 4.47% (v/v) of the culture start volume.

The cysteine present in the Feed was replaced by different cysteine and cystine derivatives at different percentages as presented in Table 1. Osmolality was daily monitored using an osmometer from Advanced Instruments. Off line pH, dissolved $O_2$ and dissolved $CO_2$ were daily monitored using a model BioProfile pHOx® blood gas analyser (Nova Biomedical Corporation, Waltham, Mass.). Metabolites concentrations were daily determined using a CedexBioHT system (Roche). Viable cell concentration and cell viability were measured daily using a ViCell automated cell counter (Beckman Coulter). The cell culture fluid was collected daily by centrifuging 1 mL of cell culture fluid for determination of antibody titer using protein A HPLC (Waters). At the end of the 14 days of culture, the cell culture fluid was harvested by centrifugation. The supernatant was then purified using a protein-A affinity chromatography (MabSelect Sure, GE). The protein A eluates were used for the molecular weight determination using UPLC size exclusion (Waters). The relative percentage of main, acidic (APG for Acidic Peak Group) and basic (BPG for Basic Peak Group) isoforms of the purified mAb was determined by Imaged Capillary Electrophoresis (PROTEINSIMPLE iCE3). Another part of the protein A eluates was concentrated to 40 mg/ml using Amicon centricon centrifugal filter devices (Millipore).

Color intensity of the concentrated antibody composition was measured in the concentrated protein A eluates using a spectrophotometer by transmission (UltrascanPro) and compared to the CIE (commission internationale de l'éclairage) scale. The numerical results were normalized to the concentration of 40 mg/mL.

FIG. 1 shows the profile of cell growth using different cysteine and cystine derivatives with different replacement ratio of the cysteine in the Feed. In conditions with 100% of Cys derivative, cell growth slowed down from day 6 compared to the control condition, except for the 100% S-sulfocysteine condition where cells rapidly died on day 7. The viable cell concentration was similar to the control condition for the 50% derivative feeds until day 10. From day 10, the viable cell densities were higher than the control condition. However, for 50% S-sulfocysteine, the viable cell concentration reached a maximum of $2 \times 10^6$ cells/mL, significantly lower than the control condition. Cells did not grow as well as the control when 100% of Cys was replaced with a Cys derivative suggesting that cysteine derivatives cannot fully replace cysteine. On the other hand, the condition with 50% derivatives exhibited a better growth than the control condition suggesting a positive impact of the cysteine/cystine derivatives when a minimum of cysteine is present. S-sulfocysteine does not seem to act as the other derivatives tested with respect to enabling cell growth.

In view of the cell death observed with the 100% cysteine derivatives, other performance and product quality results were analyzed only for 50% cysteine derivative conditions.

The product titer was higher in cultures using 50% of cysteine derivatives than the control condition except when the derivative used was S-sulfocysteine (FIG. 2).

The b*value of the concentrated protein-A eluate was decreased of between 6.5% to 21.2% compared to control condition, with the best result observed with 50% of N,N'-diacetyl-L-cystine dimethylester (CAS Registry number 32381-28-5, e.g. obtainable from Bachem AG) (FIG. 3). Likewise, a decrease on acidic variants level was also observed of between 7.6% to 24.8% compared to control condition, with the best result observed with 50% of N,N'-diacetyl-L-cystine dimethylester (FIG. 4). This decrease in acidic species level correlated with an increase of main charge species (FIG. 5) with no significant increase of basic variant level, except for the S-sulfocysteine (not shown). These results confirmed the reduction of the micro-heterogeneity of the recombinant protein.

TABLE 1

Different compositions of Feed tested

| Derivatives used | % of cysteine replaced by the derivatives in Feed (molar equivalence) |
| --- | --- |
| N-Acetyl-L-cysteine | 100 |
|  | 50 |
| N,N'-Diacetyl-L-cystine | 100 |
|  | 50 |
| N,N'-diacetyl-L-cystine dimethylester | 100 |
|  | 50 |
| S-Sulfocysteine | 100 |
|  | 50 |

Example 2

The ability of cysteine/cystine derivatives to reduce color and acidic species of a recombinant protein preparation in cell culture was evaluated using another antibody-producing cell line, cell line 2. For this experiment a scale-down model in shake flask was used. CHO-DG44 cells producing a multispecific antibody derivative were inoculated in 100 mL of basal media at a seeding density of $0.35 \times 10^6$ cells/mL. The shake flask vessels were 250 mL shake flasks (corning) disposed in an agitated incubator (Infors) protected from light. The cells were cultivated for 14 days at 36.8° C. with 80% of humidity. The cell cultures were agitated at 140 rpm at the beginning of the process. The agitation was increased during the process progressively to reach 250 rpm to maintain a DO % at 40% in the shake flask, as is it done in the 2 L bioreactor process. The cell culture was maintained at pH 7.0±0.2 by decreasing the $CO_2$ in the incubator from 5% the process to 2% during the process. Cells were cultured in a fed-batch mode with bolus addition of Feed every day of culture. The basal media contained 0.04 mmol/L of cysteine+0.38 mmol/L of cystine. The Feed contained 153.3 mmol/L of cystine. Over the entire 14-day production phase, the total volume of Feed added corresponded to 2.81% (v/v) of the culture start volume.

The cysteine present in the Feed was replaced by different cysteine and cystine derivatives with a replacement ratio of 50% equimolar (Table 1). A condition with only 50% of the control cysteine levels was also added to test whether the improvements observed were due to the presence of the cysteine derivative or to the reduction of cysteine only. Osmolality was daily monitored using an osmometer from Advanced instrument. Off line pH, dissolved O2 and dissolved CO2 were daily monitored using a Nova Biomedical Phox (Nova biomedical). Metabolites concentrations were daily determined using a CedexBioHT system (Roche). Viable cell concentration and cell viability were measured daily using a ViCell automated cell counter (Beckman Coulter). The cell culture fluid was collected daily by centrifuging 1 mL of cell culture fluid for determination of antibody titer using protein L Octet measurement (Pall). At the end of the 14 days of culture, the cell culture fluid was harvested by centrifugation. The supernatant was then purified using a protein L affinity chromatography (CaptoL, GE). The protein L eluates were used for the molecular weight determination using UPLC size exclusion (Waters) and for the charge variants determination using isocapillary focusing (PROTEINSIMPLE iCE3). The recombinant protein produced with cell line 2 was not a colored molecule. Therefore, no color measurement was performed in this case.

FIG. 6 shows the profile of cell growth using different cysteine and cystine derivatives with a replacement ratio of 50% of the cysteine in the Feed. Similar cell growth profiles were observed between control condition and conditions with cysteine and cystine derivatives. Thus, these components do not impact the cell growth for this cell line (cell line 2). The product titer was also similar to the control condition for all cysteine and cystine derivatives (FIG. 7).

As can be seen in FIG. 8, a decrease on acidic variants level was observed of between 46.6% to 50.2% compared to control condition with the two cystine derivatives, N,N'-diacetyl-L-cystine and N,N'-diacetyl-L-cystine dimethylester. A decrease of 14.5% of acidic variant level was observed with N-acetyl-cysteine. This decrease in acidic species level correlated with an increase of main charge species (FIG. 9) with no significant increase of basic variant level (data not shown). These results confirmed the reduction of the micro-heterogeneity of the recombinant protein by cystine derivative. On the other hand, an increase between 5% and 10% of acidic species was observed with S-sulfocysteine and with the reduction of cysteine only.

Example 3

The ability of cysteine/cystine derivatives to reduce color and acidic species of a recombinant protein preparation produced in cell culture was evaluated in a bioreactor for two cell lines. This model is more representative of the large-scale production than the shake flask due to the geometry and additional control. CHO-DG44 cells from cell line 1 and 2 were inoculated in 1300 mL of basal media at a seeding density of $0.35 \times 10^6$ cells/mL in 2 L stirred bioreactor (Sartorius). The cells were cultivated during 14 days in fed-batch mode. The cell cultures were agitated at 280 rpm and the DO was maintained at 40%. The cell culture was maintained at pH 7.0±0.2 with an automatic $CO_2$ sparging regulation. Cells were cultured in a fed-batch mode with bolus addition of Feed every day of culture. The basal media contained 0.04 mmol/L of cysteine+0.38 mmol/L of cystine. The Feed contained 153.3 mmol/L of cystine. Over the entire 14-day production phase, the total volume of Feed added corresponded to 5.7% (w/w) of the culture start volume for cell line 1 and to 3.1% (w/w) of the culture start volume for cell line 2.

The cysteine present in the Feed was replaced by different cysteine- and cystine derivatives at different percentages as presented in Table 2. A condition with only 50% of cysteine was added to test whether the improvements observed were due to the cysteine derivative or to the reduction of cysteine only. Osmolality was daily monitored using an osmometer from Advanced instrument. Off line pH, dissolved $O_2$ and dissolved $CO_2$ were daily monitored using a Nova Biomedical Phox (Nova biomedical). Metabolites concentrations were daily determined using a CedexBioHT system (Roche). Viable cell concentration and cell viability were measured daily using a ViCell automated cell counter (Beckman Coulter). The cell culture fluid was collected daily by centrifuging 1 mL of cell culture fluid for determination of antibody titer by HPLC prot A (waters) or using protein-L Octet measurement (Pall). At the end of the 14 days of culture, the cell culture fluid was harvested by centrifugation. The supernatant was then purified using a protein-A or L affinity chromatography (GE). The protein-A or L eluates were used for the molecular weight determination using UPLC size exclusion (Waters) and for the charge variants determination using isocapillary focusing (PROTEIN-SIMPLE iCE3). Another part of the protein-A eluates (only from cell line 1) was concentrated to 40 mg/mL using Amicon centricon centrifugal filter devices (Millipore). Color intensity of the concentrated antibody composition was measured in the concentrated protein A eluates using a spectrophotometer by transmission (UltrascanPro) and compared to the CIE (commission internationale de l'éclairage) scale. The numerical results were normalized to the concentration of 40 mg/mL.

TABLE 2

Different compositions of Feed tested with the cell line 1 and 2 in 2L bioreactor

| Derivatives used | % of cysteine replaced by the derivatives in Feed (molar equivalence) |
| --- | --- |
| N-Acetyl-L-cysteine | 50 |
| N,N'-Diacetyl-L-cystine | 50 |
| N,N'-diacetyl-L-cystine dimethylester | 50 |

Cell Line 1

Similar cell growth trends were observed for all conditions tested (FIG. 10).

A significant decrease of antibody titer was observed with N,N'-diacetyl-cystine and N-acetyl-cysteine between 10% and 17% but a non-significant decrease of less than 5% was observed with N, N'-diacetyl-L-cystine dimethylester (FIG. 11). A significant decrease of titer was observed also with the 50% cysteine feed only, suggesting that N,N'-diacetyl-L-cystine dimethylester improves the titer.

Regarding acidic species level, a decrease of 5% with N,N'-diacetyl-L-Cystine, 10% with N-acetyl-L-cysteine and 15% with N,N'-diacetyl-L-cystine dimethylester was observed (FIG. 12). This reduction correlated with an increase of main species (FIG. 13). A similar impact on charge variant was observed at 2 L scale as in shake flasks. This reduction was also observed with 50% cysteine feed only. This suggest that the acidic species level reduction here may be due to the reduction of cysteine. Decreases of the b value level of 2.5% with N,N'-diacetyl-L-Cystine, 13% with N-acetyl-L-cysteine and 25% with N,N'-diacetyl-L-cystine dimethylester were observed. A similar impact on product color intensity was observed at 2 L scale as in shake flasks. No reduction of the b*value was observed with the 50% cysteine feed only. The impact of N,N'-diacetyl-L-cystine dimethylester on coloration was confirmed.

Cell Line 2

Similar cell growth trends were observed for all conditions tested (FIG. 15).

A significant increase of antibody titer of between 15% to 23% was observed with N,N'-diacetyl-cystine, N-acetyl-cysteine and N,N'-diacetyl-L-cystine dimethylester (FIG. 16). This result is thus different from the results obtained in shake flasks.

Regarding acidic species level, a decrease of 8% with N,N'-diacetyl-L-Cystine, 13% with N-acetyl-L-cysteine and 13% with N,N'-diacetyl-L-cystine dimethylester was observed (FIG. 17). This reduction correlated with an increase of main species (FIG. 18). A similar trend for charge variants was observed at 2 L scale compared to shake flasks, except for N-acetyl-cysteine. The impact of the replacement of cysteine by N,N'-diacetyl-L-cystine dimethylester on charge variants was confirmed.

Decrease of 27% of the acid species level was observed with 50% cysteine feed. This indicates that the reduction of cysteine is the main driver for the reduction of acidic species. A titer increase of 10% was observed with 50% cysteine feed instead of 15% to 23% with the cysteine/cystine derivatives. The replacement of 50% of the cysteine by a cysteine/cystine derivative is a good compromise between titer increase and heterogeneity reduction for this cell line.

Example 4

The reproducibility of the results was evaluated in bioreactor with cell line 1. The experiments of Example 3 were repeated with an additional control and a bioreactor with 50% S-sulfocysteine 50% Cysteine Feed. The data from the two experiments were analyzed to confirm the effect previously observed with cysteine/cystine derivatives.

TABLE 3

| Feed | Number of replicates | |
|---|---|---|
| | Data set 1 | Data set 2 |
| Control 100% Cysteine Feed | 1 | 2 |
| 50% Cysteine Feed | 1 | 1 |
| 50% N-Acetyl-L-cysteine 50% Cysteine Feed | 1 | 1 |
| 50% N,N'-Diacetyl-L-cystine 50% Cysteine Feed | 1 | 1 |
| 50% N,N'-diacetyl-L-cystine dimethylester 50% Cysteine Feed | 1 | 1 |
| 50% S-sulfocysteine 50% Cysteine Feed | 0 | 1 |

No differences regarding cell growth were observed between day 0 and 8. From day 9 condition with S-sulfocysteine had a higher cell death than the control. 50% cysteine feed, 50% N,N'-diacetyl cystine 50% cysteine feed and 50% N-acetyl-cysteine 50% cysteine feed had higher VCCs than the control conditions. The 50% N,N'-diacetyl cystine dimethyl ester 50% cysteine feed condition was similar to the control conditions average (FIG. 19).

A non significant decrease in antibody titer of less than 5% compared to the controls average was observed with N,N'-diacetyl cystine dimethyl ester. However, a decrease of 10% was observed for the 50% cysteine feed. The use of N,N'-diacetyl cystine dimethyl ester has thus compensated 5% of the titer loss due to cysteine reduction in feed. Moreover, the higher VCC observed with 50% cysteine feed indicates an increase of the specific productivity with N,N'-diacetyl cystine dimethyl ester compared to 50% cysteine feed. This observation confirms that a loss of specific productivity due to reduction of cysteine can be compensated by addition of N,N'-diacetyl cystine dimethyl ester. A decrease of 10% was also observed with N-acetyl cysteine and N,N'-diacetyl cysteine. These molecules did not impact the productivity for this cell line. On the other hand, a decrease of 25% in titer was observed with S-sulfocysteine. This was due to the decrease of VCC and to the decrease of productivity due to the cysteine reduction, but not to a specific impact of S-sulfocysteine on the specific productivity (FIG. 20).

Regarding acidic species level, an average decrease of 10% with N,N'-diacetyl-L-Cystine and N-acetyl-L-cysteine were observed (FIG. 21). This reduction correlated with an increase of main species (FIG. 22).

An average reduction of 15% was observed with N,N'-diacetyl-L-Cystine. This reduction is also observed with 50% cysteine feed only. This again suggests that the acidic species level reduction is due to the reduction of cysteine levels. Similar acidic species levels were observed between S-sulfocysteine and control condition. This suggest that S-sulfocysteine increased acidic species level normally decreased by a cysteine reduction.

Regarding b value level, an average decrease of 5% with S-sulfocysteine, 14% with N,N'-diacetyl-L-Cystine, 13% with N-acetyl-L-cysteine and 30% with N,N'-diacetyl-L-cystine dimethylester were observed. No reduction of the b*value was observed with the 50% cysteine feed only. The impact of N,N'-diacetyl-L-cystine dimethylester on coloration was confirmed (FIG. 23).

Example 5

We tested different concentrations of cysteine/cystine derivatives on the improvement on the APG level of a recombinant protein preparation produced in cell culture cultivated in mini bioreactors. CHO-DG44 cells from cell line 1 were inoculated in 12 mL basal media at a seeding density of $0.35 \times 10^6$ cells/mL in Ambr15 bioreactors (Sartorius). The cells were cultivated in fed-batch mode during 14 days. The DO was maintained at 40% and the pH was maintained 7.0±0.2 with an automatic $CO_2$ sparging regulation. Viable cell concentration and cell viability were measured daily using a ViCell automated cell counter (Beckman Coulter). Cells were cultured in a fed-batch mode with a daily bolus addition of Feed. The basal media contained 0.04 mmol/L cysteine+0.38 mmol/L cystine. The Feed contained 153.3 mmol/L of cystine. Over the entire 14-day production phase, the total volume of added Feed corresponded to 4.7% (v/v) of the culture start volume.

Different percentages of cysteine present in the Feed was replaced by different cysteine- and cystine analogs. Table 4 provides an overview of different percentages tested and their equivalence in molar ratio relative to cysteine or cystine. E.g. for N-Acetyl-L-cysteine 10% means that 10% molar amount of cysteine equivalent has been replaced by 10% molar amount of N-Acetyl-L-cysteine; for N,N'-Diacetyl-L-cystine, 10% means that 10 molar amount of cystine equivalent has been replaced with 10% molar amount of N,N'-Diacetyl-L-cystine. At the end of the 14 days of culture, the cell culture fluid was harvested by centrifugation. The supernatant was then purified using a protein-A affinity chromatography (GE). The protein-A eluates were used for the charge variants determination using isocapillary focusing (PROTEINSIMPLE iCE3).

TABLE 4

Different compositions of Feed tested with the cell line 1 in Ambr15 bioreactor

| Analogs used | % of cysteine/ cystine replaced by the analogs in Feed (molar equivalence)* | molar ratio relative to cysteine (analog/ cysteine) | Analog molar concentration in Feed (mol/L) | Equivalent cysteine molar concentration in Feed (mol/L) | Equivalent cystine molar concentration in Feed (mmol/L) |
|---|---|---|---|---|---|
| N-Acetyl-L-cysteine (NAC) | 10 | 9.00:1.00 | 0.03065 | 0.27584 | 0.13792 |
| | 20 | 4.00:1.00 | 0.06130 | 0.24519 | 0.12259 |
| | 30 | 2.33:1.00 | 0.09195 | 0.21454 | 0.10727 |
| | 50 | 1.00:1.00 | 0.15324 | 0.15324 | 0.07662 |
| | 70 | 1.00:2.33 | 0.21454 | 0.09195 | 0.04597 |
| | 80 | 1.00:4.00 | 0.24519 | 0.06130 | 0.03065 |
| | 90 | 1.00:9.00 | 0.27584 | 0.03065 | 0.01532 |

TABLE 4-continued

Different compositions of Feed tested with the cell line 1 in Ambr15 bioreactor

| Analogs used | % of cysteine/cystine replaced by the analogs in Feed (molar equivalence)* | molar ratio relative to cysteine (analog/cysteine) | Analog molar concentration in Feed (mol/L) | Equivalent cysteine molar concentration in Feed (mol/L) | Equivalent cystine molar concentration in Feed (mmol/L) |
|---|---|---|---|---|---|
| N,N'-Diacetyl-L-cystine (DiNAC) | 10 | 18.00:1.00 | 0.01532 | 0.27584 | 0.13792 |
|  | 20 | 8.00:1.00 | 0.03065 | 0.24519 | 0.12259 |
|  | 30 | 4.67:1.00 | 0.04597 | 0.21454 | 0.10727 |
|  | 50 | 2.00:1.00 | 0.07662 | 0.15324 | 0.07662 |
|  | 70 | 1.00:1.17 | 0.10727 | 0.09195 | 0.04597 |
|  | 80 | 1.00:2.00 | 0.12259 | 0.06130 | 0.03065 |
|  | 90 | 1.00:4.50 | 0.13792 | 0.03065 | 0.01532 |
| N,N'-Diacetyl-L-cystine dimethylester (DACDM) | 10 | 18.00:1.00 | 0.01532 | 0.27584 | 0.13792 |
|  | 20 | 8.00:1.00 | 0.03065 | 0.24519 | 0.12259 |
|  | 30 | 4.67:1.00 | 0.04597 | 0.21454 | 0.10727 |
|  | 50 | 2.00:1.00 | 0.07662 | 0.15324 | 0.07662 |
|  | 70 | 1.00:1.18 | 0.10727 | 0.09195 | 0.04597 |
|  | 80 | 1.00:2.02 | 0.12259 | 0.06130 | 0.03065 |
|  | 90 | 1.00:4.54 | 0.13792 | 0.03065 | 0.01532 |

*for N-Acetyl-L-cysteine, the % replacement is in view of cysteine equivalent

FIG. 24 shows the growth profiles of the cells. Similar viable cell concentration profile were observed between the control condition (no analog added) and the majority of the condition tested. Inhibition of the growth was observed with 90% of N,N'-diacetyl-L-cystine and 90% N,N'-diacetyl-L-cystine dimethylester.

FIGS. 25 and 26 represents the response to different cysteine/cystine replacement level of N,N'-diacetyl-L-cystine, N,N'-diacetyl-L-cystine dimethylester or N-acetyl-cystine, in acidic species and main charge species level. For N,N'-diacetyl-L-cystine, the acidic species level is reduced with the increase of the percentage of replacement to reach a maximum reduction of 27.5%. This reduction of the microheterogeneity is confirmed by positive difference with respect to the control observed in main charge species level. The optimum main charge species level with N,N'-diacetyl-L-cystine dimethylester was obtained between 50% and 70% of cysteine/cystine replacement. However the N,N'-diacetyl-L-cystine dimethylester have a positive impact on main charge species level between 15% and 90% according to the fitting curve. This results is confirmed by the decrease of the acidic species level also observed with N,N'-diacetyl-L-cystine dimethylester in FIG. 25. Lower impact was observed with N-acetyl-cysteine with an optimum value around 70% of replacement with a decrease of acidic species of 12.5%.

The invention claimed is:

1. A method for reducing the heterogeneity of a population of recombinant proteins produced in cell culture, said method comprising growing host cells producing a recombinant protein in a cell culture medium wherein the cell culture medium comprises one or more cysteine/cystine analogs, wherein said reduction of heterogeneity comprises reducing:
   a) intensity of color;
   b) charge heterogeneity, whereby the main charge species does not decrease; and/or
   c) amino acid oxidation,
   wherein the one or more cysteine/cystine analogs are selected from the group consisting of N,N'-diacetyl-L-cystine-dimethylester, N-acetyl-L-cysteine and N,N'-diacetyl-L-cystine, wherein the recombinant proteins are antibodies or antigen binding fragments thereof, and wherein the host cells are mammalian cells.

2. The method according to claim 1, wherein said cell culture medium comprises:
   (a) cysteine/cystine analogs; and
   (b) cysteine and/or cystine,
   wherein, the molar amount of (a) is from 10 to 90 percent in view of the total molar amount of (a) and (b), wherein in case a cysteine analog is used, the molar amount of (b) is calculated in view of cysteine equivalents; and
   wherein in case a cystine analog is used, the molar amount of (b) is calculated in view of cystine equivalents.

3. The method according to claim 1, wherein the method comprises the steps of:
   (i) inoculating said host cells in a basal medium, wherein the basal medium optionally comprises an initial amount of:
   (a) cysteine/cystine analogs; and/or
   (b) cysteine and/or cystine,
   (ii) progressing the culture through a production phase wherein the recombinant protein is produced by the cells, wherein, during said production phase, the cell culture medium is supplemented with:
   (a) cysteine/cystine analogs; and
   (b) cysteine and/or cystine,
   wherein (a) and (b) may be added simultaneously or sequentially,
   wherein, when the contents of the basal medium and the total supplements added are added up, the molar amount of (a) in view of the total molar amount of (a) and (b) is from 10 to 90 percent, wherein in case a cysteine analog is used, the molar amount of (b) is calculated in view of cysteine equivalent; and
   wherein in case a cystine analog is used, the molar amount of (b) is calculated in view of cystine equivalent.

4. The method according to claim 1, wherein the recombinant protein is an antigen-binding fragment.

5. The method according to claim 1, wherein the antibody or antigen-binding fragment thereof is:
   i) an antibody or antigen-binding fragment thereof which
   a) comprises CDR-H1 having the sequence as defined in SEQ ID NO:1; CDR-H2 having the sequence as defined in SEQ ID NO:2; CDR-H3 having the sequence as defined in SEQ ID NO:3; CDR-L1 having the sequence as defined in SEQ ID NO:4; CDR-L2 having the sequence as defined in SEQ ID NO:5 and CDR-L3 having the sequence as defined in SEQ ID NO:6; or
   b) comprises a light variable region having the sequence as defined in SEQ ID NO: 7 and a heavy variable region having the sequence as defined in SEQ ID NO: 8; or
   c) comprises a light variable region having the sequence as defined in SEQ ID NO: 7 and a heavy chain having the sequence as defined in SEQ ID NO: 11; or
   ii) an antibody which comprises a light chain having the sequence as defined in SEQ ID NO: 9 and a heavy chain having the sequence as defined in SEQ ID NO: 10.

6. The method according to claim 1, wherein said cell culture medium comprises:
   (a) cysteine/cystine analogs; and
   (b) cysteine and/or cystine,
   wherein the molar ratio of (a) to (b) is between 1:10 and 10:1.

7. The method according to claim 6, wherein said molar ratio of (a) to (b) is between 1:8 and 8:1.

8. The method according to claim 7, wherein said molar ratio of (a) to (b) is between 1:6 and 6:1.

9. The method according to claim 7, wherein said molar ratio of (a) to (b) is between 1:4 and 4:1.

10. The method according to claim 7, wherein said molar ratio of (a) to (b) is between 1:3 and 3:1.

11. The method according to claim 7, wherein said molar ratio of (a) to (b) is between 1:2 and 2:1.

12. The method according to claim 1, wherein the method comprises the steps of:
    (i) inoculating said host cells in a basal medium, wherein the basal medium optionally comprises an initial amount of:
    (a) cysteine/cystine analogs; and/or
    (b) cysteine and/or cystine,
    (ii) progressing the culture through a production phase wherein the recombinant protein is produced by the cells, wherein, during said production phase, the cell culture medium is supplemented with:
    (a) cysteine/cystine analogs; and
    (b) cysteine and/or cystine,
    wherein (a) and (b) may be added simultaneously or sequentially,
    wherein, when the contents of the basal medium and the total supplements added are added up, the molar ratio of (a) to (b) is between 1:10 and 10:1.

13. The method according to claim 12, wherein the concentration of (b) in said basal medium is equivalent to between 0.05 and 5 mmol/L of cysteine.

14. The method according to claim 13, wherein the concentration of (b) in said basal medium is equivalent to between 0.1 and 1 mmol/L of cysteine.

15. The method according to claim 13, wherein the concentration of (b) in said basal medium is equivalent to between 0.2 and 0.6 mmol/L of cysteine.

16. The method according to claim 12, wherein, during the production phase, the medium is supplemented with (a) cysteine/cystine analogs and (b) cysteine and/or cystine, wherein the sum of (a) and (b) added to the culture over the entire production phase is equivalent to between 1 and 75 mmol/L of cysteine.

17. The method according to claim 16, wherein, during the production phase, the medium is supplemented with (a) cysteine/cystine analogs and (b) cysteine and/or cystine, wherein the sum of (a) and (b) added to the culture over the entire production phase is equivalent to between 2 and 20 mmol/L.

18. The method according to claim 12, wherein, during the production phase, the medium is supplemented daily with (a) cysteine/cystine analogs and (b) cysteine and/or cystine, wherein the daily addition brings the concentration of (a)+(b) to a concentration equivalent to between 0.05 and 5 mmol/L of cysteine.

19. The method according to claim 18, wherein, during the production phase, the medium is supplemented daily with (a) cysteine/cystine analogs and (b) cysteine and/or cystine, wherein the daily addition brings the concentration of (a)+(b) to a concentration equivalent to between 0.1 and 1 mmol/L of cysteine.

20. The method according to claim 1, wherein the recombinant protein is a protein which is not colorless at a concentration of 10 mg/ml or more, when produced by host cells grown in a cell culture medium not comprising cysteine/cystine analogs.

21. The method according to claim 20, wherein the recombinant protein is a protein which is not colorless at a concentration of 50 mg/ml or more, when produced by host cells grown in a cell culture medium not comprising cysteine/cystine analogs.

22. A method for producing a recombinant protein preparation comprising:
(i) inoculating said host cells in a basal medium, wherein the basal medium optionally comprises an initial amount of:
(a) cysteine/cystine analogs; and/or
(b) cysteine and/or cystine,
(ii) progressing the culture through a production phase wherein the recombinant protein is produced by the cells, wherein, during said production phase, the cell culture medium is supplemented with:
(a) cysteine/cystine analogs; and
(b) cysteine and/or cystine,
wherein (a) and (b) may be added simultaneously or sequentially,
wherein, when the contents of the basal medium and the total supplements added are added up, the molar ratio of (a) to (b) is between 1:10 and 10:1,
wherein the cysteine/cystine analogs are selected from the group consisting of N,N'-diacetyl-L-cystine-dimethylester, N-acetyl-L-cysteine and N,N'-diacetyl-L-cystine, wherein the recombinant proteins are antibodies, and wherein the host cells are mammalian cells.

23. A method for producing a recombinant protein preparation comprising:
(i) inoculating said host cells in a basal medium, wherein the basal medium optionally comprises an initial amount of:
(a) cysteine/cystine analogs; and/or
(b) cysteine and/or cystine,
(ii) progressing the culture through a production phase wherein the recombinant protein is produced by the cells, wherein, during said production phase, the cell culture medium is supplemented with:
(a) cysteine/cystine analogs; and
(b) cysteine and/or cystine,
wherein (a) and (b) may be added simultaneously or sequentially,
wherein, when the contents of the basal medium and the total supplements added are added up, the molar amount of (a) in view of the total molar amount of (a) and (b) is from 10 to 90 percent, wherein in case a cysteine analog is used, the molar amount of (b) is calculated in view of cysteine equivalent;
wherein in case a cystine analog is used, the molar amount of (b) is calculated in view of cystine equivalent; and
wherein the cysteine/cystine analogs are selected from the group consisting of N,N'-diacetyl-L-cystine-dimethylester, N-acetyl-L-cysteine and N,N'-diacetyl-L-cystine, wherein the recombinant proteins are antibodies, and wherein the host cells are mammalian cells.

* * * * *

SEQUENCE LISTING

```
<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: Humanized

<400> SEQUENCE: 1

Gly Phe Thr Phe Ser Asn Tyr Gly Met Val
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Humanised

<400> SEQUENCE: 2

Tyr Ile Asp Ser Asp Gly Asp Asn Thr Tyr Tyr Arg Asp Ser Val Lys
1               5                   10                  15

Gly

<210> SEQ ID NO 3
<211> LENGTH: 8
```

```
<212> TYPE: PRT
<213> ORGANISM: Artificial Sequence
<220> FEATURE:
<223> OTHER INFORMATION: Huminazed

<400> SEQUENCE: 3

Gly Ile Val Arg Pro Phe Leu Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: Humanized

<400> SEQUENCE: 4

Lys Ser Ser Gln Ser Leu Val Gly Ala Ser Gly Lys Thr Tyr Leu Tyr
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Humanized

<400> SEQUENCE: 5

Leu Val Ser Thr Leu Asp Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Humanized

<400> SEQUENCE: 6

Leu Gln Gly Thr His Phe Pro His Thr
1               5

<210> SEQ ID NO 7
<211> LENGTH: 112
<212> TYPE: PRT
<213> ORGANISM: Artificial Sequence
<220> FEATURE:
<223> OTHER INFORMATION: Humanized

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Val Gly Ala
            20                  25                  30

Ser Gly Lys Thr Tyr Leu Tyr Trp Leu Phe Gln Lys Pro Gly Lys Ala
        35                  40                  45

Pro Lys Arg Leu Ile Tyr Leu Val Ser Thr Leu Asp Ser Gly Ile Pro
    50                  55                  60

Ser Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Phe Pro His Thr Phe Gly Gln Gly Thr Lys Leu Glu Ile Lys
            100                 105                 110
```

<210> SEQ ID NO 8
<211> LENGTH: 116
<212> TYPE: PRT
<213> ORGANISM: Artificial Sequence
<220> FEATURE:
<223> OTHER INFORMATION: Humanized

<400> SEQUENCE: 8

```
Glu Val Pro Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Thr Gly Ile Val Arg Pro Phe Leu Tyr Trp Gly Gln Gly Thr Leu
            100                 105                 110

Val Thr Val Ser
        115
```

<210> SEQ ID NO 9
<211> LENGTH: 219
<212> TYPE: PRT
<213> ORGANISM: Artificial Sequence
<220> FEATURE:
<223> OTHER INFORMATION: Humanized

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Val Gly Ala
            20                  25                  30

Ser Gly Lys Thr Tyr Leu Tyr Trp Leu Phe Gln Lys Pro Gly Lys Ala
        35                  40                  45

Pro Lys Arg Leu Ile Tyr Leu Val Ser Thr Leu Asp Ser Gly Ile Pro
    50                  55                  60

Ser Arg Phe Ser Gly Ser Gly Ser Gly Thr Glu Phe Thr Leu Thr Ile
65                  70                  75                  80

Ser Ser Leu Gln Pro Glu Asp Phe Ala Thr Tyr Tyr Cys Leu Gln Gly
                85                  90                  95

Thr His Phe Pro His Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
```

```
                180                 185                 190
Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 10
<211> LENGTH: 444
<212> TYPE: PRT
<213> ORGANISM: Artificial Sequence
<220> FEATURE:
<223> OTHER INFORMATION: Humanized

<400> SEQUENCE: 10

Glu Val Pro Leu Val Glu Ser Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Val Trp Val Arg Gln Ala Pro Gly Lys Gly Leu Glu Trp Val
        35                  40                  45

Ala Tyr Ile Asp Ser Asp Gly Asp Asn Thr Tyr Tyr Arg Asp Ser Val
50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Thr Gly Ile Val Arg Pro Phe Leu Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
```

```
                        325                 330                 335
Lys Gly Gln Pro Arg Glu Pro Gln Val Tyr Thr Leu Pro Pro Ser Gln
                340                 345                 350
Glu Glu Met Thr Lys Asn Gln Val Ser Leu Thr Cys Leu Val Lys Gly
                355                 360                 365
Phe Tyr Pro Ser Asp Ile Ala Val Glu Trp Glu Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
                420                 425                 430
Tyr Thr Gln Lys Ser Leu Ser Leu Ser Leu Gly Lys
                435                 440

<210> SEQ ID NO 11
<211> LENGTH: 220
<212> TYPE: PRT
<213> ORGANISM: Artificial Sequence
<220> FEATURE:
<223> OTHER INFORMATION: Humanized

<400> SEQUENCE: 11

Glu Val Pro Leu Val Glu Ser Gly Gly Gly Leu Val Gln Pro Gly Gly
1               5                   10                  15
Ser Leu Arg Leu Ser Cys Ala Val Ser Gly Phe Thr Phe Ser Asn Tyr
            20                  25                  30
Gly Met Val Trp Val Arg Gln Ala Pro Gly Lys Gly Leu Glu Trp Val
        35                  40                  45
Ala Tyr Ile Asp Ser Asp Gly Asp Asn Thr Tyr Tyr Arg Asp Ser Val
    50                  55                  60
Lys Gly Arg Phe Thr Ile Ser Arg Asp Asn Ala Lys Ser Ser Leu Tyr
65                  70                  75                  80
Leu Gln Met Asn Ser Leu Arg Ala Glu Asp Thr Ala Val Tyr Tyr Cys
                85                  90                  95
Thr Thr Gly Ile Val Arg Pro Phe Leu Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys
    210                 215                 220
```